US009796775B2

(12) United States Patent
Ido et al.

(10) Patent No.: US 9,796,775 B2
(45) **Date of Patent: *Oct. 24, 2017**

(54) METHOD FOR DETECTING PANCREATIC CANCER

(75) Inventors: Takayoshi Ido, Kanagawa (JP); Fumiyoshi Okano, Kanagawa (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/236,807

(22) PCT Filed: Aug. 3, 2012

(86) PCT No.: PCT/JP2012/069824

§ 371 (c)(1), (2), (4) Date: Feb. 3, 2014

(87) PCT Pub. No.: WO2013/018885

PCT Pub. Date: Feb. 7, 2013

(65) Prior Publication Data

US 2014/0179558 A1 Jun. 26, 2014

(30) Foreign Application Priority Data

Aug. 4, 2011 (JP) ................................. 2011-171364

(51) Int. Cl.

| | |
|---|---|
| ***A61K 39/395*** | (2006.01) |
| ***A61K 47/48*** | (2006.01) |
| ***A61K 39/00*** | (2006.01) |
| ***A61K 35/39*** | (2015.01) |
| ***C07K 16/18*** | (2006.01) |
| ***C07K 14/47*** | (2006.01) |
| ***G01N 33/574*** | (2006.01) |
| ***C07K 16/30*** | (2006.01) |
| ***C12Q 1/68*** | (2006.01) |

(52) U.S. Cl.

CPC .............. *C07K 16/18* (2013.01); *C07K 14/47* (2013.01); *C07K 14/4738* (2013.01); *C07K 16/30* (2013.01); *C07K 16/303* (2013.01); *C12Q 1/6886* (2013.01); *G01N 33/57438* (2013.01); *C07K 2317/34* (2013.01); *C07K 2317/56* (2013.01); *C12Q 2600/158* (2013.01); *G01N 2333/705* (2013.01)

(58) Field of Classification Search

None

See application file for complete search history.

(56) References Cited

U.S. PATENT DOCUMENTS

| | | | |
|---|---|---|---|
| 5,698,396 | A | 12/1997 | Pfreundschuh |
| 6,335,170 | B1 | 1/2002 | Orntoft |
| 6,444,425 | B1 | 9/2002 | Reed et al. |
| 7,449,184 | B2 | 11/2008 | Allison et al. |
| 7,485,302 | B2 | 2/2009 | Adams et al. |
| 7,745,391 | B2 | 6/2010 | Mintz et al. |
| 8,211,634 | B2 | 7/2012 | Depinho et al. |
| 8,709,418 | B2 | 4/2014 | Okano et al. |
| 8,828,398 | B2 | 9/2014 | Kobayashi et al. |
| 8,911,740 | B2 | 12/2014 | Saito et al. |
| 8,937,160 | B2 | 1/2015 | Kobayashi et al. |
| 9,115,200 | B2 | 8/2015 | Okano et al. |
| 9,175,074 | B2 | 11/2015 | Okano et al. |
| 9,180,187 | B2 | 11/2015 | Ido et al. |
| 9,180,188 | B2 | 11/2015 | Kobayashi et al. |
| 9,181,334 | B2 | 11/2015 | Kobayashi et al. |
| 9,181,348 | B2 | 11/2015 | Kobayashi et al. |
| 9,260,513 | B2 | 2/2016 | Kobayashi et al. |
| 9,266,958 | B2 | 2/2016 | Kobayashi et al. |
| 9,273,128 | B2 | 3/2016 | Okano et al. |
| 9,273,130 | B2 | 3/2016 | Kobayashi et al. |
| 9,409,993 | B2 | 8/2016 | Minamida et al. |
| 9,416,191 | B2 | 8/2016 | Kobayashi et al. |
| 9,416,193 | B2 | 8/2016 | Saito et al. |
| 9,428,581 | B2 | 8/2016 | Saito et al. |
| 9,573,993 | B2 | 2/2017 | Okano et al. |
| 2002/0006404 | A1 | 1/2002 | Hanna et al. |
| 2003/0118599 | A1 | 6/2003 | Algate et al. |
| 2003/0190640 | A1 | 10/2003 | Faris et al. |
| 2004/0029114 | A1 | 2/2004 | Mack et al. |

(Continued)

FOREIGN PATENT DOCUMENTS

| | | | |
|---|---|---|---|
| CN | 1705676 | A | 12/2005 |
| CN | 101120252 | A | 2/2008 |

(Continued)

OTHER PUBLICATIONS

PJ Carter, Nat Rev Immunol. 2006; 6:343-57.*

Chames et al ("Chames", British J. of Pharmacology, 2009, 157, 220-233).*

Bodey et al., "MAGE-1, a Cancer/Testis-Antigen, Expression in Childhood Astrocytomas as an Indicator of Tumor Progression," in vivo (2002) vol. 16, pp. 583-588.

(Continued)

*Primary Examiner* — Mark Halvorson

*Assistant Examiner* — Kauser Akhoon

(74) *Attorney, Agent, or Firm* — Birch, Stewart, Kolasch & Birch, LLP

(57) ABSTRACT

This invention relates to a method for detecting pancreatic cancer using novel tumor markers. Specifically, the invention provides a method for detecting pancreatic cancer comprising measuring the presence or an amount of a polypeptide having an reactivity of binding via an antigen-antibody reaction to an antibody against CAPRIN-1 protein in a sample separated from a subject, and to a reagent or kit for detecting pancreatic cancer comprising a CAPRIN-1 protein or a fragment thereof, an antibody against the same, or a polynucleotide encoding the same.

6 Claims, No Drawings

(56) References Cited

U.S. PATENT DOCUMENTS

2004/0236091 A1 11/2004 Chicz et al.
2004/0258678 A1 12/2004 Bodary et al.
2005/0003390 A1 1/2005 Axenovich et al.
2005/0032113 A1 2/2005 Tanaka et al.
2005/0129690 A1 6/2005 Bowdish et al.
2005/0244413 A1 11/2005 Adolf et al.
2006/0019256 A1 1/2006 Clarke et al.
2006/0069054 A1 3/2006 Houghton et al.
2006/0275305 A1 12/2006 Bryant
2007/0048301 A1 3/2007 Bodary-Winter et al.
2007/0083334 A1 4/2007 Mintz et al.
2007/0154931 A1 7/2007 Radich et al.
2007/0264253 A1 11/2007 Liu et al.
2008/0075722 A1 3/2008 DePinho et al.
2008/0107668 A1 5/2008 Philip et al.
2008/0161293 A1 7/2008 Yoshinaga et al.
2008/0306018 A1* 12/2008 Croce et al. .................... 514/44
2010/0068724 A1 3/2010 Fung et al.
2011/0123492 A1 5/2011 Okano et al.
2011/0136121 A1 6/2011 Okano et al.
2011/0189700 A1 8/2011 Moses et al.
2011/0256144 A1 10/2011 Okano et al.
2012/0171699 A1 7/2012 Goodman et al.
2012/0214975 A1 8/2012 Sandig et al.
2012/0294860 A1 11/2012 Ido et al.
2012/0301471 A1 11/2012 Kobayashi et al.
2012/0301476 A1 11/2012 Okano et al.
2012/0321641 A1 12/2012 Okano et al.
2013/0045210 A1 2/2013 Kobayashi et al.
2013/0071398 A1 3/2013 Saito et al.
2014/0154261 A1* 6/2014 Okano et al. .............. 424/139.1
2014/0178373 A1* 6/2014 Kobayashi et al. ....... 424/133.1
2014/0186359 A1 7/2014 Okano et al.
2014/0193434 A1* 7/2014 Kobayashi et al. ....... 424/174.1
2014/0199311 A1* 7/2014 Kobayashi et al. ....... 424/135.1
2014/0308283 A1 10/2014 Minamida et al.
2015/0004171 A1* 1/2015 Kobayashi et al. ....... 424/139.1
2015/0017172 A1* 1/2015 Kobayashi et al. ....... 424/139.1
2015/0044221 A1* 2/2015 Kobayashi et al. ....... 424/139.1
2015/0050283 A1* 2/2015 Okano et al. .............. 424/139.1
2015/0218285 A1 8/2015 Saito et al.
2016/0297889 A1 10/2016 Okano et al.

FOREIGN PATENT DOCUMENTS

CN 101189516 A 5/2008
CN 101836116 A 9/2010
CN 102170907 A 8/2011
CN 102171570 A 8/2011
EP 2 207 037 A1 7/2010
EP 2 325 648 A1 5/2011
EP 2322221 A1 5/2011
EP 2 532 367 A1 12/2012
EP 2 532 743 A1 12/2012
EP 2 740 794 A1 6/2014
EP 2 832 365 A1 2/2015
EP 2 832 366 A1 2/2015
JP 2002-540790 A 12/2002
JP 2003-528587 A 9/2003
JP 2006-316040 A 11/2006
JP 2013-502205 A 1/2013
JP 2013-505028 A 2/2013
RU 2161042 C2 12/2000
RU 2319709 C2 1/2003
RU 2234942 C2 2/2003
RU 2244720 C2 1/2005
RU 2306952 C2 9/2007
RU 2006137060 A 4/2008
RU 2391982 C2 6/2010
WO WO 96/09551 A1 3/1996
WO WO 00/04149 A2 1/2000
WO WO 00/05268 A1 2/2000
WO WO 00/60077 A2 10/2000
WO WO 01/32910 A2 5/2001
WO WO 01/72295 A2 10/2001
WO WO 02/078524 A2 10/2002
WO WO 02/083070 A2 10/2002
WO WO 02/092001 A2 11/2002
WO WO 03/007889 A2 1/2003
WO WO 2004/076682 A2 9/2004
WO WO 2004/097051 A2 11/2004
WO WO 2005/007830 A2 1/2005
WO WO 2005/100998 A2 10/2005
WO WO 2005/116076 A2 12/2005
WO WO 2006/002378 A2 1/2006
WO WO 2007/150077 A2 12/2007
WO WO 2008/031041 A2 3/2008
WO WO 2008/059252 A2 5/2008
WO WO 2008/073162 A2 6/2008
WO WO 2008/088583 A2 7/2008
WO WO 2009/113742 A1 9/2009
WO WO 2009/117277 A2 9/2009
WO WO 2010/016525 A1 2/2010
WO WO 2010/016526 A1 2/2010
WO WO 2010/016527 A1 2/2010
WO WO 2011/096517 A1 8/2011
WO WO 2011/096519 A1 8/2011
WO WO 2011/096528 A1 8/2011
WO WO 2011/096533 A1 8/2011
WO WO 2011/096534 A1 8/2011
WO WO 2011/096535 A1 8/2011
WO WO 2012/005550 A2 1/2012
WO WO 2012/013609 A1 2/2012
WO WO 2013/018885 A1 2/2013
WO WO 2013/018886 A1 2/2013
WO WO 2013/018894 A1 2/2013
WO WO 2013/147169 A1 10/2013
WO WO 2013/147176 A1 10/2013

OTHER PUBLICATIONS

Comtesse et al., "Probing the human natural autoantibody repertoire using an immunoscreening approach," Clin. Exp. Immunol. (2000), vol. 121, pp. 430-436.

International Search Report dated Nov. 18, 2014, in PCT International Application No. PCT/JP2014/071094.

Jager et al., "Identification of a Tissue-specific Putative Transcription Factor in Breast Tissue by Serological Screening of a Breast Cancer Library," Cancer Research (Mar. 1, 2001), vol. 61, pp. 2055-2061.

Jungbluth et al., "Immunohistochemical Analysis of NY-ESO-1 Antigen Expression in Normal and Malignant Human Tissues," Int. J. Cancer (2001), vol. 92, pp. 856-860.

Kohler et al., "Tumor antigen analysis in neuroblastoma by serological interrogation of bioinformatic data," Cancer Science (Nov. 2010), vol. 101, No. 11, pp. 2316-2324.

Nakamura et al. "Gene Expression Profile of Metastatic Human Pancratic Cancer Cells Depends on the Organ Microenvironment," Cancer Research (Jan. 1, 2007), vol. 67, No. 1, pp. 139-148.

Non-Final Office Action dated Nov. 6, 2014, in U.S. Appl. No. 13/576,950.

Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.

Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.

Gong et al., "Caprin-1 is a novel microRNA-223 target for regulating the proliferation and invasion of human breast cancer cells," Biomedicine & Pharmacotheraphy (2013), vol. 67, pp. 629-636.

Qui et al., "Targeting a ribonucleoprotein complex containing the caprin-1 protein and the c-Myc mRNA suppresses tumor growth in mice: an identification of a novel oncotarget," Oncotarget (2014), vol. 6, No. 4, pp. 2148-2163.

Sabile et al., "Caprin-1, a novel Cyr61-interacting protein, promotes osteosarcoma tumor growth and lung metastasis in mice," Biochimica et Biophysica Acta (2013), vol. 1832, pp. 1173-1182.

Akiyoshi, "Cancer Vaccine Therapy Using Peptides Derived from Tumor-Rejection Antigens," Jpn J Cancer Chemother., vol. 24, No. 5, Mar. 1997, pp. 511-519, with English Abstract (p. 519).

(56) References Cited

OTHER PUBLICATIONS

Balmana et al., "BRCA in breast cancer: ESMO Clinical Recommendations," Annals of Oncology, vol. 20, Supplemental 4, 2009, pp. iv19-iv20.
Bodey et al., "Failure of Cancer Vaccines: The Significant Limitations of this Approach to Immunotherapy," Anticancer Research, vol. 20, 2000, pp. 2665-2676.
Brand et al., "Prospect for Anti-HER2 Receptor Therapy in Breast Cancer," Anticancer Research, vol. 26, 2006, pp. 463-470.
Brass et al., "Translation initiation factor eIF-4gamma is encoded by an amplified gene and induces an immune response in squamous cell lung carcinoma," Human Molecular Genetics, vol. 6, No. 1, 1997, pp. 33-39.
Chamberlain et al., "Innovations and strategies for the development of anticancer vaccines," Expert Opinion on Pharmacotherapy, vol. 1, No. 4, 2000, pp. 603-614.
Chinese Office Action, dated Mar. 29, 2013, for Chinese Application No. 200980139037.X.
Chinese Office Action, dated May 9, 2013, for Chinese Application No. 201180016730.5.
Ellis, et al., "Identification and Characterization of a Novel Protein (p137) Which Transcytoses Bidirectionally in Caco-2 Cells", The Journal of Biological Chemistry, Sep. 1, 1995, vol. 270, No. 35, pp. 20717-20723.
European Search Report, dated Aug. 13, 2013, for European Application No. 11739882.6.
European Search Report, dated Aug. 26, 2011, for European Application No. No. 09805010.7.
European Search Report, dated Jan. 30, 2013, for European Application 09805009.9.
European Search Report, dated Nov. 6, 2013, for European Application No. 11739876.8.
Evans et al., "Vaccine therapy for cancer-fact or fiction?", Q J Med, vol. 92, 1999, pp. 299-307.
GeneCards, "Cell Cycle Associated Protein 1—Biological research products for CAPRIN 1," updated Mar. 19, 2013, 10 pages.
Grill et al., "Activation/Division of Lymphocytes Results in Increased Levels of Cytoplasmic Activation/Proliferation-Associated Protein-1: Prototype of a New Family of Proteins," The Journal of Immunology, vol. 172, 2004, pp. 2389-2400.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Gure et al., "SSX: A Multigene Family with Several Members Transcribed in Normal Testis and Human Cancer," Int. J. Cancer, vol. 72, 1997, pp. 965-971.
Harlow et al., "Antibodies a Laboratory Manual", Cold Spring Harbor Laboratory, Chapter 3, 1988, pp. 23-34.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
International Search Report and Written Opinion of the International Searching Authority, dated Mar. 1, 2011, for International Application No. PCT/JP2011/052413.
International Search Report, dated Mar. 15, 2011, for International Application No. PCT/JP2011/052384.
International Search Report, dated Mar. 8, 2011, for International Application No. PCT/JP2011/052403.
International Search Report, dated Mar. 8, 2011, for International Application No. PCT/JP2011/052414.
International Search Report, dated Oct. 6, 2009, for International Application No. PCT/JP2009/063882.
International Search Report, dated Sep. 8, 2009, for International Application No. PCT/JP2009/063883.
Itoh et al., "HUB1 is an autoantigen frequently eliciting humoral immune response in patients with adult T cell leukemia," Int. J. Oncol., vol. 14, No. 4, Apr. 1999, pp. 703-708 (Abstract only provided).
Jang et al., "Antihypertensive Angiotensin I-Converting Enzyme Inhibitory Activity and Antioxidant Activity of Vitis hybrid-Vitis coignetiae Red Wine Made with *Saccharomyces cerevisiae*," Mycobiology, vol. 39, No. 2, 2011, pp. 137-139.
Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Karauzum et al., "Caprin 1 is Frequently Overexpressed in Human Lymphomas," American Society of Human Genetics, Cancer Genetics, Program No. 1190W, Oct. 12, 2011, One page (Abstract only).
Kataja et al., "Primary breast cancer: ESMO Clinical Recommendations for diagnosis, treatment and follow-up," Annals of Oncology, vol. 20, Supplement 4, 2009, pp. iv10-iv14.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Katsafanas et al., "Vaccinia Virus Intermediate Stage Transcription Is Complemented by Ras-GTPase-activating Protein SH3 Domain-binding Protein (G3BP) . . . ," Jour of Biol. Chem., vol. 279, No. 50, Dec. 10, 2004, pp. 52210-52217.
Kolobova et al., "Microtubule-dependent association of AKAP350A and CCAR1 with RNA stress granules," Experimental Cell Research, vol. 315, 2009 (Available online Dec. 3, 2008), pp. 542-555.
Lu et al., "Identification of an immunological signature of tumor rejection in the neu transgenic mouse," 2007 AACR Annual Meeting, Apr. 14-18, 2007 (Presentation conducted on Apr. 17, 2007), One page (Abstract only provided).
Lu et al., "Targeting serum antibody for cancer diagnosis: a focus on colorectal cancer," Expert Opin. Ther. Targets, vol. 11, No. 2, 2007, pp. 235-244.
Müller-Pillasch et al., "Identification of a new tumour-associated antigen TM4SF5 and its expression in human cancer," Gene, vol. 208, 1998, pp. 25-30.
Munodzana et al., "Conformational Dependence of Anaplasma marginale Major Surface Protein 5 Surface-Exposed B-Cell Epitopes", Infection and Immunity, vol. 66, No. 6, Jun. 1998, pp. 2619-2624.
NCBI Reference Sequence, caprin-1 [Bos taurus], 2009, Accession No. NP_001069530, XP_615677, 1 page.
NCBI Reference Sequence, caprin-1 [Gallus gallus], 2005, Accession No. NP_001026536, XP_423820, 1 page.
NCBI Reference Sequence, caprin-1 isoform 1 [*Homo sapiens*], 1995, Accession No. NP_005889, 3 pages.
NCBI Reference Sequence, caprin-1 isoform 2 [*Homo sapiens*], 1995, Accession No. NP_976240, 3 pages.
NCBI Reference Sequence, caprin-1 isoform a [Mus musculus], 1996, Accession No. NP_058019, 3 pages.
NCBI Reference Sequence, caprin-1 isoform b [Mus musculus], 1996, Accession No. NP_001104760, 3 pages.
NCBI Reference Sequence, caprin-1 isoform c [Mus musculus], 1996, Accession No. NP_001104761, 4 pages.
NCBI Reference Sequence, Predicted: caprin-1 [Equus caballus], 2008, Accession No. XP_001492799, 1 page.
NCBI Reference Sequence, Predicted: caprin-1 isoform 2 [Canis lupus familiaris], Dec. 2, 2011, Accession No. XP_858109, 1 page.
Nelson et al., "Screening for Breast Cancer: An Update for the U.S. Preventive Services Task Force," Ann. Intern. Med., vol. 151, No. 10, Nov. 17, 2009, pp. 727-737.
Okano et al., "Abstract 519: Identification of a novel target for antibody therapy of breast cancer", Cancer Research, vol. 72, Issue 8, Supplement 1, Apr. 15, 2012, XP-002700046, 2 pages.
Polyak et al., "Alanine-170 and proline-172 are critical determinants for extracellular CD20 epitopes; heterogeneity in the fine specificity of CD20 monoclonal antibodies is defined by additional requirements imposed by both amino acid sequence . . . ", Blood, vol. 99, No. 9, May 1, 2002, pp. 3256-3262.
R & D Systems, "IHC Products & Protocol Guide," printed Jan. 9, 2014, pp. 1-112.

(56) References Cited

OTHER PUBLICATIONS

Russian Notice of Allowance, dated Jan. 24, 2014, for Russian Application No. 2011108258/15.
Russian Notice of Allowance, dated Jun. 7, 2013, for Russian Application No. 2011108260/10.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
Scanlan et al., "Characterization of Human Colon Cancer Antigens Recognized by Autologous Antibodies," Int. J. Cancer, vol. 76, 1998, pp. 652-658.
Solomon et al., "Distinct Structural Features of Caprin-1 Mediate Its Interaction with G3BP-1 and Its Induction of Phosphorylation of Eukaryotic Translation Initiation Factor 2α, Entry to Cytoplasmic Stress . . . ," Molecular and Cellular Biology, vol. 27, No. 6, Mar. 2007, XP_002690351, pp. 2324-2342.
Strome et al., "A Mechanistic Perspective of Monoclonal Antibodies in Cancer Therapy Beyond Target-Related Effects," The Oncologist, vol. 12, 2007, pp. 1084-1095.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
United States Notice of Allowance, dated Dec. 2, 2013, for U.S. Appl. No. 13/576,955.
United States Office Action, dated Aug. 19, 2013, for U.S. Appl. No. 13/576,955.
United States Office Action, dated Aug. 26, 2013, for U.S. Appl. No. 13/576,950.
United States Office Action, dated Dec. 21, 2012, for U.S. Appl. No. 13/057,515.
United States Office Action, dated Dec. 21, 2012, for U.S. Appl. No. 13/057,709.
United States Office Action, dated Jan. 16, 2014, for U.S. Appl. No. 13/057,515.
United States Office Action, dated Jul. 1, 2013, for U.S. Appl. No. 13/057,515.
United States Office Action, dated Jul. 1, 2013, for U.S. Appl. No. 13/577,212.
United States Office Action, dated Jul. 16, 2013, for U.S. Appl. No. 13/057,709.
United States Office Action, dated Jun. 14, 2013, for U.S. Appl. No. 13/576,969.
United States Office Action, dated Mar. 13, 2013, for U.S. Appl. No. 13/576,955.
United States Office Action, dated Nov. 15, 2013, for U.S. Appl. No. 13/576,953.
United States Office Action, dated Nov. 15, 2013, for U.S. Appl. No. 13/577,028.
United States Office Action, dated Nov. 15, 2013, in U.S. Appl. No. 13/576,950.
United States Office Action, dated Nov. 2, 2012, for U.S. Appl. No. 13/057,709.
United States Office Action, dated Nov. 9, 2012, for U.S. Appl. No. 13/057,515.
United States Office Action, dated Oct. 15, 2013, for U.S. Appl. No. 13/576,969.
United States Office Action, dated Oct. 21, 2013, for U.S. Appl. No. 13/577,212.
United States Office Action, dated Sep. 19, 2013, for U.S. Appl. No. 13/577,028.
United States Office Action, dated Sep. 6, 2013, for U.S. Appl. No. 13/576,953.
Van Der Bruggen et al., "A Gene Encoding an Antigen Recognized by Cytolytic T Lymphocytes on a Human Melanoma," Science, vol. 254, Dec. 13, 1991, pp. 1643-1647 (Also published in J. Immunol., vol. 178, 2007, pp. 2617-2621).
Wang et al., "Absence of Caprin-1 Results in Defects in Cellular Proliferation", The Journal of Immunology, 2005, vol. 175, pp. 4274-4282.
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.
Extended European Search Report dated Mar. 18, 2015, in European Patent Application No. 12820225.6.
Extended European Search Report dated Mar. 23, 2015, in European Patent Application No. 12820596.0.
Non-Final Office Action dated Apr. 14, 2015, in U.S. Appl. No. 14/236,793.
U.S. Office Action for U.S. Appl. No. 14/379,867, dated Jun. 24, 2015.
GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_016739, Feb. 10, 2008.
GenBank Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
Patent Examination Report No. 1 dated Oct. 14, 2014, in Australian Patent Application No. 2009278387.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report dated Feb. 2, 2015, in European Patent Application No. 12819473.5.
Extended European Search Report dated Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. (2002), vol. 169, pp. 3076-3084.
Extended European Search Report dated Mar. 2, 2015, in European Patent Application No. 12819759.7.
Office Action dated Jan. 28, 2015, in Russian patent Application No. 2012137502, with partial English translation.
Riechmann et al., "Reshaping human antibodies for therapy," Nature (Mar. 24, 1988), vol. 332, pp. 323-327.
Vajdos et al., "Comprehensive Functional Maps of the Antigen-bining Site of an Anti-ErbB2 Antibody Obtained with Shotgun Scanning Mutagenesis," J. Mol. Biol. (2002), vol. 320, pp. 415-428.

(56) References Cited

OTHER PUBLICATIONS

"*Homo sapiens* cell cycle associated protein 1, mRNA (cDNA clone MGC:1378 Image:3355481), complete cds", Genebank database, NCBI Accession No. BC001731, Sep. 11, 2007.
Extended European Search Report for Appl. No. 13820574.5 dated Jan. 11, 2016.
Huang, J. et al, "IgG Isotype Conversion of a Novel Human Anti-carcinoembryonic Antigen Antibody to Increase its Biological Activity," Anticancer Research, 2006, vol. 26, No. 2A, pp. 1057-1063.
Japanese Office Action for Appl. No. 2014-225640 dated Nov. 4, 2015.
Shibaguchi, H. et al, "New Human Antibody IgG Subclass Conversion for Enhancement of Tumor-Cytotoxic Activity," Research, 2006, vol. 11, No. 3, pp. 15-16.
Carter, P. J., "Potent antibody therapeutics by design," Nature Reviews (May 2006), vol. 6, pp. 343-357.
Corada et al., "Monoclonal antibodies directed to different regions of vascular endothelial cadherin extracellular domain affect adhesion and clustering of the protein and modulate endothelial permeability," Blood (Mar. 15, 2001), vol. 97, No. 6, pp. 1679-1684.
Office Action dated Aug. 14, 2015, in U.S. Appl. No. 14/236,818.
Office Action dated Aug. 20, 2015, in U.S. Appl. No. 14/452,746.
Office Action dated Jul. 27, 2015, in Chinese Patent Application No. 201380038386.9.
Office Action dated Jul. 3, 2015, in Russian Patent Application No. 2012137503.
Office Action dated Sep. 15, 2015, in U.S. Appl. No. 14/389,266.
Padlan, E. A., "X-Ray Crystallography of Antibodies," Adv. Prot. Chem. (1996), vol. 49, pp. 57-133.
Saffari et al., "Identification of novel p53 target genes by cDNA AFLP in glioblastoma cells", Cancer Letters, 2009, No. 273, pp. 316-322.
Russian Decision on Grant for Russian Application No. 2012137504/10, dated Jun. 22, 2016, with an English translation.
Russian Office Action for Russian Application No. 2014138041/10, dated Jul. 5, 2016, with an English translation.
Non-Final Office Action dated May 19, 2016, in U.S. Appl. No. 14/415,090.
Non-Final Office Action dated May 19, 2016, in U.S. Appl. No. 14/415,520.
Decision on Grant of Patent for Invention dated May 16, 2016, in Russian Patent Application No. 2014108049, with English translation.
Russian Office Action and Search Report for Russian Application No. 2014143784, dated Jan. 19, 2017, including a partial English Translation.
Extended European Search Report dated Feb. 27, 2017, in European Patent Application No. 14834828.7.
Indian Examination Report dated Feb. 23, 2017, in Indian Patent Application No. 960/KOLNP/2011.
NCBI Reference Sequence:NP_005889 for human CAPRIN-1, printed Apr. 2017.
Russian Decision on Grant of Patent for Invention dated Mar. 13, 2017, in Russian Patent Application No. 2012137503, with English translation.
Russian Decision on Grant of Patent for Invention dated Mar. 29, 2017, in Russian Patent Application No. 2014108048, with English translation.
U.S. Non-Final Office Action dated Apr. 26, 2017, in U.S. Appl. No. 13/057,515.
GenBank Accession No. NM_005898, Feb. 11, 2008.
Office Action dated Sep. 28, 2014, in Chinese Patent Application No. 201280038464.0.
Roitt et al., "NK cells and K cells use several different receptors on the surface, to identify their targets," Immunology, 2000, p. 181 (4 pages), with an English abstract.
Russian Office Action and English translation thereof, dated Apr. 17, 2017, for Russian Application No. 2014143785/10.
U.S. Non-Final Office Action, dated May 15, 2017, for U.S. Appl. No. 15/092,469.
Extended European Search Report for European Application No. 13767612.8, dated Sep. 22, 2015.
Extended European Search Report for European Application No. 13769665.4 dated Sep. 22, 2015.

* cited by examiner

METHOD FOR DETECTING PANCREATIC CANCER

TECHNICAL FIELD

The present invention relates to a method for detecting pancreatic cancer using CAPRIN-1 as a tumor marker.

BACKGROUND ART

It is reported that there are over 10,000 patients with refractory pancreatic cancer in Japan, the occurrence thereof is increasing year after year, and it is assumed that the number of patients will continue to increase. Even if pancreatic cancer were surgically removed, small cancer cells have often infiltrated and metastasized to other organs. Accordingly, pancreatic cancer often relapses, and the 5-year survival rate is as low as 9%; that is, the prognosis of pancreatic cancer is very poor. For the purpose of preventing postoperative recurrence, Gemcitabine, an anticancer agent, has been employed. However, the primary purpose of Gemcitabine administration is pain relief, and tumor size reduction or survival advantage can hardly be expected. At some hospitals, another anti-cancer agent, TS-1, which is currently used for gastric cancer, is used, although it is difficult to expect any therapeutic effects.

In order to improve the prognosis for pancreatic cancer, early detection is important, as it is with other cancers; however, early detection is difficult because pancreatic cancer shows substantially no initial symptoms. To date, methods of detecting pancreatic cancer using carcinoembryonic antigen (CEA) and glycoproteins (CA19-9 and Dupan-2) in biological samples as tumor markers of pancreatic cancer have been actively employed. However, the levels of such tumor markers do not become elevated unless pancreatic cancer advances, and such markers occasionally show normal values in the progressive stage. Accordingly, such tumor markers are not considered to be sufficient for accurate detection of pancreatic cancer. In addition, most tumor markers that are currently known are present in very small amounts in the body fluids (at the pg/ml level). In order to detect such small amounts of markers, accordingly, detection techniques with high sensitivity or special techniques are necessary. Under such circumstances, a novel technique for detecting pancreatic cancer in a simple manner with high sensitivity is expected to be applicable to diagnosis of pancreatic cancer. It is necessary to undergo periodic thorough examinations in order to detect early-stage pancreatic cancer. Accordingly, a method of detecting cancer that can be carried out in a simple manner with the use of blood serum or urine samples without the imposition of physical or financial burdens on either healthy individuals without pancreatic cancer or patients with cancer has been awaited.

Also, pancreatic cancer is refractory in dogs. Although a lump can be observed in the abdominal region of a dog afflicted with pancreatic cancer, the major symptoms are rapid energy loss, unsteady gait, and gait abnormalities resulting from hypoglycemia. In most cases, the development of cancer would not be detected until such symptoms are observed. In addition, pancreatic cancer is often likely already to be in the advanced stage when such symptoms are observed. In addition to surgical removal of pancreatic cancer, accordingly, therapeutic techniques are limited to supportive therapy and administration of anticancer agents. As with the case of human patients, early detection is important for dogs afflicted with pancreatic cancer in order to effectively treat such pancreatic cancer. As with the case for humans, there were no diagnostic agents for dogs in the past that allowed detection of pancreatic cancer at the early stage in a simple manner. In the field of veterinary medicine, detection techniques such as radiographic techniques by means of X-rays, CT, or MRI have not yet become common. At present, detection is carried out by palpation, simple blood testing, and X-ray photography, and diagnosis is heavily dependent on the experience of veterinary doctors. If a simple means for cancer detection with high sensitivity that can be applied to diagnosis of pancreatic cancer in dogs is provided, adequate treatment can be performed, which has great advantages for dog owners and veterinary doctors.

Cytoplasmic- and proliferation-associated protein 1 (CAPRIN-1) is an intracellular protein that is expressed when normal cells in the resting phase are activated or undergo cell division. CAPRIN-1 is also known to be involved in the control of the transport and translation of mRNAs through formation of cytoplasmic stress granules and RNA in a cell. Also, genes encoding CAPRIN-1 proteins are demonstrated to be expressed specifically in canine and human testis and malignant tumor cells, FCM analysis of breast cancer cells with the use of antibodies against CAPRIN-1 demonstrates CAPRIN-1 expression on the surfaces of breast cancer cells, and immunohistochemical staining using breast cancer tissues demonstrates CAPRIN-1 expression at high level in breast cancer cells. In addition, it has been reported that the antibodies mentioned above would damage breast cancer cells through the functions of lymphocytes, and that antibodies against CAPRIN-1 exert potent antitumor effects in cancer-carrying mouse models into which breast cancer cells had been transplanted (Patent Literature 1). Also, it has been reported that cancers such as breast cancer could be diagnosed by measuring either antibodies induced in the body of a subject against CAPRIN-1 present in the blood serum or polypeptides that undergo antigen-antibody reactions with CAPRIN-1 (Patent Literature 2). Up to the present, however, there have been no reports of the fact that pancreatic cancer can be diagnosed by measuring either antibodies against CAPRIN-1 induced in the blood serum of a patient with pancreatic cancer or polypeptides that undergo antigen-antibody reactions with the CAPRIN-1.

PRIOR ART LITERATURES

Patent Literature

Patent Literature 1: International Publication No. WO 2010/016526

Patent Literature 2: International Publication No. WO 2010/016527

SUMMARY OF THE INVENTION

Problem to be Attained by the Invention

It is an object of the present invention to provide a means for detecting pancreatic cancer that is useful for diagnosis of pancreatic cancer.

Means for Solving the Problem

The present inventors have conducted concentrated studies. As a result, the present inventors have now found that pancreatic cancer can be diagnosed, examined, or detected on the basis of CAPRIN-1 expression in pancreatic cancer, measurement (or assay) of antibodies against CAPRIN-1 induced in the blood serum of a patient with pancreatic cancer with the use of a CAPRIN-1 protein, and binding of the antibodies produced with the use of such proteins to CAPRIN-1 in the pancreatic cancer tissue. This has led to the completion of the present invention.

Specifically, the present invention provides a method for detecting pancreatic cancer comprising measuring a CAPRIN-1 expression in a sample separated from a subject. The term "detecting" as used herein can be used interchangeably with the term "examining" or "evaluating." Also, the present invention provides a reagent or kit for detecting pancreatic cancer comprising a polypeptide that undergoes an antigen-antibody reaction with an antibody against CAPRIN-1 induced or elicited in the body of a subject. Further, the present invention provides a reagent or kit for detecting pancreatic cancer comprising an antibody that undergoes an antigen-antibody reaction with CAPRIN-1 or an antigen-binding fragment of the antibody. Furthermore, the present invention provides a reagent or kit for detecting pancreatic cancer comprising a polynucleotide hybridizing specifically to a partial sequence comprising at least 15 to 19 nucleotides or at least 20 to 30 nucleotides of the nucleotide sequence represented by any of SEQ ID NOs: 1, 3, 5, 7, 9, 11, 13, . . . , 29. The "reagent or kit for detecting pancreatic cancer" used herein can also be referred to as a "reagent or kit for pancreatic cancer detection."

Specifically, the present invention has the features described below.

(1) A method for detecting pancreatic cancer comprising measuring the presence or amount of a polypeptide having a reactivity of specifically binding to an antibody against a CAPRIN-1 protein via an antigen-antibody reaction, or the presence or amount of a nucleic acid encoding the polypeptide in a sample separated from a subject.

(2) The method according to (1), wherein the polypeptide to be measured is a CAPRIN-1 protein consisting of an amino acid sequence represented by any of the even-numbered SEQ ID NOs: 2 to 30 or a polypeptide consisting of an amino acid sequence having 85-90% or higher sequence identity with the CAPRIN-1 protein.

(3) The method according to (1) or (2), wherein the subject is a human or a dog.

(4) The method according to (3), wherein the subject is a dog and the polypeptide to be measured comprises an amino acid sequence represented by any of the even-numbered SEQ ID NOs: 2 to 30.

(5) The method according to (4), wherein the subject is a dog and the polypeptide to be measured comprises the amino acid sequence represented by SEQ ID NO: 6, 8, 10, 12, or 14.

(6) The method according to (3), wherein the subject is a human and the polypeptide to be measured comprises the amino acid sequence represented by SEQ ID NO: 2 or 4.

(7) The method according to any of (1) to (6), wherein the presence or amount of the polypeptide is determined by immunologically measuring an antibody induced against the polypeptide to be measured in the body of a subject, which can be contained in the sample.

(8) The method according to any of (1) to (6), wherein the presence or amount of a nucleic acid encoding the polypeptide is determined by measuring a nucleic acid encoding such polypeptide contained in the sample.

(9) The method according to (8), wherein the presence or amount of the nucleic acid in the sample is measured using a polynucleotide specifically hybridizing to a partial sequence comprising at least 15 to 19 nucleotides, preferably at least 20 to 25 nucleotides, and more preferably at least 30 nucleotides of the nucleotide sequence in the nucleic acid or a sequence complementary thereto.

(10) The method according to (9), wherein the subject is a dog and the polynucleotide specifically hybridizes to a partial sequence comprising at least 15 to 19 nucleotides, preferably at least 20 to 25 nucleotides, and more preferably at least 30 nucleotides in the nucleotide sequence represented by SEQ ID NO: 5, 7, 9, 11, or 13 or a sequence complementary thereto.

(11) The method according to (9), wherein the subject is a human and the polynucleotide specifically hybridizes to a partial sequence comprising at least 15 to 19 nucleotides, preferably at least 20 to 25 nucleotides, and more preferably at least 30 nucleotides in the nucleotide sequence represented by SEQ ID NO: 1 or 3 or a sequence complementary thereto.

(12) The method according to any of (1) to (6), wherein the presence or amount of the polypeptide is determined by measuring the polypeptide contained in the sample.

(13) The method according to (12), wherein the assay is an immunological assay.

(14) The method according to any of (1) to (13), wherein the sample is blood, serum, blood plasma, ascites fluid, pleural effusion, tissues, or cells.

(15) A reagent or kit for detecting pancreatic cancer comprising one or more polypeptides having a reactivity of binding via an antigen-antibody reaction to an antibody induced against a CAPRIN-1 protein in the body of a subject.

(16) A reagent or kit for detecting pancreatic cancer comprising one or more antibodies that undergo an antigen-antibody reaction with a polypeptide having a reactivity of binding via an antigen-antibody reaction to an antibody against a CAPRIN-1 protein and produced in the body of a subject or to an antigen-binding fragment of the antibody.

(17) The reagent or kit according to (15) or (16), wherein the CAPRIN-1 protein has an amino acid sequence represented by any of the even-numbered SEQ ID NOs: 2 to 30.

(18) The reagent or kit according to (16) or (17), wherein the antibody or an antigen-binding fragment thereof that undergoes an antigen-antibody reaction with the polypeptide is an antibody or an antigen-binding fragment thereof that binds to the surface of a pancreatic cancer cell.

(19) The reagent or kit according to any of (16) to (18), wherein the antibody or an antigen-binding fragment thereof that undergoes an antigen-antibody reaction with the polypeptide comprises an antibody or a fragment thereof having an immunological reactivity with a polypeptide consisting of an amino acid sequence comprising at least 7 to 12 continuous amino acid residues within the region of amino acid residue Nos. 50 to 98 or amino acid residue Nos. 233 to 344 of the amino acid sequence represented by any of the even-numbered SEQ IDS NO: 2 to 30 except for SEQ ID NOs: 6 and 18 or with a polypeptide comprising the polypeptide as a partial sequence.

(20) The reagent or kit according to any of (16) to (19), wherein the antibody or an antigen-binding fragment that undergoes an antigen-antibody reaction with the polypeptide is one or more antibodies selected from the group consisting of: an antibody binding to a polypeptide comprising the amino acid sequence represented by SEQ ID NO: 43 or antigen-binding fragment thereof; a monoclonal antibody comprising the amino acid sequences represented by SEQ ID NOs: 44 and 45 or an antigen-binding fragment thereof; a monoclonal antibody comprising the amino acid sequences represented by SEQ ID NOs: 44 and 46 or an antigen-binding fragment of each thereof; a monoclonal antibody comprising the amino acid sequences represented by SEQ ID NOs: 44 and 47 or an antigen-binding fragment thereof; a monoclonal antibody comprising the amino acid sequences represented by SEQ ID NOs: 44 and 48 or an antigen-binding fragment thereof; a monoclonal antibody comprising the amino acid sequences represented by SEQ ID NOs: 49 and 50 or an antigen-binding fragment thereof; a monoclonal antibody comprising the amino acid sequences represented by SEQ ID NOs: 51 and 52 or an antigen-binding fragment thereof; a monoclonal antibody comprising the amino acid sequences represented by SEQ ID NOs: 53 and 54 or an antigen-binding fragment thereof; a monoclonal antibody comprising the amino acid sequences represented by SEQ ID NOs: 55 and 56 or an antigen-binding fragment thereof; a monoclonal antibody comprising the amino acid sequences represented by SEQ ID NOs: 57 and 58 or an antigen-binding fragment thereof; and a monoclonal antibody comprising the amino acid sequences represented by SEQ ID NOs: 59 and 60 or an antigen-binding fragment thereof.

(21) A reagent or kit for detecting pancreatic cancer comprising one or more polynucleotides that specifically hybridize to a partial sequence comprising at least 15 to 19 nucleotides, preferably at least 20 to 25 nucleotides, and more preferably at least 30 nucleotides in the nucleotide sequence represented by any of the odd-numbered SEQ ID NOs: 1 to 29 and encoding a CAPRIN-1 protein or in a sequence complementary to the nucleotide sequence.

(22) A method for detecting pancreatic cancer comprising measuring the presence or amount of a CAPRIN-1 protein, an antibody against a CAPRIN-1 protein, or a nucleic acid encoding the CAPRIN-1 protein in a sample from a subject using at least one reagent or kit according to any of (15) to (21).

(23) The method for detecting pancreatic cancer according to any of (1) to (14), comprising measuring the presence or an amount of a CAPRIN-1 protein, an antibody against a CAPRIN-1 protein, or a nucleic acid encoding the CAPRIN-1 protein in a sample from a subject using at least one reagent or kit according to any one of (15) to (21).

According to the present invention, a novel method for detecting pancreatic cancer is provided. As specifically described in the examples below, a recombinant polypeptide prepared based on the amino acid sequence of CAPRIN-1 (or Caprin-1) is capable of specifically reacting with an antibody that exists in the serum of a patient with pancreatic cancer. As such, the pancreatic cancer existing in a subject can be detected by measuring the antibody in a sample by the method of the present invention. Also, pancreatic cancer existing in a subject can be detected by measuring (or assaying) CAPRIN-1 itself. As described in the examples below, in addition, high levels of CAPRIN-1 gene expression are observed specifically in testis and pancreatic cancer cells of subjects (hereinafter, such expression product is occasionally referred to as a "nucleic acid encoding a CAPRIN-1 (protein)"). Therefore, pancreatic cancer can also be detected by measuring a nucleic acid. Further, the presence or amount of CAPRIN-1 (expression) in the pancreatic cancer tissue can be measured with the use of an antibody against CAPRIN-1. Patients with pancreatic cancer may be subjected to such measurement in advance, so that the patients to whom a CAPRIN-1-targeted therapeutic agent (e.g., antibody medicine) is applicable can be selected.

EMBODIMENTS FOR CARRYING OUT THE INVENTION

According to the method of the present invention, the presence or an amount of CAPRIN-1 (expression) is measured using a sample separated from a subject. Examples of methods for measuring the presence or an amount of CAPRIN-1 (expression) include: a method for immunologically measuring an antibody against CAPRIN-1 contained in a sample (the first method); a method for immunologically measuring CAPRIN-1 itself contained in a sample (the second method); and a method for measuring a nucleic acid encoding CAPRIN-1 contained in a sample, such as mRNA or cDNA synthesized from mRNA (the third method). In the present invention, the presence or an amount of CAPRIN-1 (expression) may be measured by any of the above methods. In the present invention, the term "measuring" is intended to include any of the following meaning: detecting, qualitatively measuring, quantitatively measuring, and semi-quantitatively measuring.

The amino acid sequence represented by SEQ ID NOs: 6, 8, 10, 12, or 14 is an amino acid sequence of canine CAPRIN-1. Canine CAPRIN-1 having such an amino acid sequence has been identified as a polypeptide binding to an antibody specifically existing in the serum derived from a cancer-bearing dog (see Example 1). An antibody against CAPRIN-1 having the amino acid sequence represented by SEQ ID NO: 6, 8, 10, 12, or 14 is specifically induced or elicited in the body of a cancer-bearing dog. Specifically, canine pancreatic cancer can be detected by measuring the above antibody against CAPRIN-1 having the amino acid sequence represented by SEQ ID NO: 6, 8, 10, 12, or 14 by the first method. Also, canine pancreatic cancer can be detected by measuring CAPRIN-1 itself as an antigen having the amino acid sequence represented by SEQ ID NO: 6, 8, 10, 12, or 14 by the second method. Since the CAPRIN-1 gene is expressed at significantly high levels in pancreatic cancer cells, canine pancreatic cancer can be detected by measuring the nucleic acid in accordance with the third method.

The term "having an amino acid sequence" used herein refers to amino acid residues aligned in a given order. Therefore, for example, the expression "polypeptide having the amino acid sequence represented by SEQ ID NO: 2" refers to a polypeptide having 709 amino acid residues, which consists of the amino acid sequence of Met Pro Ser Ala . . . (partially omitted) . . . Gln Gln Val Asn represented by SEQ ID NO: 2. Also, the expression "polypeptide having the amino acid sequence represented by SEQ ID NO: 2" may also be abbreviated as "the polypeptide of SEQ ID NO: 2," for example. The same applies to the expression "having a/nucleotide sequence." In this case, the term "having" may be substituted with the expression "comprising" or "consisting of."

Also, the term "polypeptide" used herein refers to a molecule that is formed via a peptide bond of a plurality of amino acids. Examples of such molecule include not only polypeptide molecules with large numbers of constituent amino acids, but also low-molecular-weight molecules (oligopeptides) with small numbers of amino acids and full-length proteins. The present invention further encompasses full-length CAPRIN-1 proteins each having an amino acid sequence represented by any of the even-numbered SEQ ID NOs: 2 to 30 (i.e., SEQ ID NOs: 2, 4, 6, . . . 26, 28, and 30).

The term "subject" used herein refers to vertebrates, including mammals and birds, preferably mammals, and more preferably humans, dogs, cows, and horses.

The term "sample" used herein refers to a biological sample subjected to examination aimed at detection of pancreatic cancer. Examples of the sample include body fluids, tissues, and cells separated from a subject. Examples of body fluids include, but are not limited to, blood, serum, blood plasma, ascites fluid, and pleural effusion. Tissues or cells of the pancreas that is suspected of being afflicted with cancer are within the scope of the "sample."

In the method of the present invention, the targets to be measured are to not only canine CAPRIN-1 of SEQ ID NO: 6, 8, 10, 12, or 14, but also CAPRIN-1 of other mammals (hereinafter, which may also be referred to as a "homolog" (or "ortholog") for canine CAPRIN-1). When it is simply referred to as "CAPRIN-1," CAPRIN-1 from another mammal, including a human, is also a target to be measured, in addition to CAPRIN-1 from a dog. As specifically described in the examples below, the human CAPRIN-1 gene expression level is significantly high in human pancreatic cancer cells, whereas no antibody against human CAPRIN-1 gene is detected in a healthy human body. As such, pancreatic cancer of a mammal other than a dog can be detected by measuring CAPRIN-1 expression in the mammal. An example of CAPRIN-1 of a mammal other than a dog to be measured by the method of the present invention is, but is not limited to, human CAPRIN-1. Nucleotide sequences encoding human CAPRIN-1 and amino acid sequences therefor are represented by SEQ ID NOs: 1 and 3 and SEQ ID NOs: 2 and 4 in the Sequence Listing. Sequence identity between human CAPRIN-1 and canine CAPRIN-1 is 94% for nucleotide sequence and is 98% for amino acid sequence. The sequence identity of the amino acid sequences of CAPRIN-1 is as high as 98% between genetically distant mammals, such as a dog and a human. Therefore, it is considered that the sequence identity is about 85% or higher between a dog and a mammal other than a human; that is, canine CAPRIN-1 and its homolog. CAPRIN-1, the expression of which is to be measured by the method of the present invention, preferably has 85% or higher, more preferably 90% or higher, and further preferably 95% or higher sequence identity with the amino acid sequence of canine CAPRIN-1 represented by SEQ ID NO: 6, 8, 10, 12, or 14, although the sequence identities are not limited thereto.

In the first method, the antibody that can be present in a sample can be easily measured by immunoassay using an antigenic substance that undergoes an antigen-antibody reaction with the antibody. Immunoassay itself is a well-known conventional method as specifically described below. As an antigenic substance for immunoassay, for example, the canine CAPRIN-1 protein of SEQ ID NO: 6, 8, 10, 12, or 14 that induces the antibody within the body of a cancer-bearing dog or a fragment containing an epitope of such protein can be used. Further, the antibody has a cross-reactivity. A molecule other than an antigenic substance that actually serves as an immunogen can also bind, via an antigen-antibody reaction, to an antibody induced against an immunogen, as long as the molecule has a structure analogous to an epitope of the immunogen. Between a protein from a certain type of mammal and a homolog thereof from another mammal, in particular, the identity of their amino acid sequences is high, and epitope structures are often analogous to each other. As specifically described in the examples below, the canine CAPRIN-1 of SEQ ID NO: 6, 8, 10, 12, or 14 undergoes an antigen-antibody reaction with an antibody induced against the canine CAPRIN-1 within the body of a cancer-bearing dog. Also, human CAPRIN-1 undergoes an antigen-antibody reaction with the antibody induced within the body of a cancer-bearing dog. Accordingly, CAPRIN-1 from any mammal can be used as an antigen for immunoassay in accordance with the first method of the present invention.

When an antigenic substance is a protein or the like having a complicated structure and a high molecular weight, in general, a plurality of sites having different structures are present on the molecule. Therefore, a plurality of types of antibodies capable of recognizing and binding to different sites of such antigenic substances are produced in the body of a subject. Specifically, an antibody that is produced in the subject against an antigenic substance such as a protein is a polyclonal antibody that is a mixture of a plurality of types of antibodies. An antibody now found by the present inventors is also a polyclonal antibody that is specifically present in the serum obtained from a cancer-bearing subject and specifically binds, via an antigen-antibody reaction, to a recombinant CAPRIN-1 protein. The term "polyclonal antibody" used in the present invention refers to an antibody that exists in the serum obtained from a subject containing an antigenic substance and is induced against such antigenic substance.

In the examples below, polypeptides of SEQ ID NO: 6 and SEQ ID NO: 8 (both, canine CAPRIN-1) and the polypeptide of SEQ ID NO: 2 (human CAPRIN-1) were prepared as antigens for immunoassay of specific antibodies in cancer-bearing living animals. The reactivity between these polypeptides and the antibodies in the serum obtained from a cancer-bearing subject was then confirmed. However, the antibodies mentioned above are polyclonal antibodies, and they naturally bind to polypeptides consisting of homologs of SEQ ID NO: 6, 8, and 2. Even in the case of a fragment of such a polypeptide, it can bind to an antibody contained in the serum obtained from a cancer-bearing subject since some polyclonal antibodies are capable of recognizing the structure of the fragment. That is, both the polypeptide (that is, the full-length CAPRIN-1 protein) of the homolog of SEQ ID NO: 6, 8, or 2 and a fragment thereof can be similarly used for assay of a polyclonal antibody contained specifically in the serum of a cancer-bearing subject, and they are useful for cancer detection. Accordingly, a polypeptide to be used as an antigen for immunoassay in the first method of the present invention is not limited to a polypeptide alone consisting of the full-length region of a CAPRIN-1 protein (e.g., SEQ ID NO: 6, 8, or 2). It can be a polypeptide fragment consisting of at least 7 to 12, and preferably at least 8, 9, or 10 continuous amino acids of the amino acid sequence of a CAPRIN-1 protein that undergoes an antigen-antibody reaction with a polyclonal antibody against the CAPRIN-1 protein (hereinafter, it may be referred to as a "specifically reactive partial polypeptide" for convenience). It is known in the art that a polypeptide comprising about 7 to 12 or more amino acid residues can exert antigenicity. If the number of amino acid residues is too low, however, such polypeptide is highly likely to cross-react with an antibody against a protein other than the CAPRIN-1 protein that exists in the sample. In view of enhancing the accuracy of immunoassay, accordingly, the number of amino acid residues of a polypeptide fragment is preferably 20 or more, 30 or more, and 50 or more, more preferably 100 or more or 150 or more, further preferably 300 or more, and even further preferably 600 or more. The number of amino acid residues may be 1,000 or more, or 1,500 or more.

Preferable examples of the polypeptides to be used as antigens include the polypeptides of the even-numbered SEQ ID NOs: 2 to 30 or fragments thereof comprising epitopes (e.g., a polypeptide fragment comprising about 7 to 12 or more amino acid residues).

Nucleotide sequences of polynucleotides encoding proteins consisting of the amino acid sequences of the even-numbered SEQ ID NOs: 2 to 30 (i.e., SEQ ID NOs: 2, 4, 6 . . . 28, and 30) are represented by the odd-numbered SEQ ID NOs: 1 to 29 (i.e., SEQ ID NOs: 1, 3, 5 . . . 27, and 29).

In general, it is well known in the art that protein antigens retain antigenicity almost equivalent to that of the original protein even if a small number of amino acid residues have been substituted, deleted, added, or inserted in the amino acid sequence of the protein. Therefore, a polypeptide having a sequence derive from the amino acid sequence of a CAPRIN-1 protein by substitution, deletion, and/or insertion of a small number of (preferably one or several amino acid residues, having 80% or higher, 85-90% or higher, preferably 90% or higher, more preferably 95% or higher, further preferably 98% or higher, and still further preferably 99% or higher sequence identity with the original sequence, and specifically binding via an antigen-antibody reaction to an antibody against CAPRIN-1 (hereinafter, the same may be referred to as a "specifically reactive modified polypeptide" for convenience) can be used for cancer detection in a manner similar to the case of the polypeptides described above. Preferably, a specifically reactive modified polypeptide has an amino acid sequence derived from the amino acid sequence of a CAPRIN-1 protein by substitution, deletion, and/or insertion of one or several amino acid residues. The term "several" used herein refers to an integer of 2 to 10, preferably an integer of 2 to 6, and further preferably an integer of 2 to 4.

The term "sequence identity" used herein with reference to amino acid sequences is determined by aligning two amino acid sequences to be compared, so that as many amino acid residues match as possible, dividing the number of amino acid residues that match by the total number of amino acid residues, and then expressing the results in percentage terms (%). Upon the above alignment, gaps are inserted as appropriate into one or both of the sequences to be compared, according to need. Such sequence alignment can be performed using a well-known program or algorism, such as BLAST, FASTA, or CLUSTAL W (Karlin and Altschul, Proc. Natl. Acad. Sci. U.S.A., 87: 2264-2268, 1993; Altschul et al., Nucleic Acids Res., 25: 3389-3402, 1997).

Twenty types of amino acids constituting naturally occurring proteins can be divided into groups of amino acids having properties analogous to each other: neutral amino acids having side chains with low polarity (Gly, Ile, Val, Leu, Ala, Met, and Pro); neutral amino acids having hydrophilic side chains (Asn, Gln, Thr, Ser, Tyr, and Cys); acidic amino acids (Asp and Glu); basic amino acids (Arg, Lys, and His); and aromatic amino acids (Phe, Tyr, Trp, and His). It is known that substitution among these amino acids (that is, conservative substitution) rarely alters the properties of the resulting polypeptide. When amino acid residues of CAPRIN-1 are to be substituted, accordingly, substitution is performed between members of the same group, so that the possibility of maintaining binding with the corresponding antibody becomes higher. In the present invention, however, the above variant may involve non-conservative substitution, as long as immunity-inducing activity equivalent to or almost equivalent to that of an unmodified polypeptide is imparted.

A polypeptide (hereinafter, which may be referred to as a "specifically reactive addition polypeptide" for convenience) that contains, as a partial sequence, the above polypeptide to be used in the present invention (e.g., prepared by addition of another (poly)peptide to one end or both ends of a polypeptide to be used in the present invention) and specifically binds via an antigen-antibody reaction to an antibody against CAPRIN-1 can also be used for detection of pancreatic cancer in a manner similar to the cases of the above polypeptides.

The polypeptides used in the present invention can be synthesized in accordance with a chemical synthesis method such as the Fmoc method (the fluorenylmethyloxycarbonyl method) or the tBoc method (the t-butyloxy-carbonyl method) (the Japanese Biochemical Society (ed.), Seikagaku Jikken Koza (Biochemical Experimental Lecture Series) 1, Tanpakushitsu no Kagaku (Protein Chemistry) IV, Kagaku Shushoku to Peptide Gousei (Chemical Modification and Peptide Synthesis), TOKYO KAGAKU DOZIN CO., LTD, Japan, 1981). Also, the polypeptides can be synthesized by a conventional method using various commercially available peptide synthesizers. Alternatively, the polypeptides can be easily prepared by known genetic engineering techniques (e.g., Sambrook et al., Molecular Cloning, 2nd Edition, Current Protocols in Molecular Biology, 1989, Cold Spring Harbor Laboratory Press; Ausubel et al., Short Protocols in Molecular Biology, 3rd Edition, A Compendium of Methods from Current Protocols in Molecular Biology, 1995, John Wiley & Sons). From RNA extracted from a tissue expressing a gene encoding the human CAPRIN-1 of SEQ ID NO: 2 or a homolog thereof, for example, cDNA of the gene is prepared via RT-PCR, the full-length sequence or a desired partial sequence of the cDNA is incorporated into an expression vector, and the vector is then introduced into a host cell. Thus, a polypeptide of interest can be obtained. The nucleotide sequences of cDNAs encoding canine CAPRIN-1 of SEQ ID NOs: 6, 8, 10, 12, and 14 are shown in SEQ ID NOs: 5, 7, 9, 11, and 13, respectively. The nucleotide sequences of human homologs thereof; that is, the cDNAs encoding human CAPRIN-1 of SEQ ID NOs: 2 and 4, are shown in SEQ ID NOs: 1 and 3, respectively. Accordingly, primers used for RT-PCR can be easily designed with reference to these nucleotide sequences. As described below, also, a gene encoding CAPRIN-1 of a non-human mammal can be amplified using primers designed with reference to the nucleotide sequences of the odd-numbered SEQ ID NOs: 1 to 29. Accordingly, cDNA encoding, for example, feline CAPRIN-1 can be easily prepared by techniques similar to the above techniques. RNA extraction, RT-PCR, incorporation of cDNA into a vector, and introduction of a vector into a host cell can be performed by, for example, well-known methods as described below. Also, vectors and host cells used herein are well known, and various vectors and host cells are commercially available.

The above host cells may be any cells, as long as they can express the above polypeptides. Examples of prokaryotic host cells include *Escherichia coli*. Examples of eukaryotic host cells include cultured mammalian cells, such as monkey kidney cells (COS1), Chinese hamster ovary cells (CHO), the human embryonic kidney cell line (HEK293), and the mouse embryonic skin cell line (NIH3T3), budding yeast, fission yeast, silkworm cells, and Xenopusoocytes.

When prokaryotic cells are used as host cells, an expression vector having a replication origin in prokaryotic cells, a promoter, a ribosome-binding site, a multi-cloning site, a terminator, a drug-resistance gene, an auxotrophic complementary gene, and the like is used. Examples of expression vectors for *Escherichia coli* include pUC vectors, pBluescriptII, pET expression systems, and pGEX expression systems. DNA encoding the above polypeptide is incorporated into such an expression vector, prokaryotic host cells are transformed with the vector, and the thus obtained transformant is cultured. Thus, the polypeptide encoded by the DNA can be expressed in the prokaryotic host cells. At this time, the polypeptide can also be expressed as a fusion protein with another protein. DNA encoding the above polypeptide can be obtained by preparing cDNA by, for example, RT-PCR, as described above. Alternatively, such DNA can be synthesized by a conventional technique using a commercially available nucleic acid synthesizer, as described below. The nucleotide sequences of cDNAs of the genes encoding CAPRIN-1 of SEQ ID NOs: 2 and 4 are shown in SEQ ID NOs: 1 and 3 in the Sequence Listing, respectively.

When eukaryotic cells are used as host cells, an expression vector for eukaryotic cells having a promoter, a splicing region, a poly(A) additional site, and the like is used. Examples of such an expression vector include pKA1, pCDM8, pSVK3, pMSG, pSVL, pBK-CMV, pBK-RSV, an EBV vector, pRS, pcDNA3, and pYES2. As described above, DNA encoding a polypeptide used in the present invention is incorporated into such an expression vector, eukaryotic host cells are transformed with the vector, and the thus obtained transformant is cultured. Thus, the polypeptide encoded by the above DNA can be expressed in eukaryotic host cells. When pIND/V5-His, pFLAG-CMV-2, pEGFP-N1, pEGFP-C1, or the like is used as an expression vector, the above polypeptide can be expressed as a fusion protein with various tags, such as His tags (e.g., $(His)_6$ to $(His)_{10}$), a FLAG tag, a myc tag, an HA tag, or GFP.

An expression vector can be introduced into a host cell in accordance with a well-known technique, such as electroporation, a calcium phosphate method, a liposome method, a DEAE dextran method, microinjection, viral infection, lipofection, or binding with a cell-membrane-permeable peptide.

A polypeptide of interest can be isolated and purified from host cells using known isolation techniques in combination. Examples of such techniques include treatment using a denaturing agent such as urea or a surfactant, ultrasonication, enzymatic digestion, salting-out, solvent fractionation and precipitation, dialysis, centrifugation, ultrafiltration, gel filtration, SDS-PAGE, isoelectric focusing, ion exchange chromatography, hydrophobic chromatography, affinity chromatography, and reverse phase chromatography.

Polypeptides obtained by the above methods include polypeptides in the form of fusion proteins with any other proteins. Examples of such fusion proteins include a fusion protein with glutathione-S-transferase (GST) and a fusion protein with a His tag. Polypeptides in the form of such fusion proteins are also within the scope of the above described specifically reactive addition polypeptides, and such polypeptides can be used for the first detection method of the present invention. Further, polypeptides expressed in transformed cells may occasionally be subjected to various types of modification within cells after translation. Such a post-translationally modified polypeptide can be used in the first detection method of the present invention, as long as it is capable of specifically binding, via an antigen-antibody reaction, to an antibody against a CAPRIN-1 protein. Examples of such post-translational modification include the removal of N-terminal methionine, N-terminal acetylation, glycosylation, limited proteolysis by intracellular protease, myristoylation, isoprenylation, and phosphorylation.

An antibody in a sample can be easily measured by immunoassay using the above polypeptide as an antigen. Immunoassay itself is well known in the art. Immunoassay is classified into the sandwich method, the competition method, the agglutination method, the Western blot method, and the like based on types of reactions. Also, immunoassay is classified based on labels into radioimmunoassay, fluorescence immunoassay, enzyme immunoassay, and biotin immunoassay, for example. Immunoassay of the above antibody can be performed using any of these methods. Sandwich ELISA or the agglutination method are preferably employed as an immunoassay technique for the above antibody in the method of the present invention, since the procedures of these methods are convenient and require no extensive apparatus and the like, although techniques are not limited thereto. When an enzyme is used as a label for an antibody, such enzyme is not particularly limited, as long as it satisfies conditions such that: the turnover number is high; it remains stable even if it is bound to an antibody; and it specifically causes the color development of the substrate. Enzymes that can be used for general enzyme immunoassay, such as peroxidase, β-galactosidase, alkaline phosphatase, glucose oxidase, acetylcholine esterase, glucose-6-phosphorylation dehydrogenase, and malic acid dehydrogenase, can be used. In addition, enzyme-inhibiting substances, coenzymes, and the like can be used. Binding of these enzymes with antibodies can be performed by known methods involving the use of a cross-linking agent, such as a maleimide compound, the biotin-(strept)avidin system, or the like. As a substrate, a known substance can be used depending on the type of an enzyme to be used. When peroxidase is used as an enzyme, for example, 3,3',5,5'-tetramethylbenzidine can be used. When alkaline phosphatase is used, for example, para-nitrophenol can be used. A radioisotope that is generally used for radioimmunoassay, such as $^{125}I$ or $^{3}H$, can be used. A fluorescent dye that is used for general fluorescent antibody techniques, such as fluorescence isothiocyanate (FITC), tetramethylrhodamine isothiocyanate (TRITC), or a cyanine fluorescence dye (e.g., Cy3 or Cy5), can be used.

There is no need to explain the above immunoassay techniques herein since these techniques are well known; however, briefly, for example, the sandwich method comprises immobilizing the above polypeptide used as an antigen on a solid phase, allowing the polypeptide to react with a sample such as serum, washing, allowing an appropriate secondary antibody to react with an antibody from the sample, again washing, and then measuring the secondary antibody bound to the solid phase. By immobilizing an antigenic polypeptide on a solid phase, an unbound secondary antibody can be easily removed. Accordingly, it is preferable as an embodiment of the method for detecting cancer of the present invention. As a secondary antibody, an anti-canine IgG antibody, for example, can be used if a sample is from a dog. A secondary antibody is labeled in advance with a labeling substance exemplified above, so that the secondary antibody bound to a solid phase can be measured. The amount of the secondary antibody thus measured corresponds to the amount of the above antibody in the serum sample. When an enzyme is used as a labeling substance, the amount of the antibody can be measured by adding a substrate that is degraded in order to develop color by enzymatic action and then optically measuring the amount of the substrate degraded. When a radioisotope is used as a labeling substance, the amount of radiation from the radioisotope can be measured using a scintillation counter or the like.

In the second method of the present invention, CAPRIN-1 that can be contained in a sample obtained from a subject is measured. As described above, the amount of an antibody that undergoes an antigen-antibody reaction with CAPRIN-1 of a dog, a human, or the like is significantly higher in subjects with pancreatic cancer, compared with healthy subjects. This indicates that the amount of CAPRIN-1 accumulated as an antigen is significantly high in pancreatic cancer cells. In the case of healthy subjects, the CAPRIN-1 expression level is below the detection limit, or CAPRIN-1 expression in tissue is weak and it might occur merely within cells. Pancreatic cancer can also be detected by directly measuring CAPRIN-1, as specifically described in the examples below. Therefore, pancreatic cancer can be detected in a subject by measuring CAPRIN-1 itself, as in the case of the first method.

A polypeptide in a sample can be easily measured by well-known immunoassay techniques. Specifically, an antibody that undergoes an antigen-antibody reaction with CAPRIN-1 or an antigen-binding fragment thereof is prepared, and immunoassay is carried out using the same. Thus, the presence of CAPRIN-1 in the sample can be measured. As described above, an antibody has cross-reactivity. With the use of an antibody that undergoes an antigen-antibody reaction with canine CAPRIN-1 of SEQ ID NO: 6 or an antigen-binding fragment thereof, accordingly, not only the canine CAPRIN-1 of SEQ ID NO: 6, but also its homologs in other mammals (e.g., the human CAPRIN-1 of SEQ ID NO: 2 or 4) can be measured. The immunoassay technique itself is a well-known conventional technique, as described above.

This study reveals that CAPRIN-1 is a cell membrane protein that is expressed on the surface of pancreatic cancer cells. A subject with cancer contains many proteases in cancer tissues. Accordingly, the portion of the CAPRIN-1 sequence expressed outside the cancer cells is degraded and separated from the cancer cells, and such portion is larger in amount than the portion of the CAPRIN-1 sequence expressed in the cancer cells. If an antibody capable of binding to the surfaces of pancreatic cancer cells is used as an antibody against CAPRIN-1 in the measurement, or if an antigen-binding fragment thereof is used, accordingly, a larger amount of CAPRIN-1 can be detected, and pancreatic cancer can be diagnosed with higher sensitivity.

In the present invention, accordingly, use of an antibody that binds to a portion expressed on the surface of a pancreatic cancer cell of a CAPRIN-1 protein molecule is preferable. An example of a partial peptide of a CAPRIN-1 protein expressed on the surface of a pancreatic cancer cell is a polypeptide consisting of an amino acid sequence of 7 to 12 or more continuous amino acid residues within the region of amino acid residues (aa) 50 to 98 or amino acid residues (aa) 233 to 305 in any of the amino acid sequences represented by even-numbered SEQ ID NOs: 2 to 30 in the Sequence Listing, excluding SEQ ID NO: 6 and SEQ ID NO: 18. A specific example thereof is, but is not limited to, the amino acid sequence represented by SEQ ID NO: 43 or SEQ ID NO: 61 (in the amino acid sequence represented by SEQ ID NO: 61, a region of the amino acid sequence represented by SEQ ID NO: 62 or SEQ ID NO: 63 is preferable) or an amino acid sequence having 80% or higher, preferably 85% or higher, more preferably 90% or higher, and further preferably 95% or higher sequence identity with the relevant amino acid sequence. In addition, all antibodies binding to these polypeptides fall within the scope of the antibodies used in the present invention. Specific examples include an antibody binding to a polypeptide comprising the amino acid sequence represented by SEQ ID NO: 43 or antigen-binding fragment thereof, a monoclonal antibody having the amino acid sequences represented by SEQ ID NOs: 44 and 45 or an antigen-binding fragment thereof, a monoclonal antibody having the amino acid sequences represented by SEQ ID NOs: 44 and 46 or an antigen-binding fragment thereof, a monoclonal antibody having the amino acid sequences represented by SEQ ID NOs: 44 and 47 or an antigen-binding fragment thereof, a monoclonal antibody having the amino acid sequences represented by SEQ ID NOs: 44 and 48 or an antigen-binding fragment thereof, a monoclonal antibody having the amino acid sequences represented by SEQ ID NOs: 49 and 50 or an antigen-binding fragment thereof, a monoclonal antibody having the amino acid sequences represented by SEQ ID NOs: 51 and 52 or an antigen-binding fragment thereof, a monoclonal antibody having the amino acid sequences represented by SEQ ID NOs: 53 and 54 or an antigen-binding fragment thereof, a monoclonal antibody having the amino acid sequences represented by SEQ ID NOs: 55 and 56 or an antigen-binding fragment thereof, a monoclonal antibody having the amino acid sequences represented by SEQ ID NOs: 57 and 58 or an antigen-binding fragment thereof, and a monoclonal antibody having the amino acid sequences represented by SEQ ID NOs: 59 and 60 or an antigen-binding fragment thereof.

The term "antigen-binding fragment" used herein refers to an antibody fragment capable of binding to an antigen, such as an Fab fragment, an $F(ab')_2$ fragment, or an Fv fragment, contained in an antibody molecule. An antibody may be a polyclonal antibody or a monoclonal antibody. For immunoassay, a monoclonal antibody with high reproducibility is preferable. Methods for preparing a polyclonal antibody and a monoclonal antibody using a polypeptide as an immunogen are well known and can be easily performed in a conventional manner. For example, an animal is immunized with CAPRIN-1 or a fragment thereof alone or CAPRIN-1 or a fragment thereof bound to a carrier protein, such as keyhole limpet hemocyanin (KLH), casein, or serum albumin, as an immunogen, together with an adjuvant, and an antibody against CAPRIN-1 can then be induced. Antibody-producing cells, such as splenocytes or lymphocytes, collected from the immunized animal are fused to myeloma cells to prepare hybridomas, and hybridomas producing an antibody that binds to CAPRIN-1 are selected and then grown. Thus, a monoclonal antibody whose corresponding antigen is CAPRIN-1 can be obtained from the culture supernatant. The method described above is a well-known conventional method.

In the third method of the present invention, a nucleic acid encoding CAPRIN-1 (e.g., mRNA or cDNA synthesized from mRNA) that can be contained in a sample obtained from a living organism is measured. As specifically described in the examples below, a nucleic acid encoding the canine CAPRIN-1 of SEQ ID NO: 6, 8, 10, 12, or 14 or human CAPRIN-1 of SEQ ID NO: 2 or 4 is expressed at a significantly high level in pancreatic cancer cells. Therefore, a cancer existing in the living body can be detected by measuring such nucleic acid in a sample.

mRNA in a sample can be quantitatively measured by, for example, a conventional method, such as real-time detection RT-PCR using the mRNA as a template. Such mRNA can generally be quantitatively measured based on staining intensity or the like in the conventional Northern blot method. The cDNA sequences encoding CAPRIN-1 of the even-numbered SEQ ID NOs: 2 to 30 are represented by the odd-numbered SEQ ID NOs: 1 to 29, respectively. Accordingly, a polynucleotide specifically hybridizing to a partial region in the nucleotide sequence represented by any of the odd-numbered SEQ ID NOs: 1 to 29 (hereinafter, referred to as a "polynucleotide for cancer detection") is prepared based on these sequences, and such polynucleotide is used as a probe or a primer for nucleic acid amplification to determine the amount of the mRNA in a sample. If a polynucleotide is capable of specifically hybridizing to a partial region in the nucleotide sequence represented by any of the odd-numbered SEQ ID NOs: 1 to 29, mRNA encoding CAPRIN-1 in mammals other than dogs and humans can also be measured, as described later. In the present invention, a polynucleotide may be RNA or DNA.

The term "specifically hybridizing to" used herein refers to a situation in which said polynucleotide hybridizes only to a target partial region and does not substantially hybridize to any other regions under stringent hybridization conditions.

The term "under stringent hybridization conditions" used herein refers to conditions employed for annealing in general PCR or detection using a probe. In the case of PCR using Taq polymerase, for example, a reaction is performed at an appropriate annealing temperature ranging from about 54° C. to 60° C. using a general buffer, such as a buffer containing 50 mM KCl, 10 mM Tris-HCl (pH 8.3 to 9.0), and 1.5 mM $MgCl_2$. In the case of Northern hybridization, for example, a reaction is performed using a general hybridization solution such as 5×SSPE, 50% formamide, 5×Denhardt's solution, and 0.1-0.5% SDS, or 0.1-5×SSC and 0.1-0.5% SDS at an appropriate hybridization temperature ranging from about 42-65° C. After hybridization, washing is performed with, for example, 0.1-0.2×SSC and 0.1% SDS. Appropriate annealing temperatures or hybridization temperatures are not limited to the above examples, and such temperatures are determined based on the Tm value for a polynucleotide for cancer detection that is used as a primer or a probe and the empirical rules of experimenters. A person skilled in the art can easily determine such temperature range.

The expression "does not substantially hybridize to" used herein refers to a situation in which said polynucleotide does not hybridize to a target partial region at all or a extremely low amount of the polynucleotide hybridizes to a target partial region, that is, in a relatively negligible amount, even when it hybridizes to a target partial region. An example of the polynucleotide specifically hybridizing under such conditions is a polynucleotide having a certain level or higher of a sequence identity with the nucleotide sequence of a target partial region. For example, such polynucleotide has 70% or higher, preferably 80% or higher, more preferably 85% or higher, further preferably 90% or higher, even further preferably 93% or higher, still further preferably 95% or higher, and particularly preferably 98% or higher sequence identity. Most preferably, the polynucleotide has a nucleotide sequence identical to the nucleotide sequence of a target partial region. Sequence identity is defined in the same manner as the sequence identity of the amino acid sequence described above. Even if a terminus of a polynucleotide for cancer detection contains a region that does not hybridize thereto, in the case of a probe, it can be used for detection as long as a hybridizing region occupies about a half or more of the entire probe. In the case of a primer, it can be used for detection as long as a hybridizing region occupies about a half or more of the entire primer and is located on the 3' terminal side, since this allows a normal annealing and extension reaction to take place. When a terminus of a polynucleotide for cancer detection contains a non-hybridizing region, as described above, sequence identity with a target nucleotide sequence is calculated focusing only on the hybridizing region without taking a non-hybridizing region into consideration.

In the present invention, the term "partial sequence" (or "partial region") refers to a part of a nucleotide sequence represented by any of the odd-numbered SEQ ID NOs: 1 to 29. Specifically, the partial sequence comprises at least 15 to 19 continuous nucleotides, preferably 18 or more continuous nucleotides, more preferably at least 20 or 25 continuous nucleotides, and further preferably at least 30, 40, or 50 continuous nucleotides. The expression "the nucleotide sequence represented by SEQ ID NO: 5" used herein refers to, in addition to the nucleotide sequence actually shown in SEQ ID NO: 5, a sequence complementary thereto. Accordingly, the expression "a polynucleotide having the nucleotide sequence represented by SEQ ID NO: 5" refers to, for example, a single-stranded polynucleotide having the nucleotide sequence actually represented by SEQ ID NO: 5, a single-stranded polynucleotide having a nucleotide sequence complementary to the nucleotide sequence represented by SEQ ID NO: 5, or a double-stranded polynucleotide consisting of the two single-stranded polynucleotides. When a polynucleotide to be used in the present invention is prepared or a polynucleotide encoding a polypeptide to be used in the present invention is prepared, any of the nucleotide sequences is appropriately selected, and a person skilled in the art can readily perform such selection.

The number of nucleotides in a polynucleotide for cancer detection is preferably 18 or more in view of ensuring specificity. When the polynucleotide is used as a probe, it preferably comprises 18 or more nucleotides, and it further preferably comprises from 20 nucleotides to the full length of the coding region. When the polynucleotide is used as a primer, it preferably comprises 18 to 50 nucleotides. A preferable example of the polynucleotide for cancer detection is a polynucleotide comprising 18 or more continuous nucleotides in a nucleotide sequence represented by any of the odd-numbered SEQ ID NOs: 1 to 29.

It is apparent to a person skilled in the art who refers to the description of the present invention that: a polynucleotide specifically hybridizing to a partial region in SEQ ID NO: 5, 7, 9, 11, or 13 is used for measuring the amount of a nucleic acid (e.g., mRNA or cDNA synthesized from mRNA) encoding the canine CAPRIN-1 protein of SEQ ID NO: 6, 8, 10, 12, or 14, respectively; and a polynucleotide specifically hybridizing to a partial region in SEQ ID NO: 1 or 3 is used for measuring the amount of a nucleic acid (e.g., mRNA or cDNA synthesized from mRNA) encoding the human CAPRIN-1 protein of SEQ ID NO: 2 or 4, respectively. However, a protein from a given mammal and a homolog thereof from another mammal generally share a high sequence identity even at the nucleotide sequence level. Thus, the sequence identity among the nucleotide sequences of SEQ ID NOs: 1 to 13 is also as high as 94% to 100%. Accordingly, a polynucleotide specifically hybridizing to a partial region of the sequence of SEQ ID NO: 5 can also specifically hybridize to a partial region corresponding to the partial region of any of the odd-numbered SEQ ID NOs: 1 to 29.

In fact, a pair of primers having the nucleotide sequences represented by SEQ ID NO: 33 and 34 specifically hybridize to both a partial region of any of the odd-numbered SEQ ID NOs: 1 to 29 and a partial region of the sequence of SEQ ID NO: 5, as described in the examples below. Thus, both mRNA encoding the canine CAPRIN-1 of SEQ ID NO: 6 and mRNA encoding a homolog thereof can be measured. With the use of a polynucleotide specifically hybridizing to a partial region of the sequence of SEQ ID NO: 5, accordingly, not only mRNA encoding the canine CAPRIN-1 of SEQ ID NO: 6 but also mRNA encoding the human CAPRIN-1 of SEQ ID NO: 2 or 4 can be measured. Similarly, mRNA encoding CAPRIN-1 of another mammal such as a cat can also be measured. When a polynucleotide for cancer detection is designed, it is more desirable to select partial regions having particularly high sequence identity from among the odd-numbered SEQ ID NOs: 1 to 29 (and identical nucleotide sequences are preferable). If there is a particularly high sequence identity having partial region between canine CAPRIN-1 and human CAPRIN-1, a region showing very high sequence identity with such region is expected to be also present in a homolog gene of another animal species. Through selection of such a partial region, accuracy for measuring mRNA encoding CAPRIN-1 of an animal species other than dogs or humans can be increased.

A method for measuring a nucleic acid in test object using a polynucleotide specifically hybridizing to a partial region of the nucleic acid as a probe or a primer(s) for nucleic acid amplification method such as PCR is well known. Examples of such method include, in addition to RT-PCR as specifically described in the examples below, Northern blot and in situ hybridization. When the amount of mRNA is measured in the present invention, any such well-known measurement method can be employed.

A nucleic acid amplification method such as PCR is well known in the art, and reagent kits and apparatuses used therefor are commercially available, so that the method can be easily performed. Specifically, denaturation, annealing, and extension steps are each performed using a nucleic acid in test object (e.g., the cDNA of a gene encoding a protein having an amino acid sequence represented by any of the even-numbered SEQ ID NOs: 2 to 30) as a template and a pair of polynucleotides (primers) for cancer detection in a known buffer in the presence of thermostable DNA polymerase such as Taq polymerase or Pfu polymerase and dNTPs (here, N=A, T, C, and G) by varying the temperature of the reaction solution in each step. In general, the denaturation step is performed at 90° C. to 95° C., the annealing step is performed at or near the Tm of the template and the primers (preferably within ±4° C.), and the extension step is performed at 72° C., which is the optimum temperature for thermostable DNA polymerase such as Taq polymerase or Pfu polymerase, or a temperature near the optimum temperature. The duration of each step is adequately set to between about 30 seconds and 2 minutes. This heating cycle is repeated about 25 to 40 times, for example, so that the template nucleic acid region sandwiched between a pair of primers is amplified. The nucleic acid amplification method is not limited to PCR, and any other nucleic acid amplification methods well known in the art can be employed. When a nucleic acid amplification method is performed using a pair of polynucleotides for cancer detection as primers and a nucleic acid in test object as a template, as described above, the nucleic acid is amplified. If a sample does not contain the test nucleic acid, however, amplification does not take place. Accordingly, an amplification product may be detected so as to determine the presence or absence of the nucleic acid in the sample. An amplification product can be detected by a method that comprises subjecting a reaction solution after amplification to electrophoresis and then staining the band with ethidium bromide or the like or a method that comprises immobilizing an amplification product after electrophoresis on a solid phase such as a nylon membrane, performing hybridization with a labeling probe that specifically hybridizes to a nucleic acid, washing, and then detecting the label. Also, so-called real-time detection PCR is performed using a quencher fluorescent dye and a reporter fluorescent dye, and the amount of a nucleic acid in a specimen can thus be quantified. Since kits for real-time detection PCR are commercially available, real-time detection PCR can be easily performed. Further, semi-quantitative measurement of a nucleic acid in test object can also be carried out based on electrophoresis band intensity. A nucleic acid in test object may be either mRNA or cDNA reversely transcribed from mRNA. When mRNA is amplified as a nucleic acid, a NASBA method (the 3 SR method or TMA method) using the above pair of primers can also be employed. The NASBA method is well known, and kits therefor are also commercially available, so that the method can be easily performed using the above pair of primers.

As a probe, a labeled probe that is prepared by labeling a polynucleotide for cancer detection with a fluorescent label, a radiolabel, a biotin label, or the like can be used. Methods for labeling a polynucleotide are well known. The presence or absence of a nucleic acid in a sample can be examined by immobilizing a nucleic acid or an amplification product thereof, performing hybridization with a labeled probe, washing, and then measuring the label bound to the solid phase. Alternatively, a polynucleotide for cancer detection is immobilized, a nucleic acid in test object is hybridized thereto, and the test nucleic acid bound to the solid phase can then be detected using the labeled probe or the like. In such a case, a polynucleotide for cancer detection bound to a solid phase is also referred to as a "probe." Methods for measuring a nucleic acid using a polynucleotide probe are also well known in the art. Such a method can be performed by, in a buffer, bringing a polynucleotide probe into contact with a nucleic acid in test object at Tm or near Tm (preferably, ±4° C.) for hybridization, washing, and then measuring the labeled probe hybridized or the template nucleic acid bound to the solid-phase probe. Examples of such method include well-known methods such as Northern blotting, in situ hybridization, and Southern blotting. In the present invention, any well-known method is applicable.

According to the detection method of the present invention, whether or not a subject animal (or a subject) is afflicted with pancreatic cancer is evaluated based on the presence or amount of CAPRIN-1 expression measured as described above. While pancreatic cancer can be detected only by measuring the presence or amount of CAPRIN-1 expression in a subject animal, it is preferable that the expression levels (the antibody level, polypeptide level, or mRNA level) of CAPRIN-1 in one or more samples of healthy subjects is examined and the determined value of a subject animal is compared with the standard value obtained from healthy subjects, in view of enhancing detection accuracy. To further enhance detection accuracy, CAPRIN-1 expression levels are measured for samples obtained from many patients found to have pancreatic cancer, so as to obtain a standard value for pancreatic cancer patients, and the determined value of a subject animal may then be compared with both the standard value for healthy subjects and the standard value for pancreatic cancer patients. The above standard values can be determined by, for example, quantifying the CAPRIN-1 expression level in each sample and calculating the mean value thereof. The standard value for healthy subjects and the same for pancreatic cancer patients can be determined in advance by measuring CAPRIN-1 expression levels in many healthy subjects and pancreatic cancer patients. When comparison with the standard value is performed in the method of the present invention, accordingly, a standard value determined in advance may be used.

The detection method of the present invention may comprise diagnosis based on other cancer antigens or cancer markers in combination. This can further enhance the accuracy of pancreatic cancer detection. When an antibody specifically existing in pancreatic cancer patients is measured by the method of the present invention, for example, another polypeptide that is often expressed in a cancer tissue can be used in combination as an antigen in a manner similar to that used for polypeptides described above. Also, the method of the present invention may be performed in combination with diagnosis using a previously known cancer marker.

Pancreatic cancer to be subjected to the method for detecting pancreatic cancer of the present invention is pancreatic cancer expressing CAPRIN-1. Examples of such cancer include, but are not limited to, pancreatic ductal carcinoma, invasive pancreatic ductal carcinoma, adenocarcinoma, acinar cell carcinoma, adenosquamous carcinoma, giant cell tumor, intraductal papillary-mucinous neoplasm (IPMN), mucinous cystic neoplasm (MCN), pancreatoblastoma, serous cystadenocarcinoma, solid-pseudopapillary tumor (SPT), gastrinomas (Zollinger-Ellison syndrome), glucagonomas, insulinomas, multiple endocrine neoplasia Type-1 (MEN1) (Wermer syndrome), nonfunctional islet cell tumor, somatostatinomas, and VIPomas. A subject in the method of the present invention is a mammal, preferably a human or a dog.

Examples of samples to be subjected to the method of the present invention include body fluids, such as blood, serum, blood plasma, ascites fluid, and pleural effusion, tissues, and cells. In the first method and the second method, in particular, serum, blood plasma, ascites fluid, pleural effusion, tissue, and cell samples can be preferably used. In the third method comprising measuring a nucleic acid such as mRNA, tissue and cell samples are preferable.

One or more polypeptides to be used as antigens for immunoassay in the first method described above (i.e., the canine CAPRIN-1 of SEQ ID NO: 2 and a homolog thereof, a specifically reactive partial polypeptide, a specifically reactive modified polypeptide, and a specifically reactive addition polypeptide) can be provided as reagents or kits for detection of pancreatic cancer. Such a reagent may consist of the above polypeptide, or it may contain various additives useful for stabilization of the polypeptide, a buffer necessary for assay, secondary antibodies, substrates for enzymes, or the like, separately. Alternatively, such a reagent can be immobilized on a solid phase such as a plate or membrane. Preferable examples of such polypeptides are given above.

An antibody or an antigen-binding fragment thereof, which undergoes an antigen-antibody reaction with CAPRIN-1, used for immunoassays of CAPRIN-1 by the second method can also be provided in the form of a reagent for pancreatic cancer detection. The reagent for pancreatic cancer detection may consist of the above antibody or an antigen-binding fragment thereof. The reagent may contain various additives useful for stabilization of such antibody or an antigen-binding fragment thereof. Alternatively, a metal, such as manganese or iron, may be bound to the antibody or an antigen-binding fragment thereof. When such metal-bound antibody or an antigen-binding fragment thereof is administered to a living organism, the metal-bound antibody or antigen-binding fragment thereof is accumulated at an increased level at a site at which the antigen protein is present at a higher level. When such metal-bound antibody or antigen-binding fragment thereof is administered to a living organism, the metal-bound antibody or antigen-binding fragment thereof is accumulated at an increased level at a site at which the antigen protein is present at a higher level. Therefore, the metal is measured by MRI or the like, and the presence of cancer cells producing the antigen protein can be thus detected.

Furthermore, one or more the above polynucleotides for pancreatic cancer detection to be used for measuring a nucleic acid such as mRNA in the third method can also be provided as a reagent or kit for pancreatic cancer detection. In such a case, the reagent for pancreatic cancer detection may consist of the polynucleotide, or it may contain various additives useful for stabilization of the polypeptide, a buffer necessary for assay (e.g., a fluorescent label), and the like, separately. The polynucleotide for pancreatic cancer detection contained in the reagent is preferably a primer(s) or a probe(s). Conditions and preferable examples of the polynucleotide for pancreatic cancer detection are as described above.

EXAMPLES

The present invention will be described in more detail with reference to the following examples, although the technical scope of the present invention is not limited to the examples.

Example 1

Obtaining Pancreatic Cancer Antigenic Protein by SEREX Method (1) Construction of cDNA Library Total RNA was extracted from a testis tissue of a healthy dog by the acid guanidium-phenol-chloroform method, and poly A RNA was purified using an Oligotex-dT30 mRNA purification kit (Takara Shuzo, Co., Ltd.) in accordance with the protocols attached to the kit.

A canine testis cDNA phage library was synthesized using the thus obtained mRNA (5 μg). The cDNA phage library was constructed using cDNA Synthesis Kit, ZAP-cDNA Synthesis Kit, and ZAP-cDNA GigapackIII Gold Cloning Kit (STRATAGENE) in accordance with the protocols attached to the kits. The size of the thus constructed cDNA phage library was $7.73\times10^5$ pfu/ml.

(2) Screening of cDNA Library Using Serum

Immunoscreening was performed using the canine testis cDNA phage library constructed above. Specifically, host *Escherichia coli* (XL1-Blue MRF') was infected with the phage on an NZY agarose plate (Φ90×15 mm) so as to obtain 2,210 clones. *E. coli* cells were cultured at 42° C. for 3 to 4 hours to form plaques. The plate was covered with a nitrocellulose membrane (Hybond C Extra: GE Healthcare Bio-Science) impregnated with IPTG (isopropyl-β-D-thiogalactoside) at 37° C. for 4 hours, so that the protein was induced to express and then transferred to the membrane. Thereafter, the membrane was collected and then soaked in TBS (10 mM Tris-HCl, 150 mM NaCl, pH 7.5) containing 0.5% powdered skim milk, followed by shaking at 4° C. overnight, so as to suppress nonspecific reactions. The filter was subjected to a reaction with a 500-fold diluted serum of a afflicted dog r at room temperature for 2 to 3 hours.

As the above serum of the afflicted dog, a serum collected from a canine afflicted with pancreatic cancer was used. The serum was stored at −80° C. and then subjected to pretreatment immediately before use. A method for serum pretreatment is as follows. Specifically, host *Escherichia coli* (XL1-Blue MRF') was infected with a λ ZAP Express phage into which no foreign gene had been inserted, and culture was conducted overnight on a NZY plate medium at 37° C. Subsequently, buffer (0.2 M $NAHCO_3$, pH 8.3) containing 0.5 M NaCl was added to the plate, the plate was allowed to stand at 4° C. for 15 hours, and a supernatant was then collected as an *Escherichia coli*/phage extract. The thus collected *Escherichia coli*/phage extract was then applied to an NHS-column (GE Healthcare Bio-Science), so that an

*Escherichia coli*/phage-derived protein was immobilized. The serum of the afflicted dog was applied to the protein-immobilized column for reaction and *Escherichia coli* and an antibody adsorbed to the phage were then removed from the serum. The serum fraction that had passed through the column was diluted 500-fold with TBS containing 0.5% powdered skim milk. The diluted serum fraction was used as an immunoscreening material.

A membrane onto which the treated serum and the above fusion protein had been blotted was washed 4 times with TBS-T (0.05% Tween 20/TBS), and the membrane was then allowed to react with goat anti-canine IgG (Goat anti-Dog IgG-h+I HRP conjugated, BETHYL Laboratories) diluted 5000-fold with TBS containing 0.5% powdered skim milk as a secondary antibody at room temperature for 1 hour. Detection was performed via an enzymatic color development reaction using the NBT/BCIP reaction solution (Roche). Colonies that matched sites positive for the color development reaction were collected from the NZY agarose plate (Φ90×15 mm) and then dissolved in 500 μl of an SM buffer (100 mM NaCl, 10 mM $MgClSO_4$, 50 mM Tris-HCl, 0.01% gelatin, pH 7.5). Until colonies positive for color development reaction were unified, secondary screening and tertiary screening were repeated by a method similar to the above, so that 30,940 phage clones reacting with the serum IgG were screened. Thus, 5 positive clones were isolated.

(3) Homology Search for Isolated Antigen Gene

For nucleotide sequence analysis of the 5 positive clones isolated by the above method, a procedure for conversion from phage vectors to plasmid vectors was performed. Specifically, 200 μl of a solution containing host *Escherichia coli* (XL1-Blue MRF') at the absorbance (OD 600) of 1.0 was prepared. The solution was mixed with 250 μl of a purified phage solution and 1 μl of ExAssist helper phage (STRATAGENE), the mixture was subjected to a reaction at 37° C. for 15 minutes, 3 ml of LB medium was added thereto, and culture was then performed at 37° C. for 2.5 to 3 hours. Immediately thereafter, the temperature of the solution was kept in a water bath at 70° C. for 20 minutes, centrifugation was performed at 4° C. and 1000×g for 15 minutes, and the supernatant was then collected as a phagemid solution. Subsequently, 200 μl of a solution containing phagemid host *Escherichia coli* (SOLR) at the absorbance $OD_{600}$ of 1.0 was prepared. The resulting solution was mixed with 10 μl of a purified phage solution, followed by a reaction at 37° C. for 15 minutes. The reaction product (50 ml) was seeded on LB agar medium containing ampicillin (final concentration: 50 μg/ml), and culture was conducted at 37° C. overnight. Transformed SOLR single colony was collected and then cultured in LB medium containing ampicillin (final concentration: 50 μg/ml) at 37° C. Thereafter, plasmid DNA containing an insert of interest was purified using the QIAGEN plasmid Miniprep Kit (QIAGEN).

The purified plasmid was subjected to analysis of the full-length insert sequence by the primer walking method using the T3 primer represented by SEQ ID NO: 31 and the T7 primer represented by SEQ ID NO: 32. As a result of sequence analysis, the gene sequences represented by SEQ ID NOs: 5, 7, 9, 11, and 13 were obtained. A homology search program, BLAST search (www.ncbi.nlm.nih.gov/BLAST/), was performed using the nucleotide sequences and amino acid sequences (SEQ ID NOs: 6, 8, 10, 12, and 14) of the genes. As a result of this homology search with known genes, all of the 5 obtained genes were found to encode CAPRIN-1. The sequence identity among the 5 genes was 100% for nucleotide sequence and 99% for amino acid sequence in regions translated into proteins. Also, the sequence identity between the canine gene (any of SEQ ID NO: 5, 7, 9, 11, or 13) and a gene encoding a human homolog thereof was 94% for nucleotide sequence and 98% for amino acid sequence in regions translated into proteins. The nucleotide sequences of the human homolog are represented by SEQ ID NOs: 1 and 3 and the amino acid sequences of the same are represented by SEQ ID NOs: 2 and 4. Also, the sequence identity between the obtained canine gene and a gene encoding a cattle homolog was 94% for nucleotide sequence and 97% for amino acid sequence in regions translated into proteins. The nucleotide sequence of the cattle homolog is represented by SEQ ID NO: 15 and the amino acid sequence of the same is represented by SEQ ID NO: 16. The sequence identity between the gene encoding the human homolog and the gene encoding the cattle homolog was 94% for nucleotide sequences and ranged from 93% to97% for amino acid sequence in regions translated into proteins. Also, the sequence identity between the obtained canine gene and a gene encoding an equine homolog was 93% for nucleotide sequence and 97% for amino acid sequence in regions translated into proteins. The nucleotide sequence of the equine homolog is represented by SEQ ID NO: 17 and the amino acid sequence of the same is represented by SEQ ID NO: 18. The sequence identity between the gene encoding the human homolog and the gene encoding the equine homolog was 93% for nucleotide sequence and 96% for amino acid sequence in regions translated into proteins. Also, the sequence identity between the obtained canine gene and a gene encoding the mouse homolog ranged from 87% to 89% in terms of nucleotide sequence and ranged from 95% to 97% for amino acid sequence in regions translated into proteins. The nucleotide sequences of the mouse homolog are represented by SEQ ID NOs: 19, 21, 23, 25, and 27 and the amino acid sequences of the same are represented by SEQ ID NOs: 20, 22, 24, 26, and 28. The sequence identity between the gene encoding the human homolog and the gene encoding the mouse homolog ranged from 89% to 91% for nucleotide sequence and ranged from 95% to 96% for amino acid sequence in regions translated into proteins. Also, the sequence identity between the obtained canine gene and a gene encoding a chicken homolog was 82% for nucleotide sequence and 87% for amino acid sequence in regions translated into proteins. The nucleotide sequence of the chicken homolog is represented by SEQ ID NO: 29 and the amino acid sequence of the same is represented by SEQ ID NO: 30. The sequence identity between the gene encoding the human homolog and the gene encoding the chicken homolog ranged from 81% to 82% for nucleotide sequence and 86% for amino acid sequence in regions translated into proteins.

(4) Gene Expression Analysis in Human Pancreatic Cancer Cell Lines

Expression of the genes obtained by the above method in human normal tissues (i.e., mammary gland, brain, bone marrow, lung, esophagus, pancreas, and testis) and 4 types of pancreatic cancer cell lines (i.e., Capan-2, MIAPaCa-2, PANC-1, and BxPC-3) was examined by RT-PCR (reverse transcription-PCR). A reverse transcription reaction was performed as follows. Specifically, total RNA was extracted from each tissue (50 mg to 100 mg) and each cell line (5-10×$10^6$ cells) using the TRIZOL reagent (Invitrogen) in accordance with the attached protocols. cDNA was synthesized using the total RNA and the Superscript First-Strand Synthesis System for RT-PCR (Invitrogen) in accordance with the attached protocols. PCR was performed as follows using primers specific to the obtained genes (represented by SEQ ID NOs: 33 and 34). Specifically, PCR was performed by preparing a reaction solution to bring a total amount thereof to 25 µl with the addition of reagents and an included buffer (i.e., 0.25 µl of a sample prepared by reverse transcription reaction, the above primers (2 µM each), dNTPs (0.2 mM each), 0.65 U of ExTaq polymerase (Takara Shuzo, Co., Ltd.)), the resulting solution was subjected to a cycle of 94° C. for 30 seconds, 60° C. for 30 seconds, and 72° C. for 30 seconds using a Thermal Cycler (BIO RAD), and this cycle was repeated 30 times. The gene-specific primers mentioned above were used to amplify the region between the nucleotide No. 698 and the nucleotide No. 1124 in the nucleotide sequence represented by SEQ ID NO: 1 (the human CAPRIN-1 gene). For comparison, GAPDH-specific primers (represented by SEQ ID NOs: 35 and 36) were used at the same time. As a result of inspection of human CAPRIN-1 gene expression, expression thereof was observed only in the testis in the case of healthy canine tissues, although expression was observed in the pancreatic cancer cells. The results demonstrate that CAPRIN-1 expression was not observed in normal tissues other than those of the testis, while CAPRIN-1 expression was observed in the pancreatic cancer cells.

(5) CAPRIN-1 Expression in Normal Mouse and Canine Tissues

Mice (Balb/c, female) and dogs (beagle dogs, female) were exsanguinated under ether anesthesia and ketamine/isoflurane anesthesia. After laparotomy, organs (stomach, liver, eyeball, thymus gland, muscle, bone marrow, uterus, small intestine, esophagus, heart, kidney, salivary gland, large intestine, mammary gland, brain, lung, skin, adrenal gland, ovary, pancreas, spleen, and bladder) were each transferred to a 10 cm dish containing PBS. Each organ was cut open in PBS and then fixed by perfusion overnight with 0.1 M phosphate buffer (pH 7.4) containing 4% paraformaldehyde (PFA). The perfusate was discarded, the tissue surface of each organ was rinsed with PBS, and a PBS solution containing 10% sucrose was then introduced into a 50 ml centrifugal tube. Each tissue was then introduced into each tube, followed by shaking using a rotor at 4° C. for 2 hours. Each solution was substituted with a PBS solution containing 20% sucrose and then allowed to stand at 4° C. until tissues precipitated. Each solution was substituted with a PBS solution containing 30% sucrose and then allowed to stand at 4° C. until tissues precipitated. Each tissue was removed and a necessary portion was excised with a surgical scalpel. Subsequently, the OCT compound (Tissue Tek) was applied and spread over each tissue surface, and the tissues were then placed on Cryomold. Cryomold was placed on dry ice for rapid freezing. Tissues were sliced into pieces of 10 to 20 µm long using a cryostat (LEICA), the sliced tissue pieces were then air-dried on glass slides for 30 minutes using a hair dryer, and glass slides onto which sliced tissue pieces had been applied were thus prepared. Subsequently, each glass slide was introduced into a staining bottle filled with PBS-T (saline containing 0.05% Tween 20), a procedure involving exchanging PBS-T with fresh PBS-T was performed every 5 minutes, and this procedure was repeated 3 times. Excess water around each specimen was removed using Kimwipes and each section was then encircled using DAKOPEN (DAKO). As blocking solutions, a MOM mouse Ig blocking reagent (VECTASTAIN) was applied onto mouse tissue and a PBS-T solution containing a 10% fetal calf serum was applied onto canine tissue. The resultants were allowed to stand in a moist chamber at room temperature for 1 hour. Subsequently, a solution prepared with the blocking solution to a 10 µg/ml anti-CAPRIN-1 monoclonal antibody (monoclonal antibody #8) having the heavy chain variable region of SEQ ID NO: 55 and the light chain variable region of SEQ ID NO: 56, which reacts with the cancer cell surfaces prepared in Example 3, was applied onto each slide glass and then allowed to stand within a moist chamber at 4° C. overnight. After 3 instances of 10-minutes-washing with PBS-T, a MOM biotin-labeled anti-IgG antibody (VECTASTAIN) diluted 250-fold with the blocking solution was applied onto each glass slide and then allowed to stand within a moist chamber at room temperature for 1 hour. After 3 instances of 10-minutes-washing with PBS-T, an avidin-biotin ABC reagent (VECTASTAIN) was applied and then allowed to stand within a moist chamber at room temperature for 5 minutes. After 3 times of 10-minutes-washing with PBS-T, a DAB staining solution (10 mg of DAB+10 µl of 30% $H_2O_2$, and 50 ml of 0.05M Tris-HCl, pH 7.6) was applied, and the glass slides were then allowed to stand within a moist chamber at room temperature for 30 minutes. Glass slides were rinsed with distilled water and a hematoxylin reagent (DAKO) was then applied. After being allowed to stand at room temperature for 1 minute, the glass slides were rinsed with distilled water. The glass slides were put in 70%, 80%, 90%, 95%, and 100% ethanol solutions in such order for 1 minute each and then allowed to stand in xylene overnight. The glass slides were removed, cover-slipped with Glycergel Mounting Medium (DAKO), and then observed. As a result, CAPRIN-1 expression was observed to a slight degree within cells in all of salivary gland, kidney, colon, and stomach tissues, but no CAPRIN-1 expression was observed on cell surfaces. Also, absolutely no CAPRIN-1 expression was observed in tissues from other organs.

Example 2

Preparation of Canine and Human CAPRIN-1 Proteins (1) Preparation of Recombinant Protein A recombinant protein was prepared by the following method based on the gene of SEQ ID NO: 5 obtained in Example 1. PCR was performed by preparing a reaction solution to bring a total amount thereof to 50 µl with the addition of reagents and an included buffer (i.e., 1 µl of a vector prepared from the phagemid solution obtained in Example 1 and then subjected to sequence analysis, 2 types of primers containing NdeI and KpnI restriction enzyme cleavage sequences (0.4 µM each; SEQ ID NOs: 37 and 38), 0.2 mM dNTPs, and 1.25 U PrimeSTAR HS polymerase (Takara Shuzo, Co., Ltd.)), the resulting reaction solution was subjected to a cycle of 98° C. for 10 seconds and 68° C. for 1.5 minutes using a Thermal Cycler (BIO RAD), and this cycle was repeated 30 times. The above 2 types of primers were used to amplify the region encoding the full-length amino acid sequence of SEQ ID NO: 6 (canine CAPRIN-1). After PCR, the amplified DNA was subjected to 1% agarose gel electrophoresis, and a DNA fragment of about 1.4 kbp was then purified from the gel using a QIAquick Gel Extraction Kit (QIAGEN).

The purified DNA fragment was ligated to a pCR-Blunt cloning vector (Invitrogen). The vector was transformed into *Escherichia coli*, the plasmid was collected, and the amplified gene fragment was confirmed to match the target sequence via sequencing. The plasmid that matched the target sequence was treated with NdeI and KpnI restriction enzymes, the resultant was purified using a QIAquick Gel Extraction Kit, and the target gene sequence was inserted into a pET30b expression vector (Novagen) for *Escherichia coli* treated with NdeI and KpnI restriction enzymes. With the use of the resulting vector, a His tag-fused recombinant protein can be produced. The plasmid was transformed into *Escherichia coli* BL21 (DE3) for expression, and the target protein was induced to express in *Escherichia coli* with the aid of 1 mM IPTG.

Separately, the recombinant protein of a canine homolog gene was prepared by the following method based on the gene of SEQ ID NO: 7. PCR was performed by preparing a reaction solution to bring a total amount thereof to 50 μl with the addition of reagents and an included buffer (i.e., 1 μl of cDNA, the expression of which was confirmed via RT-PCR, selected from among the various tissues and cellular cDNAs prepared in Example 1, 2 types of primers containing NdeI and KpnI restriction enzyme cleavage sequences (0.4 μM each; SEQ ID NOs: 39 and 40), 0.2 mM dNTPs, and 1.25 U PrimeSTAR HS polymerase (Takara Shuzo, Co., Ltd.)), the resulting reaction solution was subjected to a cycle of 98° C. for 10 seconds and 68° C. for 2.5 minutes using a Thermal Cycler (BIO RAD), and this cycle was repeated 30 times. The above 2 types of primers were used to amplify the region encoding the full-length amino acid sequence of SEQ ID NO: 8. After PCR, the amplified DNA was subjected to 1% agarose gel electrophoresis, and a DNA fragment of about 2.2 kbp was then purified from the gel using a QIAquick Gel Extraction Kit (QIAGEN).

The purified DNA fragment was ligated to a pCR-Blunt cloning vector (Invitrogen). The vector was transformed into *Escherichia coli*, the plasmid was collected, and the amplified gene fragment was confirmed to match the target sequence via sequencing. The plasmid that matched the target sequence was treated with NdeI and KpnI restriction enzymes, the resultant was purified using a QIAquick Gel Extraction Kit, and the target gene sequence was inserted into a pET30b expression vector (Novagen) for *Escherichia coli* treated with NdeI and KpnI restriction enzymes. With the use of the resulting vector, a His tag-fused recombinant protein can be produced. The plasmid was transformed into *Escherichia coli* BL21 (DE3) for expression, and the target protein was induced to express in *Escherichia coli* with the aid of 1 mM IPTG.

Separately, the recombinant protein of a human homolog gene was prepared by the following method based on the gene of SEQ ID NO: 1. PCR was performed by preparing a reaction solution to bring a total amount thereof to 50 μl with the addition of reagents and an included buffer (i.e., 1 μl of cDNA, the expression of which was confirmed via RT-PCR, selected from among the various tissue and cellular cDNAs prepared in Example 1, 2 types of primers containing Sad and XhoI restriction enzyme cleavage sequences (0.4 μM each; SEQ ID NOs: 41 and 42), 0.2 mM dNTPs, and 1.25 U PrimeSTAR HS polymerase (Takara Shuzo, Co., Ltd.)), the resulting reaction solution was subjected to a cycle of 98° C. for 10 seconds and 68° C. for 2.5 minutes using a Thermal Cycler (BIO RAD), and this cycle was repeated 30 times. The above 2 types of primers were used to amplify the region encoding the full-length amino acid sequence of SEQ ID NO: 2. After PCR, the amplified DNA was subjected to 1% agarose gel electrophoresis, and a DNA fragment of about 2.1 kbp was then purified from the gel using a QIAquick Gel Extraction Kit (QIAGEN).

The purified DNA fragment was ligated to a pCR-Blunt cloning vector (Invitrogen). The vector was transformed into *Escherichia coli*, the plasmid was collected, and the amplified gene fragment was confirmed to match the target sequence via sequencing. The plasmid that matched the target sequence was treated with SacI and XhoI restriction enzymes, the resultant was purified using a QIAquick Gel Extraction Kit, and the target gene sequence was inserted into a pET30a expression vector (Novagen) for *Escherichia coli* treated with SacI and XhoI restriction enzymes. With the use of the resulting vector, a His tag-fused recombinant protein can be produced. The plasmid was transformed into *Escherichia coli* BL21 (DE3) for expression, and the target protein was induced to express in *Escherichia coli* with the aid of 1 mM IPTG.

(2) Purification of Recombinant Protein

The above-obtained recombinant *Escherichia coli* strain expressing SEQ ID NO: 1, 5, or 7 was cultured at 37° C. in LB medium containing 30 μg/ml kanamycin until the absorbance at 600 nm reached around 0.7. Thereafter, isopropyl-β-D-1-thiogalactopyranoside was added to a final concentration of 1 mM, and culture was conducted at 37° C. for 4 hours. Subsequently, the culture was centrifuged at 4800 rpm for 10 minutes to collect cells. The cell pellet was suspended in phosphate buffered saline and then centrifuged at 4800 rpm for 10 minutes to wash the cells.

The cells were suspended in phosphate buffered saline and then subjected to ultrasonication on ice. The ultrasonicated *Escherichia coli* solution was centrifuged at 6000 rpm for 20 minutes, the resulting supernatant was designated as a soluble fraction, and the resulting precipitate was designated as an insoluble fraction.

The soluble fraction was added to a nickel chelate column (carrier: Chelating Sepharose™ Fast Flow (GE Healthcare), column capacity: 5 ml, 50 mM hydrochloric acid buffer (pH 8.0) as equilibrating buffer)) prepared in accordance with a conventional method. The non-adsorbed fraction was washed with 10 column volumes of 50 mM hydrochloric acid buffer (pH 8.0) and 20 mM phosphate buffer (pH 8.0) containing 20 mM imidazole. Immediately thereafter, 6 beds were eluted with 20 mM phosphate buffer (pH 8.0) containing 100 mM imidazole. After the elution of the protein of interest had been confirmed by Coomassie staining, an elution fraction of 20 mM phosphate buffer (pH 8.0) containing 100 mM imidazole was added to a strong anion exchange column (carrier: Q Sepharose™ Fast Flow (GE Healthcare), column volume: 5 ml, and 20 mM phosphate buffer (pH 8.0) as equilibrating buffer). The non-adsorbed fraction was washed with 10 column volumes of 20 mM phosphate buffer (pH 7.0) and 20 mM phosphate buffer (pH 7.0) containing 200 mM sodium chloride. Immediately thereafter, 5 beds were eluted using 20 mM phosphate buffer (pH 7.0) containing 400 mM sodium chloride. Thus, purified fractions of proteins having the amino acid sequences represented by SEQ ID NO: 2, 6, and 8 were obtained, and these purified fractions were hereafter used as materials for administration tests.

Each of the purified preparations obtained by the above method (200 μl each) was dispensed into 1 ml of a reaction buffer (20 mM Tris-HCl, 50 mM NaCl, 2 mM $CaCl_2$, pH 7.4), and 2 μl of enterokinase (Novagen) was then added. The preparation was allowed to stand at room temperature overnight for reaction, a His tag was cleaved, and purification was then performed in accordance with the protocols attached to the Enterokinase Cleavage Capture Kit (Novagen). Subsequently, 1.2 ml of the purified preparation obtained by the above method was substituted with physiological phosphate buffer (Nissui Pharmaceutical Co., Ltd.) using ultrafiltration NANOSEP 10K OMEGA (PALL). Sterilized filtration was performed using 0.22 μm HT Tuffryn Acrodisc (PALL), and the resultants were used for the following experiments.

Example 3

Preparation of Antibody Against CAPRIN-1

(1) Preparation of Polyclonal Antibody Against CAPRIN-1-Derived Peptide

In order to obtain an antibody binding to CAPRIN-1, a CAPRIN-1-derived peptide (Arg-Asn-Leu-Glu-Lys-Lys-Lys-Gly-Lys-Leu-Asp-Asp-Tyr-Gln; SEQ ID NO: 43) was synthesized. The peptide as an antigen (1 mg) was mixed with the equivalent volume of an incomplete Freund's adjuvant (IFA) solution, and the mixture was subcutaneously administered to a rabbit 4 times every 2 weeks. Thereafter, blood was collected, and an antiserum containing a polyclonal antibody was obtained. Further, the antiserum was purified using a protein G carrier (GE Healthcare Bio-Sciences), and a polyclonal antibody against the CAPRIN-1-derived peptide was then obtained. Subsequently, the reactivity of the resulting polyclonal antibody to CAPRIN-1 on the cancer cell surface was examined using breast cancer cells. Specifically, $10^6$ cells of the human breast cancer cell line MDA-MB-231 V were subjected to centrifugation in a 1.5 ml microcentrifugal tube, a PBS solution supplemented with 0.1% fetal bovine serum (FBS) containing the polyclonal antibody was added thereto, and the resultant was then allowed to stand on ice for 1 hour. After washing with PBS, an FITC-labeled goat anti-mouse IgG antibody (Invitrogen) diluted 500-fold with PBS containing 0.1% FBS was added to the solution, and the solution was then allowed to stand on ice for 1 hour. After washing with PBS, fluorescence intensity was measured using a FACS Calibur (Becton, Dickinson and Company). Separately, a control was prepared in accordance with a procedure similar to the above, except that PBS containing 0.1% FBS was added instead of the polyclonal antibody. As a result, fluorescence intensity in cells treated with the polyclonal antibody was found to be stronger than that in control cells, and the obtained polyclonal antibody was thus found to bind to the breast cancer cell surface.

(2) Preparation of Monoclonal Antibody Against CAPRIN-1 Protein

The antigenic protein (human CAPRIN-1) (100 μg) represented by SEQ ID NO: 2 prepared in Example 2 was mixed with the equivalent amount of a MPL+TDM adjuvant (Sigma), and the mixture was used as an antigen solution per mouse. The antigen solution was administered intraperitoneally to a 6-week-old Balb/c mouse (Japan SLC Inc.) and further administered 3 times every week. The spleen was removed 3 days after the final immunization, ground in between two sterilized glass slides, washed with PBS (−) (Nissui), and then centrifuged at 1500 rpm for 10 minutes to remove supernatants. This procedure was repeated 3 times to obtain spleen cells. The thus obtained spleen cells were mixed with the mouse myeloma SP2/0 cells (purchased from ATCC) at a ratio of 10:1. The PEG solution prepared by mixing 200 μl of RPMI1640 medium containing 10% FBS heated to 37° C. and 800 μl of PEG1500 (Boehringer) was added to the cells. The solution was allowed to stand for 5 minutes for cell fusion. Centrifugation was performed at 1700 rpm for 5 minutes to remove supernatants, the cells were suspended in 150 ml of RPMI1640 medium (HAT selective medium) containing 15% FBS supplemented with 2% equivalent of HAT solution (Gibco), and the suspension was then seeded onto fifteen 96-well plates (Nunc) at 100 μl/well. Cells were cultured for 7 days at 37° C. in the presence of 5% $CO_2$. Thus, hybridomas resulting from fusion of spleen cells with myeloma cells were obtained.

Hybridomas were selected using, as an indicator, the binding affinity of the antibody produced by the prepared hybridomas for the CAPRIN-1 protein. The CAPRIN-1 protein solution (1 μg/ml) prepared in Example 2 was added to a 96-well plate at 100 μl/well, and the resultant was allowed to stand at 4° C. for 18 hours. Each well was washed 3 times with PBS-T, a 0.5% bovine serum albumin (BSA) solution (Sigma) was added at 400 μl/well, and the plate was then allowed to stand at room temperature for 3 hours. The solution was removed and each well was washed 3 times with 400 μl of PBS-T. Thereafter, each culture supernatant of the hybridomas obtained above was added at 100 μl/well, and the resultant was then allowed to stand at room temperature for 2 hours. Each well was washed 3 times with PBS-T, an HRP-labeled anti-mouse IgG (H+L) antibody (Invitrogen) diluted 5000-fold with PBS was added thereto at 100 μl/well, and the resultant was allowed to stand at room temperature for 1 hour. After each well was washed 3 times with PBS-T, a TMB substrate solution (Thermo) was added at 100 μl per/well, and the resultant was allowed to stand for 15 to 30 minutes, so as to allow the color to develop. Thereafter, 1N sulfuric acid was added at 100 μl/well to terminate the reaction. The absorbance was measured at 450 nm and 595 nm using a spectrophotometer. As a result, a plurality of hybridomas producing antibodies exhibiting high absorbance values were selected.

The thus selected hybridomas were added to a 96-well plate at 0.5 hybridomas per well and then cultured. After 1 week, hybridomas forming single colonies in wells were observed. Cells in these wells were further cultured, and hybridomas were selected using, as an indicator, the binding affinity of the antibody produced by the cloned hybridomas for the CAPRIN-1 protein. The CAPRIN-1 protein solution (1 μg/ml) prepared in Example 2 was added to a 96-well plate at 100 μl/well, and the resultant was allowed to stand at 4° C. for 18 hours. Each well was washed 3 times with PBS-T, a 0.5% BSA solution was added at 400 μl/well, and the plate was then allowed to stand at room temperature for 3 hours. The solution was removed and each well was washed 3 times with 400 μl of PBS-T. Thereafter, each culture supernatant of the hybridomas obtained above was added at 100 μl/well, and the resultant was then allowed to stand at room temperature for 2 hours. Each well was washed 3 times with PBS-T, an HRP-labeled anti-mouse IgG (H+L) antibody (Invitrogen) diluted 5000-fold with PBS was added thereto at 100 μl/well, and the resultant was allowed to stand at room temperature for 1 hour. After each well was washed 3 times with PBS-T, a TMB substrate solution (Thermo) was added at 100 μl per/well and then allowed to stand for 15 to 30 minutes, so as to allow the color to develop. Thereafter, 1N sulfuric acid was added at 100 μl/well to terminate the reaction, and the absorbance was measured at 450 nm and 595 nm using a spectrophotometer. As a result, a plurality of hybridomas producing monoclonal antibodies exhibiting reactivity to the CAPRIN-1 protein were selected, the culture supernatant of hybridomas was purified using a protein G carrier, and 150 monoclonal antibodies binding to the CAPRIN-1 protein were obtained.

Subsequently, monoclonal antibodies exhibiting reactivity to the surfaces of cancer cells expressing CAPRIN-1 were selected from among these monoclonal antibodies using breast cancer cells. Specifically, $10^6$ cells of the human breast cancer cell line MDA-MB-231 V were subjected to centrifugation in a 1.5 ml microcentrifugal tube, 100 μl of the culture supernatant of the hybridomas was added thereto, and the resultant was then allowed to stand on ice for 1 hour.

After washing with PBS, an FITC-labeled goat anti-mouse IgG antibody (Invitrogen) diluted 500-fold with PBS containing 0.1% FBS was added to the solution, and the solution was then allowed to stand on ice for 1 hour. After washing with PBS, fluorescence intensity was measured using a FACS Calibur (Becton, Dickinson and Company). Separately, a control was prepared in accordance with a procedure similar to the above, except that a medium was added instead of the antibody. As a result, 10 monoclonal antibodies exhibiting stronger fluorescence intensity than that of the control; i.e., 10 monoclonal antibodies exhibiting reactivity to the surfaces of breast cancer cells (#1 to #10), were selected. The heavy chain variable regions and the light chain variable regions of these monoclonal antibodies are shown in SEQ ID NOs: 44 to 60. The above monoclonal antibody #1 comprises the heavy chain variable region of SEQ ID NO: 44 and the light chain variable region of SEQ ID NO: 45, the monoclonal antibody #2 comprises the heavy chain variable region of SEQ ID NO: 44 and the light chain variable region of SEQ ID NO: 46, the monoclonal antibody #3 comprises the heavy chain variable region of SEQ ID NO: 44 and the light chain variable region of SEQ ID NO: 47, the monoclonal antibody #4 comprises the heavy chain variable region of SEQ ID NO: 44 and the light chain variable region of SEQ ID NO: 48, the monoclonal antibody #5 comprises the heavy chain variable region of SEQ ID NO: 49 and the light chain variable region of SEQ ID NO: 50, the monoclonal antibody #6 comprises the heavy chain variable region of SEQ ID NO: 51 and the light chain variable region of SEQ ID NO: 52, the monoclonal antibody #7 comprises the heavy chain variable region of SEQ ID NO: 53 and the light chain variable region of SEQ ID NO: 54, the monoclonal antibody #8 comprises the heavy chain variable region of SEQ ID NO: 55 and the light chain variable region of SEQ ID NO: 56, the monoclonal antibody #9 comprises the heavy chain variable region of SEQ ID NO: 57 and the light chain variable region of SEQ ID NO: 58, and the monoclonal antibody #10 comprises the heavy chain variable region of SEQ ID NO: 59 and the light chain variable region of SEQ ID NO: 60.

(3) Identification of Peptides in CAPRIN-1 Protein to which Antibodies Against CAPRIN-1 Reacting with Breast Cancer Cell Surface Bind With the use of monoclonal antibodies #1 to #10 against CAPRIN-1 reacting with the surfaces of breast cancer cells obtained above, partial sequences in the CAPRIN-1 protein recognized by these monoclonal antibodies were identified.

To 100 μl of a recombinant CAPRIN-1 protein solution adjusted to a concentration of 1 μg/μl with PBS, first of all, DTT (Fluka) was added to result in a final concentration of 10 mM therein, and a reaction was allowed to proceed at 95° C. for 5 minutes, so as to reduce disulfide bonds within the CAPRIN-1 protein. Subsequently, iodoacetamide (final concentration: 20 mM; Wako Pure Chemical Industries, Ltd.) was added, and thiol groups were subjected to alkylation at 37° C. for 30 minutes under shaded conditions. The monoclonal antibodies #1 to #10 against CAPRIN-1 (50 μg each) were added to 40 μg of the reduced-alkylated CAPRIN-1 protein, the volume of the mixture was adjusted to 1 ml with 20 mM phosphate buffer (pH7.0), and the reaction was allowed to proceed at 4° C. overnight with stirring and mixing.

Subsequently, trypsin (Promega) was added to a final concentration of 0.2 μg. After the reaction was allowed to proceed at 37° C. for 1 hour, 2 hours, 4 hours, and then 12 hours, the resultants were mixed with protein A-glass beads (GE), which had been subjected to blocking with PBS containing 1% BSA (Sigma) and washing with PBS in advance, in 1 mM calcium carbonate and NP-40 buffer (20 mM phosphate buffer (pH 7.4), 5 mM EDTA, 150 mM NaCl, and 1% NP-40), and the reaction was allowed to further proceed for 30 minutes.

The reaction solutions were each washed with 25 mM ammonium carbonate buffer (pH 8.0), antigen-antibody complexes were then eluted using 100 μl of 0.1% formic acid, and the eluates were subjected to LC-MS analysis using Q-TOF Premier (Waters-MicroMass) in accordance with the protocols attached to the instrument.

As a result, the polypeptide of SEQ ID NO: 61 was identified as a partial sequence of CAPRIN-1, which was recognized by all of the monoclonal antibodies #1 to #10 against CAPRIN-1. Further, the peptide of SEQ ID NO: 62 was identified as a partial sequence in the polypeptide of SEQ ID NO: 61 above, which was recognized by the monoclonal antibodies #1 to #4, #5 to #7, and #9. In addition, the monoclonal antibodies #1 to #4 were found to recognize the peptide of SEQ ID NO: 63, which was a partial peptide sequence thereof.

Example 4

Diagnosis of Pancreatic Cancer Using CAPRIN-1 Polypeptide

1) Diagnosis of Canine Pancreatic Cancer

As a result of pathological diagnosis using the removed tumor tissue samples, blood samples were collected from afflicted dogs confirmed to have malignant pancreatic ductal carcinoma, and sera were separated. With the use of the canine CAPRIN-1 protein (SEQ ID NO: 8) prepared in Example 2 and the anti-canine IgG antibody, the titer of the serum IgG antibody specifically reacting with the canine CAPRIN-1 protein was measured by an ELISA method.

The prepared canine CAPRIN-1 protein was immobilized by adding a recombinant protein solution diluted to 5 μg/ml with phosphate buffered saline to a 96-well immobilizer amino plate (Nunc) at 100 μl/well and then allowing the plate to stand at 4° C. overnight. Blocking was performed by adding a 50 mM sodium bicarbonate buffer solution (pH 8.4) (hereafter, referred to as a "blocking solution") containing 0.5% BSA (bovine serum albumin, Sigma Aldrich Japan) at 100 μl/well, followed by shaking at room temperature for 1 hour. Serum diluted 1000-fold with the blocking solution was added at 100 μl/well and the mixture was then subjected to a reaction via shaking at room temperature for 3 hours. The reaction product was washed 3 times with phosphate buffered saline containing 0.05% Tween 20 (Wako Pure Chemical Industries, Ltd.; this solution is referred to as "PBS-T" herein), an HRP-modified canine IgG antibody (Goat anti-Dog IgG-h+I HRP conjugated: BETHYL Laboratories) diluted 3000-fold with the blocking solution was added at 100 μl/well, and the mixture was subjected to a reaction via shaking at room temperature for 1 hour. After the reaction product was washed 3 times with PBS-T, HRP substrate TMB (1-Step Turbo TMB (tetramethylbenzidine), PIERCE) was added at 100 μl/well, and an enzyme-substrate reaction was then conducted at room temperature for 30 minutes. Thereafter, a 0.5 M sulfuric acid solution (Sigma Aldrich Japan) was added at 100 μl/well to terminate the reaction, and the absorbance at 450 nm was measured using a microplate reader. As controls, a specimen onto which no recombinant protein prepared had been immobilized and a specimen to which the serum of a cancer-bearing dog would not be allowed to react were subjected to the treatment and comparison in the same manner as described above.

As a result, the titer of the antibody against a canine CAPRIN-1 protein of the sera derived from cancer-carrying dogs was found to be higher than that of the controls.

(2) Diagnosis of Canine Pancreatic Cancer Using Human CAPRIN-1 Protein

With the use of the human CAPRIN-1 protein (SEQ ID NO: 2) prepared in Example 2, the IgG antibody titer of the canine serum reacting with the human CAPRIN-1 protein was measured in the same manner as described above. When serum samples obtained from healthy dogs were subjected to the same measurement, the absorbance at 450 nm was not substantially observed as described above. The serum samples obtained from pancreatic cancer patient dogs of (1) exhibited a higher titer of the antibody against the human CAPRIN-1 protein than that of the control.

(3) Diagnosis of Human Pancreatic Cancer

With the use of the human CAPRIN-1 protein (SEQ ID NO: 2) prepared in Example 2 and the anti-human IgG antibody, the IgG antibody titer of the serum samples obtained from healthy individuals reacting with the polypeptide was measured. The human CAPRIN-1 protein was immobilized by adding a recombinant protein solution diluted to 100 μg/ml with phosphate buffered saline to a 96-well immobilizer amino plate (Nunc) at 100 μl/well and then allowing the plate to stand at 4° C. overnight. Blocking was performed in the following manner. That is, 4 g of Block Ace powder (DS PHARMA BIOMEDICAL Co., Ltd.) was dissolved in 100 ml of purified water, the solution was diluted 4-fold with purified water (hereafter, referred to as a "blocking solution"), the blocking solution was added at 100 μl/well, and the mixture was subjected to shaking at room temperature for 1 hour. Serum diluted 1000-fold with the blocking solution was added at 100 μl/well and then subjected to a reaction via shaking at room temperature for 3 hours. After washing the resultant 3 times with phosphate buffered saline containing 0.05% Tween 20 (Wako Pure Chemical Industries, Ltd.; this solution is referred to as "PBS-T" herein), an HRP-modified anti-human IgG antibody (HRP-Goat Anti-Human IgG (H+L) Conjugate: Zymed Laboratories) diluted 10000-fold with the blocking solution was added at 100 μl/well and then subjected to a reaction via shaking at room temperature for 1 hour. After the reaction product was washed 3 times with PBS-T, HRP substrate TMB (1-Step Turbo TMB (tetramethylbenzidine), PIERCE) was added at 100 μl/well, and an enzyme-substrate reaction was then performed at room temperature for 30 minutes. Thereafter, a 0.5 M sulfuric acid solution (Sigma Aldrich Japan) was added at 100 μl/well to terminate the reaction, and the absorbance at 450 nm was then measured using a microplate reader. An ovalbumin antigen adjusted to 50 μg/ml with phosphate buffered saline was immobilized and then used as a positive control. As a result, the absorbance at 450 nm was found to be high in the case of the ovalbumin antigen, although no absorbance (0) was detected in the case of the human CAPRIN-1 protein.

Further, the serum samples obtained from patients with pancreatic ductal carcinoma were subjected to measurement of the titer of the serum IgG antibody specifically reacting with the human CAPRIN-1 protein (the amino acid sequence of SEQ ID NO: 2) in the same manner as described above. As a result, the absorbance at 450 nm was found to be lower than the lowest detection limit in the case of healthy subjects, although it was found to be high in the case of patients with pancreatic cancer. With the use of the canine CAPRIN-1 protein (SEQ ID NO: 8) prepared in Example 2 and the anti-human IgG antibody, the titer of the human serum IgG antibody specifically reacting with the canine CAPRIN-1 protein was measured in the same manner as described above. As a result, pancreatic cancer patients were found to exhibit higher titers than healthy individuals.

Thus, it was demonstrated that human pancreatic cancer could be detected by the method of the present invention.

Example 5

Diagnosis of Pancreatic Cancer Using Antibody Against CAPRIN-1

(1) Diagnosis of Pancreatic Cancer by Measuring CAPRIN-1 Protein

With the use of the polyclonal antibody against the CAPRIN-1-derived peptide (SEQ ID NO: 43) obtained in Example 3 (1) in combination with each monoclonal antibody against the CAPRIN-1 protein obtained in Example 3 (2), Sandwich ELISA was carried out in order detect the CAPRIN-1 protein (cancer-bearing individual-derived serum) reacted positive upon cancer diagnosis using the CAPRIN-1 protein in Example 4 (1)-(3). The polyclonal antibody was used as a primary antibody and each monoclonal antibody was used as a secondary antibody. The amount of the proteins specifically reacting with each of the above antibodies in the sera was measured.

The primary antibody was immobilized by adding a polyclonal antibody solution diluted to 5 μg/ml with phosphate buffered saline to a 96-well immobilizer amino plate (Nunc) at 100 μl/well and shaking the plate at room temperature for 2 hours. Blocking was performed by adding a 50 mM sodium bicarbonate buffer solution (pH 8.4) (hereafter, referred to as a "blocking solution") containing 0.5% BSA (bovine serum albumin, Sigma Aldrich Japan) at 100 μl/well, followed by shaking at room temperature for 1 hour. Thereafter, the serum samples obtained from cancer-bearing individuals diluted with a blocking solution were added at 100 μl/well and then subjected to the reaction via shaking at room temperature for 3 hours. The dilution rate at this time was adjusted with 10-fold dilution series (i.e., 10-1000-fold dilutions). The reaction product was washed 3 times with phosphate buffered saline containing 0.05% Tween 20 (Wako Pure Chemical Industries, Ltd.; this solution is referred to as "PBS-T" herein), each monoclonal antibody as a secondary antibody diluted to a concentration of 1 μg/ml with the blocking solution was added at 100 μl/well, and the resultant was then subjected to shaking at room temperature for 1 hour for reaction. The reaction product was washed 3 times with PBS-T, an HRP-labeled anti-mouse IgG (H+L) antibody (Invitrogen) as a tertiary antibody diluted 5000-fold with the blocking solution was added at 100 μl/well, and the resultant was then allowed to stand at room temperature for 1 hour. After each well was washed 3 times with PBS-T, a TMB substrate solution (Thermo) was added at 100 μl per/well, and the resultant was allowed to stand for 15 to 30 minutes, so as to allow the color to develop. Thereafter, 1N sulfuric acid was added at 100 μl/well to terminate the reaction. The absorbance was measured at 450 nm using an spectrophotometer.

When the monoclonal antibodies #1 to #10 reacting with the surfaces of cancer cells were used as secondary antibodies, as a result, high absorbance values were detected in all the dogs with pancreatic ductal carcinoma, although no absorbance was detected in healthy dogs. When monoclonal antibodies that react with the CAPRIN-1 proteins but do not react with the surfaces of cancer cells were used as secondary antibodies, polypeptide values were detected in all specimens. However, all the absorbance values were lower than the detection limit, which were lower than the results for combinations of antibodies reacting with the surfaces of cancer cells.

Therefore, cancer can also be diagnosed or examined by this technique that comprises detection of the CAPRIN-1 proteins using antibodies against CAPRIN-1.

(2) Diagnosis or Examination of Cancer by Measuring Antigenic Polypeptide on Pancreatic Cancer Tissue by Immunohistochemical Staining Immunohistochemical staining was performed using an array (BIOMAX) having 101 paraffin-embedded human pancreatic cancer tissue specimens. The array of human pancreatic cancer tissues was treated at 60° C. for 3 hours, the resultant was put in a staining bottle filled with xylene, xylene was replaced with fresh xylene every 5 minutes, and this procedure was repeated 3 times. Subsequently, a similar procedure was carried out using ethanol and PBS-T instead of xylene. The array of human pancreatic cancer tissues was put in a staining bottle filled with 10 mM citrate buffer (pH 6.0) containing 0.05% Tween 20, treated at 125° C. for 5 minutes, and then allowed to stand at room temperature for 40 minutes or longer. Excess water around each specimen was removed using Kimwipes, each section was encircled with DAKOPEN (DAKO), and an appropriate amount of Peroxidase Block (DAKO) was then added dropwise onto the array. The array was allowed to stand at room temperature for 5 minutes, the array was put in a staining bottle filled with PBS-T, and PBS-T was replaced with fresh PBS-T every 5 minutes. This procedure was performed 3 times. As a blocking solution, a PBS-T solution containing 10% FBS was applied onto the array, and the array was then allowed to stand in a moist chamber at room temperature for 1 hour. Subsequently, the monoclonal antibodies #1 to #10 prepared in Example 3 adjusted to 10 μg/ml with a PBS-T solution containing 5% FBS were applied onto the array, and the array was allowed to stand in a moist chamber at 4° C. overnight. After the array was washed with PBS-T for 10 minutes 3 times, an appropriate amount of Peroxidase Labeled Polymer Conjugated (DAKO) was added dropwise onto the array, and the array was allowed to stand in a moist chamber at room temperature for 30 minutes. After the array was washed with PBS-T for 10 minutes 3 times, a DAB color-developing solution (DAKO) was applied onto the array, and the array was then allowed to stand at room temperature for about 10 minutes. After the color-developing solution was discarded, the array was washed with PBS-T for 10 minutes 3 times, rinsed with distilled water, successively put in 70%, 80%, 90%, 95%, and 100% ethanol solutions for 1 minute each, and then allowed to stand in xylene overnight. The glass slides were removed, coverslipped with Glycergel Mounting Medium (DAKO), and then observed. As a result, CAPRIN-1 expression was observed in pancreatic cancer cell membranes and in pancreatic cancer cells in the pancreatic cancer tissue samples with the use of any antibodies. When immunohistochemical staining was carried out with the use of Antibody #8, for example, strong CAPRIN-1 expression was observed in 54 specimens among the total pancreatic cancer tissue specimens (101 specimens) (i.e., 54%).

Similarly, immunohistochemical staining was carried out using an array (BIOMAX) of paraffin-embedded normal human tissues including normal human pancreatic tissues. Excess water around each specimen was removed using Kimwipes, each section was encircled with DAKOPEN (DAKO), and an appropriate amount of Peroxidase Block (DAKO) was then added dropwise onto the array. The array was allowed to stand at room temperature for 5 minutes, the array was put in a staining bottle filled with PBS-T, and PBS-T was replaced with fresh PBS-T every 5 minutes. This procedure was performed 3 times. As a blocking solution, a PBS-T solution containing 10% FBS was applied onto the array, and the array was then allowed to stand in a moist chamber at room temperature for 1 hour. Subsequently, the monoclonal antibodies #1 to #10 prepared in Example 3 adjusted to 10 μg/ml in a PBS-T solution containing 5% FBS were applied onto the array, and the array was then allowed to stand in a moist chamber at 4° C. overnight. After the array was washed with PBS-T for 10 minutes 3 times, an appropriate amount of Peroxidase Labeled Polymer Conjugated (DAKO) was added dropwise onto the array, and the array was allowed to stand in a moist chamber at room temperature for 30 minutes. After the array was washed with PBS-T for 10 minutes 3 times, a DAB color-developing solution (DAKO) was applied onto the array, and the array was then allowed to stand at room temperature for about 10 minutes. After the color-developing solution was discarded, the array was washed with PBS-T for 10 minutes 3 times, rinsed with distilled water, successively put in 70%, 80%, 90%, 95%, and 100% ethanol solutions for 1 minute each, and then allowed to stand in xylene overnight. The glass slides were removed, coverslipped with Glycergel Mounting Medium (DAKO), and then observed. As a result, none of pancreas-derived normal tissue samples were stained and no CAPRIN-1 expression was observed, no matter what antibody was used.

INDUSTRIAL APPLICABILITY

The present invention is industrially useful for diagnosis or detection of pancreatic cancer.

All publications, patents, and patent applications cited herein are incorporated herein by reference in their entirety.

Free Text of Sequence Listing

SEQ ID NOs: 31 to 42: primers

The invention claimed is:

1. A method for detecting and treating pancreatic cancer in a human subject, comprising the following steps:

contacting a sample from the human subject with an antibody that specifically binds a human CAPRIN-1 protein expressed on the surface of a pancreatic cancer cell;

measuring an amount of a polypeptide bound to the antibody in the sample;

comparing the measured amount of the polypeptide with an amount of a control;

determining that the human subject has a pancreatic cancer when the amount of the polypeptide is higher than the amount of the control; and treating the human subject detennined to have pancreatic cancer by administration of an antibody that specifically binds a human CAPRIN-1 protein expressed on the surface of a pancreatic cancer cell, wherein the pancreatic cancer is a human CAPRIN-1 expressing pancreatic cancer, and wherein the sample is a pancreatic tissue or pancreatic cell sample.

2. The method according to claim 1, wherein the polypeptide to be measured is a human CAPRIN-1 protein consisting of an amino acid sequence represented by SEQ ID NO: 2 or SEQ ID NO: 4.

3. The method according to claim 1, wherein the measurement is an immunological assay.

4. The method according to claim 1, wherein the antibody specifically binds a region consisting of amino acid residues 50-98 or 233-305 in an amino acid sequence of SEQ ID NO: 2.

5. The method according to claim 1, wherein the antibody is a monoclonal antibody.

6. The method according to claim 1, wherein the antibody is a monoclonal antibody that specifically binds a region consisting of amino acid residues 50-98 or 233-305 in an amino acid sequence of SEQ ID NO: 2.

* * * * *

SEQUENCE LISTING

```
<160> NUMBER OF SEQ ID NOS: 63

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:
```

```
<400> SEQUENCE: 1

cagagggctg ctggctggct aagtccctcc cgctcccggc tctcgcctca ctaggagcgg     60

ctctcggtgc agcgggacag ggcgaagcgg cctgcgccca cggagcgcgc gacactgccc    120

ggaagggacc gccacccttg ccccctcagc tgcccactcg tgatttccag cggcctccgc    180

gcgcgcacg atg ccc tcg gcc acc agc cac agc ggg agc ggc agc aag tcg    231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac      375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285
```

```
agt gaa gtt gaa tca aca gag tat gta aat aga cag ttc atg gca gaa      1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt      1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca      1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca      1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg      1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat      1335
Gln Gly Pro Tyr Asn Phe Ile Gln Asp Ser Met Leu Asp Phe Glu Asn
            370                 375                 380

cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa      1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460

cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
```

```
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                675                 680                 685

cca cga ggt cgt gga ggg ccc cca aga ccc aac aga ggg atg ccg caa      2295
Pro Arg Gly Arg Gly Gly Pro Pro Arg Pro Asn Arg Gly Met Pro Gln
            690                 695                 700

atg aac act cag caa gtg aat taa tctgattcac aggattatgt ttaatcgcca     2349
Met Asn Thr Gln Gln Val Asn
        705

aaaacacact ggccagtgta ccataatatg ttaccagaag agttattatc tatttgttct    2409

ccctttcagg aaacttattg taaagggact gttttcatcc cataaagaca ggactacaat    2469

tgtcagcttt ctattacctg gatatggaag gaaactattt ttactctgca tgttctgtcc    2529

taagcgtcat cttgagcctt gcacatgata ctcagattcc tcacccttgc ttaggagtaa    2589

aacaatatac tttacagggt gataataatc tccatagtta tttgaagtgg cttgaaaaag    2649

gcaagattga cttttatgac attggataaa atctacaaat cagccctcga gttattcaat    2709

gataactgac aaactaaatt atttccctag aaaggaagat gaaaggagtg gagtgtggtt    2769

tggcagaaca actgcatttc acagcttttc cagttaaatt ggagcactga acgttcagat    2829

gcataccaaa ttatgcatgg gtcctaatca cacatataag gctggctacc agctttgaca    2889

cagcactgtt catctggcca aacaactgtg gttaaaaaca catgtaaaat gctttttaac    2949

agctgatact gtataagaca aagccaagat gcaaaattag gctttgattg gcactttttg    3009

aaaaatatgc aacaaatatg ggatgtaatc cggatggccg cttctgtact taatgtgaaa    3069

tatttagata cctttttgaa cacttaacag tttctttgag acaatgactt ttgtaaggat    3129

tggtactatc tatcattcct tatgacatgt acattgtctg tcactaatcc ttggattttg    3189

ctgtattgtc acctaaattg gtacaggtac tgatgaaaat ctctagtgga taatcataac    3249

actctcggtc acatgttttt ccttcagctt gaaagctttt ttttaaaagg aaaagatacc    3309

aaatgcctgc tgctaccacc cttttcaatt gctatctttt gaaaggcacc agtatgtgtt    3369

ttagattgat ttccctgttt cagggaaatc acggacagta gtttcagttc tgatggtata    3429

agcaaaacaa ataaaacgtt tataaaagtt gtatcttgaa acactggtgt tcaacagcta    3489

gcagcttatg tgattcaccc catgccacgt tagtgtcaca aattttatgg tttatctcca    3549

gcaacatttc tctagtactt gcacttatta tcttttgtct aatttaacct taactgaatt    3609

ctccgtttct cctggaggca tttatattca gtgataattc cttcccttag atgcataggg    3669

agagtctcta aatttgatgg aaatggacac ttgagtagtg acttagcctt atgtactctg    3729

ttggaatttg tgctagcagt ttgagcacta gttctgtgtg cctaggaagt taatgctgct    3789

tattgtctca ttctgacttc atggagaatt aatcccacct ttaagcaaag gctactaagt    3849
```

```
taatggtatt ttctgtgcag aaattaaatt ttattttcag catttagccc aggaattctt   3909

ccagtaggtg ctcagctatt taaaaacaaa actattctca aacattcatc attagacaac   3969

tggagttttt gctggttttg taacctacca aaatggatag gctgttgaac attccacatt   4029

caaaagtttt gtagggtggt gggaaatggg ggatcttcaa tgtttatttt aaaataaaat   4089

aaaataagtt cttgactttt ctcatgtgtg gttgtggtac atcatattgg aagggttaac   4149

ctgttacttt ggcaaatgag tatttttttg ctagcacctc cccttgcgtg ctttaaatga   4209

catctgcctg ggatgtacca caaccatatg ttacctgtat cttaggggaa tggataaaat   4269

atttgtggtt tactgggtaa tccctagatg atgtatgctt gcagtcctat ataaaactaa   4329

atttgctatc tgtgtagaaa ataatttcat gacatttaca atcaggactg aagtaagttc   4389

ttcacacagt gacctctgaa tcagtttcag agaagggatg gggagaaaa tgccttctag   4449

gttttgaact tctatgcatt agtgcagatg ttgtgaatgt gtaaaggtgt tcatagtttg   4509

actgtttcta tgtatgtttt ttcaaagaat tgttcctttt tttgaactat aatttttctt   4569

tttttggtta ttttaccatc acagtttaaa tgtatatctt ttatgtctct actcagacca   4629

tatttttaaa ggggtgcctc attatggggc agagaacttt tcaataagtc tcattaagat   4689

ctgaatcttg gttctaagca ttctgtataa tatgtgattg cttgtcctag ctgcagaagg   4749

ccttttgttt ggtcaaatgc atattttagc agagtttcaa ggaaatgatt gtcacacatg   4809

tcactgtagc ctcttggtgt agcaagctca catacaaaat acttttgtat atgcataata   4869

taaatcatct catgtggata tgaaacttct tttttaaaac ttaaaaaggt agaatgttat   4929

tgattacctt gattagggca gttttatttc cagatcctaa taattcctaa aaaatatgga   4989

aaagtttttt ttcaatcatt gtaccttgat attaaaacaa atatccttta agtatttcta   5049

atcagttagc ttctacagtt cttttgtctc cttttatatg cagctcttac gtgggagact   5109

tttccactta aaggagacat agaatgtgtg cttattctca gaaggttcat taactgaggt   5169

gatgagttaa caactagttg agcagtcagc ttcctaagtg ttttaggaca tttgttcatt   5229

atattttccg tcatataact agaggaagtg gaatgcagat aagtgccgaa ttcaaaccct   5289

tcattttatg tttaagctcc tgaatctgca ttccacttgg gttgttttta agcattctaa   5349

attttagttg attataagtt agatttcaca gaatcagtat tgcccttgat cttgtccttt   5409

ttatggagtt aacggggagg aagacccctc aggaaaacga aagtaaattg ttaaggctca   5469

tcttcatacc tttttccatt ttgaatccta caaaaatact gcaaaagact agtgaatgtt   5529

taaaattaca ctagattaaa taatatgaaa gtc                                5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60
```

-continued

```
Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
```

```
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705


<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)
<223> OTHER INFORMATION:

<400> SEQUENCE: 3

cagagggctg ctggctggct aagtccctcc cgctcccggc tctcgcctca ctaggagcgg      60

ctctcggtgc agcgggacag ggcgaagcgg cctgcgccca cggagcgcgc gacactgccc     120

ggaagggacc gccacccttg ccccctcagc tgcccactcg tgatttccag cggcctccgc     180

gcgcgcacg atg ccc tcg gcc acc agc cac agc ggg agc ggc agc aag tcg     231
          Met Pro Ser Ala Thr Ser His Ser Gly Ser Gly Ser Lys Ser
          1               5                   10

tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
15                  20                  25                  30

gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                35                  40                  45

ggc gct gtc cag acc gag gcc atg aag cag att ctc ggg gtg atc gac       375
Gly Ala Val Gln Thr Glu Ala Met Lys Gln Ile Leu Gly Val Ile Asp
            50                  55                  60

aag aaa ctt cgg aac ctg gag aag aaa aag ggt aag ctt gat gat tac       423
```

```
Lys Lys Leu Arg Asn Leu Glu Lys Lys Lys Gly Lys Leu Asp Asp Tyr
        65                  70                  75

cag gaa cga atg aac aaa ggg gaa agg ctt aat caa gat cag ctg gat      471
Gln Glu Arg Met Asn Lys Gly Glu Arg Leu Asn Gln Asp Gln Leu Asp
    80                  85                  90

gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110

gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125

ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140

cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155

ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170

gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190

aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205

tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220

aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235

cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250

ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270

cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285

agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300

aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315

gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330

tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350

gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365

cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380
```

```
cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395

caa aac atg gac atg ccc cag ctg gtt tgc cct cca gtt cat tct gaa      1431
Gln Asn Met Asp Met Pro Gln Leu Val Cys Pro Pro Val His Ser Glu
    400                 405                 410

tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430

cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445

ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460

cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475

aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480                 485                 490

gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510

gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525

cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540

gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555

aca gag ctt cag caa gaa cag ctt caa aca gtg gtt ggc act tac cat      1911
Thr Glu Leu Gln Gln Glu Gln Leu Gln Thr Val Val Gly Thr Tyr His
    560                 565                 570

ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590

cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605

agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610                 615                 620

aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625                 630                 635

tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640                 645                 650

cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655                 660                 665                 670

cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
                675                 680                 685

cca cga ggt aat att ttg tgg tgg tga tcctagctcc taagtggagc           2294
Pro Arg Gly Asn Ile Leu Trp Trp
            690
```

```
ttctgttctg gccttggaag agctgttaat agtctgcatg ttaggaatac atttatcctt   2354
tccagacttg ttgctaggga ttaaatgaaa tgctctgttt ctaaaactta atcttggacc   2414
caaattttaa tttttgaatg atttaatttt ccctgttact atataaactg tcttgaaaac   2474
tagaacatat tctcttctca gaaaaagtgt ttttccaact gaaaattatt tttcaggtcc   2534
taaaacctgc taaatgtttt taggaagtac ttactgaaac atttttgtaa gacatttttg   2594
gaatgagatt gaacatttat ataaatttat tattcctctt tcattttttt gaaacatgcc   2654
tattatattt tagggccaga caccctttaa tggccggata agccatagtt aacatttaga   2714
gaaccattta gaagtgatag aactaatgga atttgcaatg ccttttggac ctctattagt   2774
gatataaata tcaagttatt tctgactttt aaacaaaact cccaaattcc taacttattg   2834
agctatactt aaaaaaaatt acaggtttag agagtttttt gtttttcttt tactgttgga   2894
aaactacttc ccattttggc aggaagttaa cctatttaac aattagagct agcatttcat   2954
gtagtctgaa attctaaatg gttctctgat ttgagggagg ttaaacatca aacaggtttc   3014
ctctattggc cataacatgt ataaaatgtg tgttaaggag gaattacaac gtactttgat   3074
ttgaatacta gtagaaactg gccaggaaaa aggtacattt ttctaaaaat taatggatca   3134
cttgggaatt actgacttga ctagaagtat caaaggatgt ttgcatgtga atgtgggtta   3194
tgttctttcc caccttgtag catattcgat gaaagttgag ttaactgata gctaaaaatc   3254
tgttttaaca gcatgtaaaa agttatttta tctgttaaaa gtcattatac agttttgaat   3314
gttatgtagt ttctttttaa cagtttaggt aataaggtct gttttcattc tggtgctttt   3374
attaatttg atagtatgat gttacttact actgaaatgt aagctagagt gtacactaga   3434
atgtaagctc catgagagca ggtaccttgt ctgtcttctc tgctgtatct attcccaacg   3494
cttgatgatg gtgcctggca catagtaggc actcaataaa tatttgttga atgaatgaa    3553
```

<210> SEQ ID NO 4
<211> LENGTH: 694
<212> TYPE: PRT
<213> ORGANISM: Homo sapiens

<400> SEQUENCE: 4

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
    130                 135                 140

Arg Leu Lys Thr Val Leu Glu Leu Gln Tyr Val Leu Asp Lys Leu Gly
```

-continued

```
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
        195                 200                 205

His Ala Ser Ile His Leu Trp Asp Leu Leu Glu Gly Lys Glu Lys Pro
    210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
        275                 280                 285

Val Glu Ser Thr Glu Tyr Val Asn Arg Gln Phe Met Ala Glu Thr Gln
    290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
        355                 360                 365

Pro Tyr Asn Phe Ile Gln Asp Ser Met Leu Asp Phe Glu Asn Gln Thr
    370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575
```

```
Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690


<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)
<223> OTHER INFORMATION:

<400> SEQUENCE: 5

gtcacaaata acttggagtt tgcaaaagaa ttacagagga gtttc atg gca tta agt      57
                                                  Met Ala Leu Ser
                                                  1

caa gat att cag aaa aca ata aag aag act gca cgt cgg gag cag ctt       105
Gln Asp Ile Gln Lys Thr Ile Lys Lys Thr Ala Arg Arg Glu Gln Leu
5                   10                  15                  20

atg aga gag gaa gcg gaa caa aaa cgt tta aaa act gta ctt gag ctc       153
Met Arg Glu Glu Ala Glu Gln Lys Arg Leu Lys Thr Val Leu Glu Leu
                25                  30                  35

cag tat gtt ttg gac aaa ttg gga gat gat gaa gtg aga act gac ctg       201
Gln Tyr Val Leu Asp Lys Leu Gly Asp Asp Glu Val Arg Thr Asp Leu
            40                  45                  50

aag caa ggt ttg aat gga gtg cca ata ttg tct gaa gaa gaa ttg tcg       249
Lys Gln Gly Leu Asn Gly Val Pro Ile Leu Ser Glu Glu Glu Leu Ser
        55                  60                  65

ttg ttg gat gaa ttc tac aaa tta gca gac cct gaa cgg gac atg agc       297
Leu Leu Asp Glu Phe Tyr Lys Leu Ala Asp Pro Glu Arg Asp Met Ser
    70                  75                  80

ttg agg ttg aat gag cag tat gaa cat gct tcc att cac ctg tgg gac       345
Leu Arg Leu Asn Glu Gln Tyr Glu His Ala Ser Ile His Leu Trp Asp
85                  90                  95                  100

ttg ctg gaa gga aag gaa aag tct gta tgt gga aca acc tat aaa gca       393
Leu Leu Glu Gly Lys Glu Lys Ser Val Cys Gly Thr Thr Tyr Lys Ala
                105                 110                 115

cta aag gaa att gtt gag cgt gtt ttc cag tca aat tac ttt gac agc       441
Leu Lys Glu Ile Val Glu Arg Val Phe Gln Ser Asn Tyr Phe Asp Ser
            120                 125                 130

act cac aac cac cag aat ggg cta tgt gag gaa gaa gag gca gcc tca       489
Thr His Asn His Gln Asn Gly Leu Cys Glu Glu Glu Glu Ala Ala Ser
        135                 140                 145

gca cct aca gtt gaa gac cag gta gct gaa gct gag cct gag cca gca       537
Ala Pro Thr Val Glu Asp Gln Val Ala Glu Ala Glu Pro Glu Pro Ala
```

```
    150                 155                 160

gaa gaa tac act gaa caa agt gaa gtt gaa tca aca gag tat gta aat      585
Glu Glu Tyr Thr Glu Gln Ser Glu Val Glu Ser Thr Glu Tyr Val Asn
165                 170                 175                 180

aga caa ttt atg gca gaa aca cag ttc agc agt ggt gaa aag gag cag      633
Arg Gln Phe Met Ala Glu Thr Gln Phe Ser Ser Gly Glu Lys Glu Gln
                185                 190                 195

gta gat gag tgg acg gtc gaa aca gtg gag gtg gtg aat tca ctc cag      681
Val Asp Glu Trp Thr Val Glu Thr Val Glu Val Val Asn Ser Leu Gln
            200                 205                 210

cag caa cct cag gct gcg tct cct tca gta cca gag ccc cac tct ttg      729
Gln Gln Pro Gln Ala Ala Ser Pro Ser Val Pro Glu Pro His Ser Leu
        215                 220                 225

act ccg gtg gct cag gca gat ccc ctt gtg aga aga cag cga gtc cag      777
Thr Pro Val Ala Gln Ala Asp Pro Leu Val Arg Arg Gln Arg Val Gln
    230                 235                 240

gac ctt atg gcg cag atg cag ggg ccc tat aat ttc ata cag gat tca      825
Asp Leu Met Ala Gln Met Gln Gly Pro Tyr Asn Phe Ile Gln Asp Ser
245                 250                 255                 260

atg ctg gat ttt gaa aac cag aca ctc gat cct gcc att gta tct gca      873
Met Leu Asp Phe Glu Asn Gln Thr Leu Asp Pro Ala Ile Val Ser Ala
                265                 270                 275

cag cct atg aat ccg aca caa aac atg gac atg ccc cag ctg gtt tgc      921
Gln Pro Met Asn Pro Thr Gln Asn Met Asp Met Pro Gln Leu Val Cys
            280                 285                 290

cct cca gtt cat tct gaa tct aga ctt gct caa cct aat caa gtt cct      969
Pro Pro Val His Ser Glu Ser Arg Leu Ala Gln Pro Asn Gln Val Pro
        295                 300                 305

gta caa cca gaa gct aca cag gtt cct ttg gtt tca tcc aca agt gag     1017
Val Gln Pro Glu Ala Thr Gln Val Pro Leu Val Ser Ser Thr Ser Glu
    310                 315                 320

ggg tat aca gca tct caa ccc ttg tac cag cct tct cat gct aca gag     1065
Gly Tyr Thr Ala Ser Gln Pro Leu Tyr Gln Pro Ser His Ala Thr Glu
325                 330                 335                 340

caa cga cca caa aag gaa cca att gac cag att cag gca aca atc tct     1113
Gln Arg Pro Gln Lys Glu Pro Ile Asp Gln Ile Gln Ala Thr Ile Ser
                345                 350                 355

tta aat aca gac cag act aca gcg tca tca tcc ctt ccg gct gct tct     1161
Leu Asn Thr Asp Gln Thr Thr Ala Ser Ser Ser Leu Pro Ala Ala Ser
            360                 365                 370

cag cct cag gta ttc cag gct ggg aca agc aaa cca tta cat agc agt     1209
Gln Pro Gln Val Phe Gln Ala Gly Thr Ser Lys Pro Leu His Ser Ser
        375                 380                 385

gga atc aat gta aat gca gct cca ttc caa tcc atg caa acg gtg ttc     1257
Gly Ile Asn Val Asn Ala Ala Pro Phe Gln Ser Met Gln Thr Val Phe
    390                 395                 400

aat atg aat gcc cca gtt cct cct gtt aat gaa cca gaa act ttg aaa     1305
Asn Met Asn Ala Pro Val Pro Pro Val Asn Glu Pro Glu Thr Leu Lys
405                 410                 415                 420

caa caa aat cag tac cag gcc agt tat aac cag agc ttt tct agt cag     1353
Gln Gln Asn Gln Tyr Gln Ala Ser Tyr Asn Gln Ser Phe Ser Ser Gln
                425                 430                 435

cct cac caa gta gaa caa aca gag gga tgc cgc aaa tga acactcagca      1402
Pro His Gln Val Glu Gln Thr Glu Gly Cys Arg Lys
            440                 445

agtgaattaa tctgattcac aggattatgt ttaaacgcca aaaacacact ggccagtgta   1462

ccataatatg ttaccagaag agttattatc tatttgttct ccctttcagg aaacttattg   1522

taaagggact gttttcatcc cataaagaca ggactacaat tgtcagcttt atattacctg   1582
```

```
gaaaaaaaaa aaaaaaaaaa aaa                                            1605


<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
        275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
        355                 360                 365
```

```
Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
        435                 440                 445


<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 7

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205
```

```
ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
```

```
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttgttct ccctttcagg aaacttattg taaagggact   2274

gttttcatcc cataaagaca ggactacaat tgtcagcttt atattacctg gatatggaag   2334

gaaactattt ttattctgca tgttcttcct aagcgtcatc ttgagccttg cacatgatac   2394

tcagattcct caccccttgct taggagtaaa acataataca ctttacaggg tgatatctcc  2454

atagttattt gaagtggctt ggaaaaagca agattaactt ctgacattgg ataaaaatca   2514

acaaatcagc cctagagtta ttcaaatggt aattgacaaa aactaaaata tttcccttcg   2574

agaaggagtg gaatgtggtt tggcagaaca actgcatttc acagcttttc cggttaaatt   2634

ggagcactaa acgtttagat gcataccaaa ttatgcatgg gcccttaata taaaaggctg   2694

gctaccagct ttgacacagc actattcatc ctctggccaa acaactgtgg ttaaacaaca   2754

catgtaaatt gctttttaac agctgatact ataataagac aaagccaaaa tgcaaaaatt   2814

gggctttgat tggcactttt tgaaaaatat gcaacaaata tgggatgtaa tctggatggc   2874

cgcttctgta cttaatgtga agtatttaga tacctttttg aacacttaac agtttcttct   2934

gacaatgact tttgtaagga ttggtactat ctatcattcc ttataatgta cattgtctgt   2994

cactaatcct cagatcttgc tgtattgtca cctaaattgg tacaggtact gatgaaaata   3054
```

```
tctaatggat aatcataaca ctcttggtca catgtttttc ctgcagcctg aaggttttta   3114

aaagaaaaag atatcaaatg cctgctgcta ccacccttt aaattgctat cttttgaaaa   3174

gcaccagtat gtgttttaga ttgatttccc tattttaggg aaatgacaga cagtagtttc   3234

agttctgatg gtataagcaa aacaaataaa acatgtttat aaaagttgta tcttgaaaca   3294

ctggtgttca acagctagca gcttatgtgg ttcaccccat gcattgttag tgtttcagat   3354

tttatggtta tctccagcag ctgtttctgt agtacttgca tttatctttt gtctaaccct   3414

aatattctca cggaggcatt tatattcaaa gtggtgatcc cttcacttag acgcataggg   3474

agagtcacaa gtttgatgaa gaggacagtg tagtaattta tatgctgttg gaatttgtgc   3534

tagcagtttg agcactagtt ctgtgtgcct atgaacttaa tgctgcttgt catattccac   3594

tttgacttca tggagaatta atcccatcta ctcagcaaag gctatactaa tactaagtta   3654

atggtatttt ctgtgcagaa attgaatttt gttttattag catttagcta aggaattttt   3714

ccagtaggtg ctcagctact aaagaaaaac aaaaacaaga cacaaaacta ttctcaaaca   3774

ttcattgtta gacaactgga gtttttgctg gttttgtaac ctactaaaat ggataggctg   3834

ttgaacattc cacattcaaa agttttttgt agggtggtgg ggaagggggg gtgtcttcaa   3894

tgtttatttt aaaataaaat aagttcttga cttttctcat gtgtggttgt ggtacatcat   3954

attggaaggg ttatctgttt acttttgcaa atgagtattt ctcttgctag cacctcccgt   4014

tgtgcgcttt aaatgacatc tgcctgggat gtaccacaac catatgttag ctgtatttta   4074

tggggaatag ataaaatatt cgtggtttat tgggtaatcc ctagatgtgt atgcttacaa   4134

tcctatatat aaaactaaat                                                4154


<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175
```

```
Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590
```

```
Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)
<223> OTHER INFORMATION:

<400> SEQUENCE: 9

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175
```

```
aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
```

```
                485                 490                 495

cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc      1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc      1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
        675                 680                 685

agt gga cca cgg gga gcc cca cga ggt aat att ttg tgg tgg tga          2109
Ser Gly Pro Arg Gly Ala Pro Arg Gly Asn Ile Leu Trp Trp
    690                 695                 700

tcctagctcc taagtggagc ttctgttctg gccttggaag agctgttcca tagtctgcat    2169

gtaggttaca tgttaggaat acatttatca ttaccagact tgttgctagg gattaaatga    2229

aatgctctgt ttctaaaact tctcttgaac ccaaatttaa tttttgaat gactttccct     2289

gttactatat aaattgtctt gaaaactaga acatttctcc tcctcagaaa aagtgtttttt   2349

ccaactgcaa attatttttc aggtcctaaa acctgctaaa tgtttttagg aagtacttac    2409

tgaaacattt ttgtaagaca tttttggaat gagattgaac atttatataa atttattatt    2469

attcctcttt catttttgaa catgcatatt atattttagg gtcagaaatc ctttaatggc    2529

caaataagcc atagttacat ttagagaacc atttagaagt gatagaacta actgaaattt    2589

caatgccttt ggatcattaa tagcgatata aatttcaaat tgtttctgac ttttaaataa    2649

aacatccaaa atcctaacta acttcctgaa ctatatttaa aaattacagg tttaaggagt    2709

ttctggtttt ttttctctta ccataggaaa actgtttcct gtttggccag gaagtcaacc    2769

tgtgtaataa ttagaagtag catttcatat gatctgaagt tctaaatggt tctctgattt    2829

aagggaagtt aaattgaata ggtttcctct agttattggc cataacatgt ataaaatgta    2889
```

```
tattaaggag gaatacaaag tactttgatt tcaatgctag tagaaactgg ccagcaaaaa   2949
ggtgcatttt atttttaaat taatggatca cttgggaatt actgacttga agtatcaaag   3009
gatatttgca tgtgaatgtg ggttatgttc tttctcacct tgtagcatat tctatgaaag   3069
ttgagttgac tggtagctaa aaatctgttt taacagcatg taaaaagtta ttttatctgt   3129
tacaagtcat tatacaattt tgaatgttat gtagtttctt tttaacagtt taggtaacaa   3189
ggtctgtttt tcattctggt gcttttatta attttgatag tatgatgtta cttactactg   3249
aaatgtaagc tagagtgtac actagaatgt aagctccatg agagcaggta ccttgtctgt   3309
cttcactgct gtatctattt ccaacgcctg atgacagtgc ctgacacata gtaggcactc   3369
aataaatact tgttgaatga atgaatgaat gagtactggt ggaatactcc attagctcta   3429
ctcttctttt agctagagaa catgagcaaa tttgcgcatg acaacttcca ggacaggtga   3489
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact atttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttggaaaa agcaagatta   4029
acttctgaca ttggataaaa atcaacaaat cagccctaga gttattcaaa tggtaattga   4089
caaaaactaa aatatttccc ttcgagaagg agtggaatgt ggtttggcag aacaactgca   4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagatacctt   4449
tttgaacact taacagtttc ttctgacaat gacttttgta aggattggta ctatctatca   4509
ttccttataa tgtacattgt ctgtcactaa tcctcagatc ttgctgtatt gtcacctaaa   4569
ttggtacagg tactgatgaa aatatctaat ggataatcat aacactcttg gtcacatgtt   4629
tttcctgcag cctgaaggtt tttaaaagaa aaagatatca aatgcctgct gctaccaccc   4689
ttttaaattg ctatcttttg aaaagcacca gtatgtgttt tagattgatt tccctatttt   4749
agggaaatga cagacagtag tttcagttct gatggtataa gcaaaacaaa taaaacatgt   4809
ttataaaagt tgtatcttga aacactggtg ttcaacagct agcagcttat gtggttcacc   4869
ccatgcattg ttagtgtttc agattttatg gttatctcca gcagctgttt ctgtagtact   4929
tgcatttatc                                                          4939
```

<210> SEQ ID NO 10
<211> LENGTH: 702
<212> TYPE: PRT
<213> ORGANISM: Canis familiaris

<400> SEQUENCE: 10

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
```

```
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Asn Ile Leu Trp Trp
    690                 695                 700


<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)
<223> OTHER INFORMATION:

<400> SEQUENCE: 11

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
```

```
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
```

```
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gga tgc cgc aaa tga acactcagca agtgaattaa tctgattcac     2070
Tyr Gln Arg Gly Cys Arg Lys
        675
```

```
aggattatgt ttaaacgcca aaaacacact ggccagtgta ccataaatatg ttaccagaag   2130
agttattatc tatttgttct ccctttcagg aaacttattg taaagggact gttttcatcc   2190
cataaagaca ggactacaat tgtcagcttt atattacctg gatatggaag gaaactattt   2250
ttattctgca tgttcttcct aagcgtcatc ttgagccttg cacatgatac tcagattcct   2310
caccccttgct taggagtaaa acataataca ctttacaggg tgatatctcc atagttattt   2370
gaagtggctt ggaaaaagca agattaactt ctgacattgg ataaaaatca acaaatcagc   2430
cctagagtta ttcaaatggt aattgacaaa aactaaaata tttcccttcg agaaggagtg   2490
gaatgtggtt tggcagaaca actgcatttc acagcttttc cggttaaatt ggagcactaa   2550
acgtttagat gcataccaaa ttatgcatgg gcccttaata taaaaggctg gctaccagct   2610
ttgacacagc actattcatc ctctggccaa acaactgtgg ttaaacaaca catgtaaatt   2670
gctttttaac agctgatact ataataagac aaagccaaaa tgcaaaaatt gggctttgat   2730
tggcactttt tgaaaaatat gcaacaaata tgggatgtaa tctggatggc cgcttctgta   2790
cttaatgtga agtatttaga taccttttg aacacttaac agtttcttct gacaatgact   2850
tttgtaagga ttggtactat ctatcattcc ttataatgta cattgtctgt cactaatcct   2910
cagatcttgc tgtattgtca cctaaattgg tacaggtact gatgaaaata tctaatggat   2970
aatcataaca ctcttggtca catgtttttc ctgcagcctg aaggttttta aaagaaaaag   3030
atatcaaatg cctgctgcta ccaccctttt aaattgctat cttttgaaaa gcaccagtat   3090
gtgttttaga ttgatttccc tattttaggg aaatgacaga cagtagtttc agttctgatg   3150
gtataagcaa aacaaataaa acatgtttat aaaagttgta tcttgaaaca ctggtgttca   3210
acagctagca gcttatgtgg ttcaccccat gcattgttag tgtttcagat tttatggtta   3270
tctccagcag ctgtttctgt agtacttgca tttatc                              3306
```

```
<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160
```

```
Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575
```

```
Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
        675


<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 13

atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15

ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
            20                  25                  30

ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
        35                  40                  45

cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60

atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80

ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95

aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110

aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125

caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140

atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160

cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175

aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
```

```
            180                 185                 190

ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205

ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220

ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240

cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255

act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270

gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285

gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300

aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320

gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335

cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350

act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365

gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380

atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400

cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415

cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430

gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445

ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460

caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480

tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495

cag cct cag gta ttc cag gct ggg aca agc aaa cca tta cat agc agt     1536
```

```
Gln Pro Gln Val Phe Gln Ala Gly Thr Ser Lys Pro Leu His Ser Ser
            500                 505                 510

gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525

aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540

caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560

cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575

gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590

ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605

agt cag ccc tat tac aat agt cgt ggt gtg tct cgt ggt ggt tcc cgt     1872
Ser Gln Pro Tyr Tyr Asn Ser Arg Gly Val Ser Arg Gly Gly Ser Arg
    610                 615                 620

ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640

aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655

agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670

tat cag cgg gat gga tat cag cag aat ttc aag cga ggc tct ggg cag     2064
Tyr Gln Arg Asp Gly Tyr Gln Gln Asn Phe Lys Arg Gly Ser Gly Gln
        675                 680                 685

agt gga cca cgg gga gcc cca cga ggt cgt gga ggg ccc cca aga ccc     2112
Ser Gly Pro Arg Gly Ala Pro Arg Gly Arg Gly Gly Pro Pro Arg Pro
    690                 695                 700

aac aga ggg atg ccg caa atg aac act cag caa gtg aat taa             2154
Asn Arg Gly Met Pro Gln Met Asn Thr Gln Gln Val Asn
705                 710                 715

tctgattcac aggattatgt ttaaacgcca aaaacacact ggccagtgta ccataatatg   2214

ttaccagaag agttattatc tatttggact gttttcatcc cataaagaca ggactacaat   2274

tgtcagc                                                             2281


<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
```

```
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Glu Ala Ala Ser
            260                 265                 270

Ala Pro Thr Val Glu Asp Gln Val Ala Glu Ala Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480
```

```
Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715


<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)
<223> OTHER INFORMATION:

<400> SEQUENCE: 15

cgcgtctcgc cccgtccacc gattgactcg ccgctcttgt ccttcctccc gctctttctt      60

ctctcccctt acggtttcaa g atg cct tcg gcc acc agc cac agc gga agc      111
                        Met Pro Ser Ala Thr Ser His Ser Gly Ser
                        1               5                   10

ggc agc aag tcg tcc gga ccg cca ccg ccg tcg ggt tcc tcc ggg aat      159
Gly Ser Lys Ser Ser Gly Pro Pro Pro Pro Ser Gly Ser Ser Gly Asn
                15                  20                  25

gag gcg ggg gcc ggg gcc gcc gcg ccg gct tcc caa cac ccc atg acc      207
Glu Ala Gly Ala Gly Ala Ala Ala Pro Ala Ser Gln His Pro Met Thr
            30                  35                  40

ggc acc ggg gct gtc cag acc gag gcc atg aag cag att ctc ggg gtg      255
Gly Thr Gly Ala Val Gln Thr Glu Ala Met Lys Gln Ile Leu Gly Val
        45                  50                  55

atc gac aag aaa ctt cgg aac ctg gag aag aaa aag ggc aag ctt gat      303
Ile Asp Lys Lys Leu Arg Asn Leu Glu Lys Lys Lys Gly Lys Leu Asp
    60                  65                  70
```

```
gat tat cag gaa cga atg aac aaa ggg gaa agg ctt aat caa gat cag      351
Asp Tyr Gln Glu Arg Met Asn Lys Gly Glu Arg Leu Asn Gln Asp Gln
75                  80                  85                  90

ctg gat gcc gtg tct aag tac cag gaa gtc aca aat aac ttg gag ttt      399
Leu Asp Ala Val Ser Lys Tyr Gln Glu Val Thr Asn Asn Leu Glu Phe
                95                  100                 105

gca aaa gaa tta cag agg agt ttc atg gca tta agc caa gat att cag      447
Ala Lys Glu Leu Gln Arg Ser Phe Met Ala Leu Ser Gln Asp Ile Gln
            110                 115                 120

aaa aca ata aag aag aca gca cgt cgg gag cag ctt atg aga gag gaa      495
Lys Thr Ile Lys Lys Thr Ala Arg Arg Glu Gln Leu Met Arg Glu Glu
        125                 130                 135

gct gaa cag aaa cgt tta aaa aca gta ctt gag ctg cag tat gtt ttg      543
Ala Glu Gln Lys Arg Leu Lys Thr Val Leu Glu Leu Gln Tyr Val Leu
    140                 145                 150

gac aaa cta gga gat gat gaa gtg aga act gac ctg aag caa ggt ttg      591
Asp Lys Leu Gly Asp Asp Glu Val Arg Thr Asp Leu Lys Gln Gly Leu
155                 160                 165                 170

aat gga gtg cca ata ttg tct gaa gag gag ttg tcg ttg tta gat gag      639
Asn Gly Val Pro Ile Leu Ser Glu Glu Glu Leu Ser Leu Leu Asp Glu
                175                 180                 185

ttc tac aaa tta gca gac cct gaa cga gac atg agc ttg agg ttg aat      687
Phe Tyr Lys Leu Ala Asp Pro Glu Arg Asp Met Ser Leu Arg Leu Asn
            190                 195                 200

gag cag tat gaa cat gcc tcc att cac ctg tgg gac ttg ctg gaa gga      735
Glu Gln Tyr Glu His Ala Ser Ile His Leu Trp Asp Leu Leu Glu Gly
        205                 210                 215

aag gaa aaa cct gta tgt gga aca act tat aaa gct cta aag gaa att      783
Lys Glu Lys Pro Val Cys Gly Thr Thr Tyr Lys Ala Leu Lys Glu Ile
    220                 225                 230

gtt gag cgt gtt ttc cag tca aac tac ttt gac agc acc cac aac cac      831
Val Glu Arg Val Phe Gln Ser Asn Tyr Phe Asp Ser Thr His Asn His
235                 240                 245                 250

cag aat ggt ctg tgt gag gaa gag gag gca gcc tca gca cct aca gtt      879
Gln Asn Gly Leu Cys Glu Glu Glu Glu Ala Ala Ser Ala Pro Thr Val
                255                 260                 265

gaa gac cag gca gct gaa gct gaa cct gag cca gtg gaa gaa tat act      927
Glu Asp Gln Ala Ala Glu Ala Glu Pro Glu Pro Val Glu Glu Tyr Thr
            270                 275                 280

gaa caa aat gag gtt gaa tca aca gag tat gta aat aga caa ttt atg      975
Glu Gln Asn Glu Val Glu Ser Thr Glu Tyr Val Asn Arg Gln Phe Met
        285                 290                 295

gca gaa aca cag ttc agc agt ggt gaa aag gag cag gta gat gat tgg     1023
Ala Glu Thr Gln Phe Ser Ser Gly Glu Lys Glu Gln Val Asp Asp Trp
    300                 305                 310

aca gtt gaa aca gtt gag gtg gta aat tca ctc cag cag caa cct cag     1071
Thr Val Glu Thr Val Glu Val Val Asn Ser Leu Gln Gln Gln Pro Gln
315                 320                 325                 330

gct gca tct cct tca gta cca gaa ccc cac tct ttg acc cca gtg gct     1119
Ala Ala Ser Pro Ser Val Pro Glu Pro His Ser Leu Thr Pro Val Ala
                335                 340                 345

caa gcc gat ccc ctc gtg aga aga cag cga gta cag gac ctt atg gca     1167
Gln Ala Asp Pro Leu Val Arg Arg Gln Arg Val Gln Asp Leu Met Ala
            350                 355                 360

caa atg cag ggg ccc tat aat ttc ata cag gat tca atg ttg gat ttt     1215
Gln Met Gln Gly Pro Tyr Asn Phe Ile Gln Asp Ser Met Leu Asp Phe
        365                 370                 375

gaa aac cag aca ctt gat cct gcc att gta tct gca cag ccg atg aat     1263
Glu Asn Gln Thr Leu Asp Pro Ala Ile Val Ser Ala Gln Pro Met Asn
```

```
    380                 385                 390

cca gca cag aac atg gac ata ccc cag ctg gtt tgc cct cca gtt cat      1311
Pro Ala Gln Asn Met Asp Ile Pro Gln Leu Val Cys Pro Pro Val His
395                 400                 405                 410

tct gaa tct aga ctt gct caa cct aat caa gtt tct gta cag cca gaa      1359
Ser Glu Ser Arg Leu Ala Gln Pro Asn Gln Val Ser Val Gln Pro Glu
                415                 420                 425

gct aca cag gtt cct ttg gtt tca tcc aca agt gag gga tat aca gca      1407
Ala Thr Gln Val Pro Leu Val Ser Ser Thr Ser Glu Gly Tyr Thr Ala
            430                 435                 440

tct caa ccc ttg tac caa cct tct cat gct act gac caa cga cca caa      1455
Ser Gln Pro Leu Tyr Gln Pro Ser His Ala Thr Asp Gln Arg Pro Gln
        445                 450                 455

aag gaa ccg att gat cag att cag gcg acg atc tct tta aat aca gac      1503
Lys Glu Pro Ile Asp Gln Ile Gln Ala Thr Ile Ser Leu Asn Thr Asp
    460                 465                 470

cag act aca gca tca tca tcc ctt cct gct gct tct cag cct caa gtg      1551
Gln Thr Thr Ala Ser Ser Ser Leu Pro Ala Ala Ser Gln Pro Gln Val
475                 480                 485                 490

ttc cag gct ggg aca agc aaa cct tta cat agc agt gga atc aat gta      1599
Phe Gln Ala Gly Thr Ser Lys Pro Leu His Ser Ser Gly Ile Asn Val
                495                 500                 505

aat gca gct cca ttc caa tcc atg caa acg gta ttc aat atg aat gcc      1647
Asn Ala Ala Pro Phe Gln Ser Met Gln Thr Val Phe Asn Met Asn Ala
            510                 515                 520

cca gtt cct cct gtt aat gaa cca gaa act tta aaa cag caa aat cag      1695
Pro Val Pro Pro Val Asn Glu Pro Glu Thr Leu Lys Gln Gln Asn Gln
        525                 530                 535

tac cag gcc agt tac aac cag agc ttt tcc agt cag cct cac caa gta      1743
Tyr Gln Ala Ser Tyr Asn Gln Ser Phe Ser Ser Gln Pro His Gln Val
    540                 545                 550

gaa caa aca gag ctt cag caa gaa cag ctt caa aca gtg gtt ggc act      1791
Glu Gln Thr Glu Leu Gln Gln Glu Gln Leu Gln Thr Val Val Gly Thr
555                 560                 565                 570

tat cat ggt tct cag gac cag ccc cat caa gtg act ggt aac cac cag      1839
Tyr His Gly Ser Gln Asp Gln Pro His Gln Val Thr Gly Asn His Gln
                575                 580                 585

cag cct cct cag cag aac act gga ttt cca cgt agc aat cag ccc tat      1887
Gln Pro Pro Gln Gln Asn Thr Gly Phe Pro Arg Ser Asn Gln Pro Tyr
            590                 595                 600

tac aac agt cgt ggt gtg tct cgt gga ggt tcc cgt ggt gct aga ggc      1935
Tyr Asn Ser Arg Gly Val Ser Arg Gly Gly Ser Arg Gly Ala Arg Gly
        605                 610                 615

ttg atg aat gga tac aga gga cct gct aat gga ttc aga gga gga tat      1983
Leu Met Asn Gly Tyr Arg Gly Pro Ala Asn Gly Phe Arg Gly Gly Tyr
    620                 625                 630

gat ggt tac cgc cct tca ttc tct act aac act cca aac agt ggt tat      2031
Asp Gly Tyr Arg Pro Ser Phe Ser Thr Asn Thr Pro Asn Ser Gly Tyr
635                 640                 645                 650

aca caa tct caa ttc agt gct ccc cgg gac tac tct ggc tat cag cgg      2079
Thr Gln Ser Gln Phe Ser Ala Pro Arg Asp Tyr Ser Gly Tyr Gln Arg
                655                 660                 665

gat gga tat cag cag aat ttc aag cga ggc tct ggg cag agt gga cca      2127
Asp Gly Tyr Gln Gln Asn Phe Lys Arg Gly Ser Gly Gln Ser Gly Pro
            670                 675                 680

cgg gga gcc cca cga ggt cgt gga ggg ccc cca aga ccc aac aga ggg      2175
Arg Gly Ala Pro Arg Gly Arg Gly Gly Pro Pro Arg Pro Asn Arg Gly
        685                 690                 695

atg ccg caa atg aac act cag caa gtg aat taa tctgattcac aggattatgt   2228
```

```
Met Pro Gln Met Asn Thr Gln Gln Val Asn
    700                 705

ttaatcgcca aaaacacact ggccagtgta ccataatatg ttaccagaag agttattatc   2288

tatttgttct ccctttcagg aaacttattg taaagggact gttttcatcc cataaagaca   2348

ggactacaat tgtcagcttt atattacctg gatatggaag gaaactattt ttactctgca   2408

tgttctgtcc taagcgtcat cttgagcctt gcacatgata ctcagattcc tcacccttgc   2468

ttaggagtaa aacataatat actttaatgg ggtgatatct ccatagttat ttgaagtggc   2528

ttggataaag caagactgac ttctgacatt ggataaaatc tacaaatcag ccctagagtc   2588

attcagtggt aactgacaaa actaaaatat ttcccttgaa aggaagatgg aaggagtgga   2648

gtgtggtttg gcagaacaac tgcatttcac agcttttcca cttaaattgg agcactgaac   2708

atttagatgc ataccgaatt atgcatgggc cctaatcaca cagacaaggc tggtgccagc   2768

cttaggcttg acacggcagt gttcaccctc tggccagacg actgtggttc aagacacatg   2828

taaattgctt tttaacagct gatactgtat aagacaaagc caaaatgcaa aattaggctt   2888

tgattggcac ttttcgaaaa atatgcaaca attaagggat ataatctgga tggccgcttc   2948

tgtacttaat gtgaaatatt tagatacctt tcaaacactt aacagtttct ttgacaatga   3008

gttttgtaag gattggtagt aaatatcatt ccttatgacg tacattgtct gtcactaatc   3068

cttggatctt gctgtattgt cacctaaatt ggtacaggta ctgatgaaaa tctaatggat   3128

aatcataaca ctcttggtta catgtttttc ctgcagcctg aaagttttta taagaaaaag   3188

acatcaaatg cctgctgctg ccaccctttt aaattgctat cttttgaaaa gcaccagtat   3248

gtgttttaga ttgatttccc tattttaggg aaatgacagt cagtagtttc acttctgatg   3308

gtataagcaa acaaataaaa catgtttata aaaaaaaaaa aaaaaaaaaa aaaaaaaaaa   3368

aaaaaaaaaa aaaaaaaa                                                 3386


<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
```

```
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575
```

```
Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700

Gln Gln Val Asn
705


<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)
<223> OTHER INFORMATION:

<400> SEQUENCE: 17

atg gag ggc aag ctc gat gat tac caa gag cga atg aac aaa gga gaa       48
Met Glu Gly Lys Leu Asp Asp Tyr Gln Glu Arg Met Asn Lys Gly Glu
1               5                   10                  15

agg ctt aat cag gat cag ctg gat gct gtg tct aag tac cag gaa gtc       96
Arg Leu Asn Gln Asp Gln Leu Asp Ala Val Ser Lys Tyr Gln Glu Val
            20                  25                  30

aca aat aac ttg gag ttt gcg aaa gaa ttg cag agg agt ttc atg gcg      144
Thr Asn Asn Leu Glu Phe Ala Lys Glu Leu Gln Arg Ser Phe Met Ala
        35                  40                  45

ttg agt cag gat att cag aaa aca ata aag aag acg gca cgt cgg gag      192
Leu Ser Gln Asp Ile Gln Lys Thr Ile Lys Lys Thr Ala Arg Arg Glu
    50                  55                  60

cag ctt atg aga gaa gaa gct gaa cag aaa cgt tta aaa act gta ctt      240
Gln Leu Met Arg Glu Glu Ala Glu Gln Lys Arg Leu Lys Thr Val Leu
65                  70                  75                  80

gag ctg cag tat gtt ttg gac aaa ttg gga gat gaa gaa gtg cga act      288
Glu Leu Gln Tyr Val Leu Asp Lys Leu Gly Asp Glu Glu Val Arg Thr
                85                  90                  95

gac ctg aaa caa ggt ttg aat gga gtg cca ata ctc tct gaa gaa gag      336
Asp Leu Lys Gln Gly Leu Asn Gly Val Pro Ile Leu Ser Glu Glu Glu
            100                 105                 110

ttg tcg ctg ttg gat gag ttc tac aag tta gca gac cct gta cgg gac      384
Leu Ser Leu Leu Asp Glu Phe Tyr Lys Leu Ala Asp Pro Val Arg Asp
        115                 120                 125

atg agc ttg agg ttg aat gag cag tat gag cat gcc tcc att cac ctg      432
Met Ser Leu Arg Leu Asn Glu Gln Tyr Glu His Ala Ser Ile His Leu
    130                 135                 140

tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160
```

```
aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175

gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190

acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205

cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220

gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240

cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255

cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270

ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285

cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300

tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320

gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335

tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350

cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365

gag ggg tat aca gca tct cag ccc ttg tac cag cct tct cat gct aca     1152
Glu Gly Tyr Thr Ala Ser Gln Pro Leu Tyr Gln Pro Ser His Ala Thr
    370                 375                 380

gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400

tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415

tct cag cct cag gtg ttc cag gct ggg aca agc aaa cct tta cac agc     1296
Ser Gln Pro Gln Val Phe Gln Ala Gly Thr Ser Lys Pro Leu His Ser
            420                 425                 430

agt ggg atc aat gta aat gca gcg cca ttc cag tcc atg caa acg gtg     1344
Ser Gly Ile Asn Val Asn Ala Ala Pro Phe Gln Ser Met Gln Thr Val
        435                 440                 445

ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460

aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
```

```
465                 470                 475                 480

ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495

acg gtg gtt ggt act tac cat gct tcc caa gac cag ccc cat caa gtg     1536
Thr Val Val Gly Thr Tyr His Ala Ser Gln Asp Gln Pro His Gln Val
            500                 505                 510

acc ggt aac cac cag cag cct ccc cag cag aac act ggg ttt cca cgt     1584
Thr Gly Asn His Gln Gln Pro Pro Gln Gln Asn Thr Gly Phe Pro Arg
        515                 520                 525

agc agt cag ccc tat tac aac agt cgt ggt gtg tct cgt gga ggc tcc     1632
Ser Ser Gln Pro Tyr Tyr Asn Ser Arg Gly Val Ser Arg Gly Gly Ser
    530                 535                 540

cgt ggt gct aga ggc ttg atg aat gga tac agg ggc cct gcc aat gga     1680
Arg Gly Ala Arg Gly Leu Met Asn Gly Tyr Arg Gly Pro Ala Asn Gly
545                 550                 555                 560

ttc aga gga gga tat gat ggt tac cgc cct tcg ttc tct aac act cca     1728
Phe Arg Gly Gly Tyr Asp Gly Tyr Arg Pro Ser Phe Ser Asn Thr Pro
                565                 570                 575

aac agc ggt tac aca cag tct cag ttc agt gct ccc cgg gac tac tct     1776
Asn Ser Gly Tyr Thr Gln Ser Gln Phe Ser Ala Pro Arg Asp Tyr Ser
            580                 585                 590

ggc tat cag cgg gat gga tat cag cag aat ttc aag cga ggc tct ggg     1824
Gly Tyr Gln Arg Asp Gly Tyr Gln Gln Asn Phe Lys Arg Gly Ser Gly
        595                 600                 605

cag agt gga ccc cgg gga gcc cca cga ggt cgt gga ggg ccc cca aga     1872
Gln Ser Gly Pro Arg Gly Ala Pro Arg Gly Arg Gly Gly Pro Pro Arg
    610                 615                 620

ccc aac aga ggg atg ccg caa atg aac act cag caa gtg aat taa         1917
Pro Asn Arg Gly Met Pro Gln Met Asn Thr Gln Gln Val Asn
625                 630                 635

tctgattcac aggattatct ttaatcgcca aaacacactg gccagtgtac cataatatgt   1977

taccagaaga gttattatct atttgttctc cctttcagga aacttattgt aaagggactg   2037

ttttcatccc ataaagacag gactacagtt gtcagcttta tattacctgg atatggaagg   2097

aaactatttt tactctgcat gttctgtcct aagcgtcatc ttgagccttg cacatgatac   2157

tcagattcct ttcccttgct taggagtaaa acataatata ctttatgggg tgataatatc   2217

tccatagtta tttgaagtgg cttggaaaaa gcaagattga cttttgacat tggataaaat   2277

ctacaaatca gccctagagt ttcatggtca ttcacaaaac taaaatattt cccttgaaag   2337

gaagatggaa ggactggagt gtggtttggc agaacaactg catttcacag cttttcctat   2397

taaattggag cactgaatgt taaatgcata ccaaattatg catgggccct taatcacaca   2457

tacatggcta ccagctttga cacagcacta ttcatcctct ggccaaacga ctgtggttaa   2517

aaacacgtgt aaattgcttt ttaacagctg atactgtaaa agacaaagct aaaatgcaaa   2577

attaggcttt cattggcact tttcgaaaaa tatgcaacaa atttgggatg taatctggat   2637

ggccacttct gtacttaatg tgaagtattt agataccttt ttgaacactt aacagtttct   2697

tcgacaatga cttttgtaag gattggtagt atatatcatt ccttatgaca tacattgtct   2757

gttgctaatc cttggatctt gctgtattgt cacctaaatt ggtacaggta ctgatgaaaa   2817

tctctcatgg ataaacctaa cactcttcgt cacatgtttt tcctgcagcc tgaaggtttt   2877

taaaaggaaa agatatcaaa tgcctgctgc taccaccctt ttaaattgct atcttttgaa   2937

aagcaccagt atgtgttttt agattgattt ccctatttta gggaaatgac agtcagtagt   2997

ttcagttctg atggtataag caaagcaaat aaaacgtgtt tataaaagtt gtatcttgaa   3057
```

```
acactggtgt tcaacagcta gcagcttctg tggttcaccc cctgccttgt tagtgttacc   3117

catttatggt tatctccagc agcaatttct cta                                3150


<210> SEQ ID NO 18
<211> LENGTH: 638
<212> TYPE: PRT
<213> ORGANISM: Equus caballus

<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350
```

```
Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Gly Pro Pro Arg
    610                 615                 620

Pro Asn Arg Gly Met Pro Gln Met Asn Thr Gln Gln Val Asn
625                 630                 635


<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)
<223> OTHER INFORMATION:

<400> SEQUENCE: 19

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30
```

```
gct gcg ccg gct tct cag cat ccg gca acc ggc acc ggc gcc gtc cag      322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg      370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
```

```
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430

gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
```

-continued

```
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt cgt     2242
Lys Arg Gly Ser Gly Gln Ser Gly Pro Arg Gly Ala Pro Arg Gly Arg
        675                 680                 685

gga ggg ccc cca aga ccc aac aga ggg atg ccg caa atg aac act cag     2290
Gly Gly Pro Pro Arg Pro Asn Arg Gly Met Pro Gln Met Asn Thr Gln
    690                 695                 700

caa gtg aat taa tgtgatacac aggattatgt ttaatcgcca aaaacacact         2342
Gln Val Asn
705

ggccagtgta ccataatatg ttaccagaag agttattatc tatttgttct ccctttcagg   2402

aaacttattg taaagggact gttttcatcc cataaagaca ggactgcaat tgtcagcttt   2462

acattacctg gatatggaag gaaactattt ttattctgca tgttctgtcc taagcgtcat   2522

cttgagcctt gcacacaata caatactcag attcctcacc cttgcttagg agtaaaacat   2582

tatatactta tggggtgata atatctccat agttagttga agtggcttgg aaaaaaaatg   2642

caagattgaa tttttgacct tggataaaat ctacaatcag ccctagaact attcagtggt   2702

aattgacaaa gttaaagcat ttctttgaa aggaagatgg aaggagtgga gtgtggttta    2762

gcaaaactgc atttcatagc tttcccatta aattggagca ccgacagatt aaaagcatac   2822

caaattatgc atgggtcctt actcacacaa gtgaggctgg ctaccagcct tgacatagca   2882

ctcactagtc ttctggccaa acgactgtga ttaaaacaca tgtaaattgc tctttagtag   2942

tggatactgt gtaagacaaa gccaaattgc aaatcaggct ttgattggct cttctggaaa   3002

atatgcatca aatatggggg ataatctgga tgggctgctg ctgtgctcaa tgtgaactat   3062

ttagatacct ttggaacact taacagtttc tctgaacaat gacttacatg gggattggtc   3122

ctgtttgtca ttcctcacca taattgcatt gtcatcacta atccttggat cttgctgtat   3182

tgttactcaa attggtaata ggtactgatg gaaatcgcta atggatggat aatcataaca   3242

cttttggtca catgttttct cctgcagcct gaaagttctt aaagaaaaag atatcaaatg   3302

cctgctgcta ccaccctttt aaattgctat ctttagaaaa gcaccggtat gtgttttaga   3362

ttcatttccc tgttttaggg aaatgacagg cagtagtttc agttctgatg gcaaaacaaa   3422

taaaaacatg tttctaaaag ttgtatcttg aaacactggt gttcaacagc tagcagctaa   3482

agtaattcaa cccatgcatt gctagtgtca cagcctttgg ttatgtctag tagctgtttc   3542

tgaagtattt tcatttatct tttgtcaaat ttaaccctgt ttgaattctc tcctttcctc   3602

aaggagacac ttatgttcaa agtgttgatt ctttgcctta ggtgcataga gagtagacag   3662

tttggagatg gaaaggttag cagtgactta gccatatgtt ctgtgttgga atttgtgcta   3722

gcagtttgag cactagctct gcgtgcctat gaactgaatg ctgcttgtcc cattccattt   3782

tatgtcatgg agaaataatt ccacttggta acacaaaggc taagttaatg ttattttctg   3842

tacagaaatt aaattttact tttagccttt tgtaaacttt tttttttttt ttccaagccg   3902

gtatcagcta ctcaaaacaa ttctcagata ttcatcatta gacaactgga gtttttgctg   3962

gttttgtagc ctactaaaac tgctgaggct gttgaacatt ccacattcaa aagttttgta   4022

gggtggtgga taatggggaa gcttcaatgt ttattttaaa ataaataaaa taagttcttg   4082

acttttctca tgtgtggtta tggtacatca tattggaagg gttatctgtt tacttttgcc   4142

aagactattt tgccagcacc tacacttgtg tgctttaaaa gacaactacc tgggatgtac   4202

cacaaccata tgttaattgt attttattgg gatggataaa atgtttgtgg tttattggat   4262
```

-continued

```
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgccccccc   4802
ctcccccagg tagcatgcca ttgatgactt tttgcttagg gccattttat taccagggcc   4862
ttaatattcc taaaaagatg atttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
tgcttattct caggttcatt cactaaggtg cttggcagac aaccagtttc taagtgcaga   5102
atgtagttaa gcagcttcat atatgtgcca ggcaatttgt tttgttaaat tttcatctac   5162
ttaaggaaat agggtattgt agcttaggct gatcataccc ttcatttcaa ccttaagctc   5222
tcaacctgca tccatccgac ttgagctatt aagtacttta gttttatcga gtataagtta   5282
acagaaaaag taaattaagc tttgccttta ctattttgaa tttatataca ttctggaaaa   5342
acttagaaac tgttgtatat ttcattagat taaattatat gaaaatgtga ttgtttatag   5402
caaagcctgt gagttgcata caccctaagg aaaactcctt aagtgctcct tgaagagaga   5462
agaaacaatt ctgggtctgg tctttttaag aacaaagcta gactactgta tgttagcact   5522
gtacattaat agtctgttgt gaagcttgag cagtttcctg catagccttg atccttcacc   5582
gttggcattg aaaatagcag tatccctgat gtacttaaaa cttaaagtca ggttttggta   5642
tatttatttg taagtcttaa tttcctctaa atactatatc tctttagcga gacaacctga   5702
aatttattag cacatttggg tatctcttgc ttggcattat ggccagtgtt aactattcag   5762
tggtgaaaaa attacccctc aagacactgg agtgacccca gatgtgtgta gtaagtggca   5822
tggttcaact gtgtggttaa tgataaatat atgacttagt cggtatgatc tggaaagact   5882
tgattgaaag ataattcagc tgacataagg atgagtgagg agtggcaaac tggataaaag   5942
agtcaagaga cctgtattcc agtgactcct gttttgttta agcattagca agatctgtct   6002
ggggaaactg gatagggcag ttttcttcca tgtttagttt ttgtctcaac atttggaagc   6062
tattgaaggt tttaaaatgg tgtgtattgt ttttttttgg ggggggggtg gccagaatag   6122
tgggtcatct aataaaactg ccatttaaaa gatcaaaaaa aaaaaaaaaa aaaaaaaaa    6181
```

```
<210> SEQ ID NO 20
<211> LENGTH: 707
<212> TYPE: PRT
<213> ORGANISM: Mus musculus

<400> SEQUENCE: 20

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
```

```
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460
```

```
Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)
<223> OTHER INFORMATION:

<400> SEQUENCE: 21

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc      171
                    Met Pro Ser Ala Thr Ser His Ser Gly Ser Gly
                    1               5                   10

agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc      315
Thr Gly Ala Val Gln Thr Glu Ala Met Lys Gln Ile Leu Gly Val Ile
```

```
    45                  50                  55

gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa     1275
```

-continued

```
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct      1371
Thr Gln Asn Met Asp Met Pro Gln Leu Val Cys Pro Gln Val His Ser
            400                 405                 410

gaa tct aga ctt gcc caa tct aat caa gtt cct gta caa cca gaa gcc      1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct      1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa      1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag      1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc      1611
Thr Thr Ala Ser Ser Ser Leu Pro Ala Ala Ser Gln Pro Gln Val Phe
            480                 485                 490

cag gct ggg aca agt aaa cct ttg cac agc agt gga atc aat gta aat      1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca      1707
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
            560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
            640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680
```

```
gcc cca cga ggt cgt gga ggg ccc cca aga ccc aac aga ggg atg ccg     2235
Ala Pro Arg Gly Arg Gly Gly Pro Pro Arg Pro Asn Arg Gly Met Pro
    685                 690                 695

caa atg aac act cag caa gtg aat taa tgtgatacac aggattatgt          2282
Gln Met Asn Thr Gln Gln Val Asn
700                 705

ttaatcgcca aaaacacact ggccagtgta ccataatatg ttaccagaag agttattatc   2342

tatttgttct ccctttcagg aaacttattg taaagggact gttttcatcc cataaagaca   2402

ggactgcaat tgtcagcttt acattacctg gatatggaag gaaactattt ttattctgca   2462

tgttctgtcc taagcgtcat cttgagcctt gcacacaata caatactcag attcctcacc   2522

cttgcttagg agtaaaacat tatatactta tggggtgata atatctccat agttagttga   2582

agtggcttgg aaaaaaaatg caagattgaa tttttgacct tggataaaat ctacaatcag   2642

ccctagaact attcagtggt aattgacaaa gttaaagcat tttctttgaa aggaagatgg   2702

aaggagtgga gtgtggttta gcaaaactgc atttcatagc tttcccatta aattggagca   2762

ccgacagatt aaaagcatac caaattatgc atgggtcctt actcacacaa gtgaggctgg   2822

ctaccagcct tgacatagca ctcactagtc ttctggccaa acgactgtga ttaaaacaca   2882

tgtaaattgc tctttagtag tggatactgt gtaagacaaa gccaaattgc aaatcaggct   2942

ttgattggct cttctggaaa atatgcatca aatatggggg ataatctgga tgggctgctg   3002

ctgtgctcaa tgtgaactat ttagatacct ttggaacact taacagtttc tctgaacaat   3062

gacttacatg ggattggtc ctgtttgtca ttcctcacca taattgcatt gtcatcacta    3122

atccttggat cttgctgtat tgttactcaa attggtaata ggtactgatg gaaatcgcta   3182

atggatggat aatcataaca cttttggtca catgttttct cctgcagcct gaaagttctt   3242

aaagaaaaag atatcaaatg cctgctgcta ccaccctttt aaattgctat ctttagaaaa   3302

gcaccggtat gtgttttaga ttcatttccc tgttttaggg aaatgacagg cagtagtttc   3362

agttctgatg gcaaaacaaa taaaaacatg tttctaaaag ttgtatcttg aaacactggt   3422

gttcaacagc tagcagctaa agtaattcaa cccatgcatt gctagtgtca cagcctttgg   3482

ttatgtctag tagctgtttc tgaagtattt tcatttatct tttgtcaaat ttaaccctgt   3542

ttgaattctc tcctttcctc aaggagacac ttatgttcaa agtgttgatt ctttgcctta   3602

ggtgcataga gagtagacag tttggagatg gaaaggttag cagtgactta gccatatgtt   3662

ctgtgttgga atttgtgcta gcagtttgag cactagctct gcgtgcctat gaactgaatg   3722

ctgcttgtcc cattccattt tatgtcatgg agaaataatt ccacttggta acacaaaggc   3782

taagttaatg ttattttctg tacagaaatt aaattttact tttagccttt tgtaaacttt   3842

tttttttttt ttccaagccg gtatcagcta ctcaaaacaa ttctcagata ttcatcatta   3902

gacaactgga gtttttgctg gttttgtagc ctactaaaac tgctgaggct gttgaacatt   3962

ccacattcaa aagttttgta gggtggtgga taatggggaa gcttcaatgt ttattttaaa   4022

ataaataaaa taagttcttg acttttctca tgtgtggtta tggtacatca tattggaagg   4082

gttatctgtt tacttttgcc aagactattt tgccagcacc tacacttgtg tgctttaaaa   4142

gacaactacc tgggatgtac cacaaccata tgttaattgt attttattgg gatggataaa   4202

atgtttgtgg tttattggat aatccctaga tggtgtgtta cgtgtgtaga atataatttt   4262

atgatagtaa gaaagcaaaa ttgaagaaaa taagtttagt attgaatttg agttctgaag   4322

tgaattcagg gaatgtctca cgtttcgggc ttctacccaa agtgtagggc agaaggtgta   4382

aaagttgttt gtagtttgac ttgtttattt tttaagttgc ttattccttt caacagcaac   4442
```

```
atatcattag ctgtcattct accattgcag ttctagtgag ttttaacgtc tgcattcaag   4502

actgttttaa aagcaacctc actggacaga gaactgctaa agtcttttcc ttaagatctg   4562

agtctttgtt actcagtatc ttctataata tgcaaatgct tgtctagagg cagaagacct   4622

tttgtttggt caagtgtgta ttttaccaga gtacagggaa ctgatggtcc tacatgtctc   4682

ttagtgtagt aagactataa aatcttttgt acatgcacaa ttcacagtat gtttagatac   4742

cacgtgtata atgccccccc ctcccccagg tagcatgcca ttgatgactt tttgcttagg   4802

gccattttat taccagggcc ttaatattcc taaaaagatg atttttttc atcctttctc   4862

ctcttttgat cattgtatct tgatattaaa aacatgacct tccaatgatt gtagtaaatt   4922

aacttctata gttcttttgt ctctatatgt attcatatat atgctattgt atagagactt   4982

caaggagaca tggagatgca tgcttattct caggttcatt cactaaggtg cttggcagac   5042

aaccagtttc taagtgcaga atgtagttaa gcagcttcat atatgtgcca ggcaatttgt   5102

tttgttaaat tttcatctac ttaaggaaat agggtattgt agcttaggct gatcataccc   5162

ttcatttcaa ccttaagctc tcaacctgca tccatccgac ttgagctatt aagtacttta   5222

gttttatcga gtataagtta acagaaaaag taaattaagc tttgccttta ctattttgaa   5282

tttatataca ttctggaaaa acttagaaac tgttgtatat ttcattagat taaattatat   5342

gaaaatgtga ttgtttatag caaagcctgt gagttgcata caccctaagg aaaactcctt   5402

aagtgctcct tgaagagaga agaaacaatt ctgggtctgg tctttttaag aacaaagcta   5462

gactactgta tgttagcact gtacattaat agtctgttgt gaagcttgag cagtttcctg   5522

catagccttg atccttcacc gttggcattg aaaatagcag tatccctgat gtacttaaaa   5582

cttaaagtca ggttttggta tatttatttg taagtcttaa tttcctctaa atactatatc   5642

tctttagcga gacaacctga aatttattag cacatttggg tatctcttgc ttggcattat   5702

ggccagtgtt aactattcag tggtgaaaaa attacccctc aagacactgg agtgacccca   5762

gatgtgtgta gtaagtggca tggttcaact gtgtggttaa tgataaatat atgacttagt   5822

cggtatgatc tggaaagact tgattgaaag ataattcagc tgacataagg atgagtgagg   5882

agtggcaaac tggataaaag agtcaagaga cctgtattcc agtgactcct gttttgttta   5942

agcattagca agatctgtct ggggaaactg gatagggcag ttttcttcca tgtttagttt   6002

ttgtctcaac atttggaagc tattgaaggt tttaaaatgg tgtgtattgt tttttttgg   6062

ggggggggtg gccagaatag tgggtcatct aataaaactg ccatttaaaa gatcaaaaaa   6122

aaaaaaaaaa aaaaaaaaa                                                 6141
```

<210> SEQ ID NO 22
<211> LENGTH: 707
<212> TYPE: PRT
<213> ORGANISM: Mus musculus

<400> SEQUENCE: 22

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60
```

```
Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
```

```
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705


<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)
<223> OTHER INFORMATION:

<400> SEQUENCE: 23

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75
```

```
tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc      699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag acg ctt gat cct gcc att gta     1275
Met Gln Gly Pro Tyr Asn Phe Ile Gln Thr Leu Asp Pro Ala Ile Val
    365                 370                 375

tcc gca cag cct atg aac cct acc cag aac atg gat atg cct cag ctg     1323
Ser Ala Gln Pro Met Asn Pro Thr Gln Asn Met Asp Met Pro Gln Leu
```

```
380                 385                 390                 395

gtt tgc cct cag gtt cat tct gaa tct aga ctt gcc caa tct aat caa      1371
Val Cys Pro Gln Val His Ser Glu Ser Arg Leu Ala Gln Ser Asn Gln
                400                 405                 410

gtt cct gta caa cca gaa gcc aca cag gtt cct ttg gtt tca tcc aca      1419
Val Pro Val Gln Pro Glu Ala Thr Gln Val Pro Leu Val Ser Ser Thr
            415                 420                 425

agt gag ggg tat aca gca tct cag ccc ttg tac cag cca tct cat gct      1467
Ser Glu Gly Tyr Thr Ala Ser Gln Pro Leu Tyr Gln Pro Ser His Ala
        430                 435                 440

acg gag cag cgg ccg cag aaa gag cca atg gat cag att cag gca aca      1515
Thr Glu Gln Arg Pro Gln Lys Glu Pro Met Asp Gln Ile Gln Ala Thr
    445                 450                 455

ata tct ttg aat aca gac cag act aca gca tcc tca tcc ctt cct gct      1563
Ile Ser Leu Asn Thr Asp Gln Thr Thr Ala Ser Ser Ser Leu Pro Ala
460                 465                 470                 475

gct tct cag cct caa gtg ttc cag gct ggg aca agt aaa cct ttg cac      1611
Ala Ser Gln Pro Gln Val Phe Gln Ala Gly Thr Ser Lys Pro Leu His
                480                 485                 490

agc agt gga atc aat gta aat gca gct cca ttc cag tcc atg caa acg      1659
Ser Ser Gly Ile Asn Val Asn Ala Ala Pro Phe Gln Ser Met Gln Thr
            495                 500                 505

gtg ttc aat atg aat gct cca gtc cct cct gct aat gaa cca gaa acg      1707
Val Phe Asn Met Asn Ala Pro Val Pro Pro Ala Asn Glu Pro Glu Thr
        510                 515                 520

tta aaa caa cag agt cag tac cag gcc act tat aac cag agt ttt tcc      1755
Leu Lys Gln Gln Ser Gln Tyr Gln Ala Thr Tyr Asn Gln Ser Phe Ser
    525                 530                 535

agt cag cct cac caa gtg gaa caa aca gag ctt caa caa gac caa ctg      1803
Ser Gln Pro His Gln Val Glu Gln Thr Glu Leu Gln Gln Asp Gln Leu
540                 545                 550                 555

caa acg gtg gtt ggc act tac cat gga tcc cag gac cag cct cat caa      1851
Gln Thr Val Val Gly Thr Tyr His Gly Ser Gln Asp Gln Pro His Gln
                560                 565                 570

gtg cct ggt aac cac cag caa ccc cca cag cag aac act ggc ttt cca      1899
Val Pro Gly Asn His Gln Gln Pro Pro Gln Gln Asn Thr Gly Phe Pro
            575                 580                 585

cgt agc agt cag cct tat tac aac agt cgt ggg gta tct cga gga ggg      1947
Arg Ser Ser Gln Pro Tyr Tyr Asn Ser Arg Gly Val Ser Arg Gly Gly
        590                 595                 600

tct cgt ggt gcc aga ggc ttg atg aat gga tac agg ggc cct gcc aat      1995
Ser Arg Gly Ala Arg Gly Leu Met Asn Gly Tyr Arg Gly Pro Ala Asn
    605                 610                 615

gga ttt aga gga gga tat gat ggt tac cgc cct tca ttc tcg aac act      2043
Gly Phe Arg Gly Gly Tyr Asp Gly Tyr Arg Pro Ser Phe Ser Asn Thr
620                 625                 630                 635

cca aac agt ggt tat tca cag tct cag ttc act gct ccc cgg gac tac      2091
Pro Asn Ser Gly Tyr Ser Gln Ser Gln Phe Thr Ala Pro Arg Asp Tyr
                640                 645                 650

tct ggt tac cag cgg gat gga tat cag cag aat ttc aag cga ggc tct      2139
Ser Gly Tyr Gln Arg Asp Gly Tyr Gln Gln Asn Phe Lys Arg Gly Ser
            655                 660                 665

ggg cag agt gga cca cgg gga gcc cca cga ggt cgt gga ggg ccc cca      2187
Gly Gln Ser Gly Pro Arg Gly Ala Pro Arg Gly Arg Gly Gly Pro Pro
        670                 675                 680

aga ccc aac aga ggg atg ccg caa atg aac act cag caa gtg aat taa      2235
Arg Pro Asn Arg Gly Met Pro Gln Met Asn Thr Gln Gln Val Asn
    685                 690                 695

tgtgatacac aggattatgt ttaatcgcca aaaacacact ggccagtgta ccataatatg   2295
```

```
ttaccagaag agttattatc tatttgttct ccctttcagg aaacttattg taaagggact   2355
gttttcatcc cataaagaca ggactgcaat tgtcagcttt acattacctg gatatggaag   2415
gaaactattt ttattctgca tgttctgtcc taagcgtcat cttgagcctt gcacacaata   2475
caatactcag attcctcacc cttgcttagg agtaaaacat tatatactta tggggtgata   2535
atatctccat agttagttga agtggcttgg aaaaaaaatg caagattgaa tttttgacct   2595
tggataaaat ctacaatcag ccctagaact attcagtggt aattgacaaa gttaaagcat   2655
tttctttgaa aggaagatgg aaggagtgga gtgtggttta gcaaaactgc atttcatagc   2715
tttcccatta aattggagca ccgacagatt aaaagcatac caaattatgc atgggtcctt   2775
actcacacaa gtgaggctgg ctaccagcct tgacatagca ctcactagtc ttctggccaa   2835
acgactgtga ttaaaacaca tgtaaattgc tctttagtag tggatactgt gtaagacaaa   2895
gccaaattgc aaatcaggct ttgattggct cttctggaaa atatgcatca aatatggggg   2955
ataatctgga tgggctgctg ctgtgctcaa tgtgaactat ttagatacct ttggaacact   3015
taacagtttc tctgaacaat gacttacatg ggattggtc ctgtttgtca ttcctcacca   3075
taattgcatt gtcatcacta atccttggat cttgctgtat tgttactcaa attggtaata   3135
ggtactgatg gaaatcgcta atggatggat aatcataaca cttttggtca catgttttct   3195
cctgcagcct gaaagttctt aaagaaaaag atatcaaatg cctgctgcta ccaccctttt   3255
aaattgctat ctttagaaaa gcaccggtat gtgttttaga ttcatttccc tgttttaggg   3315
aaatgacagg cagtagtttc agttctgatg gcaaaacaaa taaaaacatg tttctaaaag   3375
ttgtatcttg aaacactggt gttcaacagc tagcagctaa agtaattcaa cccatgcatt   3435
gctagtgtca cagcctttgg ttatgtctag tagctgtttc tgaagtattt tcatttatct   3495
tttgtcaaat ttaaccctgt ttgaattctc tcctttcctc aaggagacac ttatgttcaa   3555
agtgttgatt ctttgcctta ggtgcataga gagtagacag tttggagatg gaaaggttag   3615
cagtgactta gccatatgtt ctgtgttgga atttgtgcta gcagtttgag cactagctct   3675
gcgtgcctat gaactgaatg ctgcttgtcc cattccattt tatgtcatgg agaaataatt   3735
ccacttggta acacaaaggc taagttaatg ttattttctg tacagaaatt aaattttact   3795
tttagccttt tgtaaacttt tttttttttt ttccaagccg gtatcagcta ctcaaaacaa   3855
ttctcagata ttcatcatta gacaactgga gtttttgctg gttttgtagc ctactaaaac   3915
tgctgaggct gttgaacatt ccacattcaa aagttttgta gggtggtgga taatggggaa   3975
gcttcaatgt ttattttaaa ataaataaaa taagttcttg acttttctca tgtgtggtta   4035
tggtacatca tattggaagg gttatctgtt tacttttgcc aagactattt tgccagcacc   4095
tacacttgtg tgctttaaaa gacaactacc tgggatgtac cacaaccata tgttaattgt   4155
attttattgg gatggataaa atgtttgtgg tttattggat aatccctaga tggtgtgtta   4215
cgtgtgtaga atataatttt atgatagtaa gaaagcaaaa ttgaagaaaa taagtttagt   4275
attgaatttg agttctgaag tgaattcagg gaatgtctca cgtttcgggc ttctacccaa   4335
agtgtagggc agaaggtgta aaagttgttt gtagtttgac ttgtttattt tttaagttgc   4395
ttattccttt caacagcaac atatcattag ctgtcattct accattgcag ttctagtgag   4455
ttttaacgtc tgcattcaag actgttttaa aagcaacctc actggacaga gaactgctaa   4515
agtcttttcc ttaagatctg agtctttgtt actcagtatc ttctataata tgcaaatgct   4575
tgtctagagg cagaagacct tttgtttggt caagtgtgta ttttaccaga gtacagggaa   4635
```

```
ctgatggtcc tacatgtctc ttagtgtagt aagactataa aatcttttgt acatgcacaa   4695

ttcacagtat gtttagatac cacgtgtata atgccccccc ctcccccagg tagcatgcca   4755

ttgatgactt tttgcttagg gccattttat taccagggcc ttaatattcc taaaaagatg   4815

atttttttc atcctttctc ctcttttgat cattgtatct tgatattaaa aacatgacct   4875

tccaatgatt gtagtaaatt aacttctata gttcttttgt ctctatatgt attcatatat   4935

atgctattgt atagagactt caaggagaca tggagatgca tgcttattct caggttcatt   4995

cactaaggtg cttggcagac aaccagtttc taagtgcaga atgtagttaa gcagcttcat   5055

atatgtgcca ggcaatttgt tttgttaaat tttcatctac ttaaggaaat agggtattgt   5115

agcttaggct gatcataccc ttcatttcaa ccttaagctc tcaacctgca tccatccgac   5175

ttgagctatt aagtacttta gttttatcga gtataagtta acagaaaaag taaattaagc   5235

tttgccttta ctattttgaa tttatataca ttctggaaaa acttagaaac tgttgtatat   5295

ttcattagat taaattatat gaaaatgtga ttgtttatag caaagcctgt gagttgcata   5355

caccctaagg aaaactcctt aagtgctcct tgaagagaga agaaacaatt ctgggtctgg   5415

tctttttaag aacaaagcta gactactgta tgttagcact gtacattaat agtctgttgt   5475

gaagcttgag cagtttcctg catagccttg atccttcacc gttggcattg aaaatagcag   5535

tatccctgat gtacttaaaa cttaaagtca ggttttggta tatttatttg taagtcttaa   5595

tttcctctaa atactatatc tctttagcga gacaacctga aatttattag cacatttggg   5655

tatctcttgc ttggcattat ggccagtgtt aactattcag tggtgaaaaa attacccctc   5715

aagacactgg agtgacccca gatgtgtgta gtaagtggca tggttcaact gtgtggttaa   5775

tgataaatat atgacttagt cggtatgatc tggaaagact tgattgaaag ataattcagc   5835

tgacataagg atgagtgagg agtggcaaac tggataaaag agtcaagaga cctgtattcc   5895

agtgactcct gttttgttta agcattagca agatctgtct ggggaaactg gatagggcag   5955

ttttcttcca tgtttagttt ttgtctcaac atttggaagc tattgaaggt tttaaaatgg   6015

tgtgtattgt tttttttgg gggggggtg gccagaatag tgggtcatct aataaaactg   6075

ccatttaaaa gatcaaaaaa aaaaaaaaaa aaaaaaaaa                          6114
```

```
<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110
```

```
Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
    370                 375                 380

Asn Pro Thr Gln Asn Met Asp Met Pro Gln Leu Val Cys Pro Gln Val
385                 390                 395                 400

His Ser Glu Ser Arg Leu Ala Gln Ser Asn Gln Val Pro Val Gln Pro
                405                 410                 415

Glu Ala Thr Gln Val Pro Leu Val Ser Ser Thr Ser Glu Gly Tyr Thr
            420                 425                 430

Ala Ser Gln Pro Leu Tyr Gln Pro Ser His Ala Thr Glu Gln Arg Pro
        435                 440                 445

Gln Lys Glu Pro Met Asp Gln Ile Gln Ala Thr Ile Ser Leu Asn Thr
    450                 455                 460

Asp Gln Thr Thr Ala Ser Ser Ser Leu Pro Ala Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
            500                 505                 510

Ala Pro Val Pro Pro Ala Asn Glu Pro Glu Thr Leu Lys Gln Gln Ser
        515                 520                 525

Gln Tyr Gln Ala Thr Tyr Asn Gln Ser Phe Ser Ser Gln Pro His Gln
```

```
    530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Gly Ser Arg Gly Ala Arg
        595                 600                 605

Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
            660                 665                 670

Arg Gly Ala Pro Arg Gly Arg Gly Gly Pro Pro Arg Pro Asn Arg Gly
        675                 680                 685

Met Pro Gln Met Asn Thr Gln Gln Val Asn
    690                 695


<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)
<223> OTHER INFORMATION:

<400> SEQUENCE: 25

gctggctggc taagtccctc ccgcgccggc tcttgtccca ctaggagcag ctcagagccg      60

cggggacagg gcgaagcggc ctgcgcccac ggagcgcacg tctctgttct caacgcagca     120

ccacccttgc ccccctcggc tgcccactcc agacgtccag cggctccgcg cgcgcacg       178

atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5                   10                  15

ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30

gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35                  40                  45

acc gag gcc atg aag cag att ctc ggc gta atc gac aag aaa ctt cgg       370
Thr Glu Ala Met Lys Gln Ile Leu Gly Val Ile Asp Lys Lys Leu Arg
    50                  55                  60

aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65                  70                  75                  80

aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                85                  90                  95

tac cag gaa gtc aca aat aat ttg gag ttt gca aag gaa tta cag agg       514
Tyr Gln Glu Val Thr Asn Asn Leu Glu Phe Ala Lys Glu Leu Gln Arg
            100                 105                 110

agt ttc atg gca tta agt caa gat att cag aaa aca ata aag aag aca       562
```

```
Ser Phe Met Ala Leu Ser Gln Asp Ile Gln Lys Thr Ile Lys Lys Thr
        115                 120                 125

gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140

aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160

gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175

tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190

cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205

tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220

gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240

tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255

gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270

gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285

tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300

agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320

gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335

cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350

aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365

aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380

cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400

atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415

caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430
```

-continued

```
gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445

cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460

att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480

tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495

aaa cct ttg cac agc agt gga atc aat gta aat gca gct cca ttc cag     1714
Lys Pro Leu His Ser Ser Gly Ile Asn Val Asn Ala Ala Pro Phe Gln
            500                 505                 510

tcc atg caa acg gtg ttc aat atg aat gct cca gtc cct cct gct aat     1762
Ser Met Gln Thr Val Phe Asn Met Asn Ala Pro Val Pro Pro Ala Asn
        515                 520                 525

gaa cca gaa acg tta aaa caa cag agt cag tac cag gcc act tat aac     1810
Glu Pro Glu Thr Leu Lys Gln Gln Ser Gln Tyr Gln Ala Thr Tyr Asn
    530                 535                 540

cag agt ttt tcc agt cag cct cac caa gtg gaa caa aca gag ctt caa     1858
Gln Ser Phe Ser Ser Gln Pro His Gln Val Glu Gln Thr Glu Leu Gln
545                 550                 555                 560

caa gac caa ctg caa acg gtg gtt ggc act tac cat gga tcc cag gac     1906
Gln Asp Gln Leu Gln Thr Val Val Gly Thr Tyr His Gly Ser Gln Asp
                565                 570                 575

cag cct cat caa gtg cct ggt aac cac cag caa ccc cca cag cag aac     1954
Gln Pro His Gln Val Pro Gly Asn His Gln Gln Pro Pro Gln Gln Asn
            580                 585                 590

act ggc ttt cca cgt agc agt cag cct tat tac aac agt cgt ggg gta     2002
Thr Gly Phe Pro Arg Ser Ser Gln Pro Tyr Tyr Asn Ser Arg Gly Val
        595                 600                 605

tct cga gga ggg tct cgt ggt gcc aga ggc ttg atg aat gga tac agg     2050
Ser Arg Gly Gly Ser Arg Gly Ala Arg Gly Leu Met Asn Gly Tyr Arg
    610                 615                 620

ggc cct gcc aat gga ttt aga gga gga tat gat ggt tac cgc cct tca     2098
Gly Pro Ala Asn Gly Phe Arg Gly Gly Tyr Asp Gly Tyr Arg Pro Ser
625                 630                 635                 640

ttc tcg aac act cca aac agt ggt tat tca cag tct cag ttc act gct     2146
Phe Ser Asn Thr Pro Asn Ser Gly Tyr Ser Gln Ser Gln Phe Thr Ala
                645                 650                 655

ccc cgg gac tac tct ggt tac cag cgg gat gga tat cag cag aat ttc     2194
Pro Arg Asp Tyr Ser Gly Tyr Gln Arg Asp Gly Tyr Gln Gln Asn Phe
            660                 665                 670

aag cga ggc tct ggg cag agt gga cca cgg gga gcc cca cga ggt aat     2242
Lys Arg Gly Ser Gly Gln Ser Gly Pro Arg Gly Ala Pro Arg Gly Asn
        675                 680                 685

ata ttg tgg tgg tga tcctagctcc tatgtggagc ttctgttctg gccttggaag     2297
Ile Leu Trp Trp
    690

aactgttcat agtccgcatg taggttacat gttaggaata catttatctt ttccagactt   2357

gttgctaaag attaaatgaa atgctctgtt tctaaaattt catcttgaat ccaaatttta   2417

atttttgaat gactttccct gctgttgtct tcaaaatcag aacattttct ctgcctcaga   2477

aaagcgtttt tccaactgga aatttatttt tcaggtctta aaacctgcta aatgttttta   2537

ggaagtacct actgaaactt tttgtaagac atttttggaa cgagcttgaa catttatata   2597

aatttattac cctctttgat tttgaaaca tgcatattat atttaggctg agaagccctt    2657
```

```
caaatggcca gataagccac agttttagct agagaaccat ttagaattga cataactaat   2717

ctaaacttga acacttttag gaccaatgtt agtgttctaa ataccaacat atttctgatg   2777

tttaaacaga tctcccaaat tcttaggacc ttgatgtcat taaaatttag aatgacaagc   2837

ttaagaggct ttagtttcat ttgtttttca agtaatgaaa aataatttct tacatgggca   2897

gatagttaat ttgttgaaca attacaggta gcatttcatg taatctgatg ttctaaatgg   2957

ttctcttatt gaaggaggtt aaagaattag gtttcttaca gtttttggct ggccatgaca   3017

tgtataaaat gtatattaag gaggaattat aaagtacttt aatttgaatg ctagtggcaa   3077

ttgatcatta agaaagtact ttaaagcaaa aggttaatgg gtcatctggg aaaaatactg   3137

aagtatcaaa ggtatttgca tgtgaatgtg ggttatgttc ttctatccca ccttgtagca   3197

tattctatga aagttgagtt aaatgatagc taaaatatct gtttcaacag catgtaaaaa   3257

gttattttaa ctgttacaag tcattataca attttgaatg ttctgtagtt tctttttaac   3317

agtttaggta caaaggtctg ttttcattct ggtgcttttt attaattttg atagtatgat   3377

gtcacttcct attgaaatgt aagctagcgt gtaccttaga atgtgagctc catgagagca   3437

ggtaccttgt ttgtcttcac tgctgtatct attcccaacg cctcatgaca gtgcctggca   3497

catagtaggc actcaataaa tacttgttga atgaatgaaa aaaaaaaaaa a            3548
```

```
<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
```

```
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640
```

```
Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)
<223> OTHER INFORMATION:

<400> SEQUENCE: 27

cccaccgcgc gcgcgcgtag ccgcctgccc gcccgcccgc tgcgcgtttt gtcccgcgtc      60

tctccccgtc cgtctcctga cttgctggtc ttgtccttcc ctcccgcttt tttcctctcc     120

tctcttctcg gtctaaag atg ccc tcg gcc acc agc cac agc gga agc ggc       171
                    Met Pro Ser Ala Thr Ser His Ser Gly Ser Gly
                    1               5                   10

agc aaa tcg tcg gga ccg ccg ccg ccg tcc ggt tcc tcc ggg agt gag       219
Ser Lys Ser Ser Gly Pro Pro Pro Pro Ser Gly Ser Ser Gly Ser Glu
            15                  20                  25

gcg gcg gcc ggg gca gct gcg ccg gct tct cag cat ccg gca acc ggc       267
Ala Ala Ala Gly Ala Ala Ala Pro Ala Ser Gln His Pro Ala Thr Gly
        30                  35                  40

acc ggc gcc gtc cag acc gag gcc atg aag cag att ctc ggc gta atc       315
Thr Gly Ala Val Gln Thr Glu Ala Met Lys Gln Ile Leu Gly Val Ile
    45                  50                  55

gac aag aaa ctt cgg aac ctg gag aag aaa aag ggt aaa ctt gat gat       363
Asp Lys Lys Leu Arg Asn Leu Glu Lys Lys Lys Gly Lys Leu Asp Asp
60                  65                  70                  75

tac cag gaa cga atg aat aaa ggg gaa agg ctc aat caa gac cag ctg       411
Tyr Gln Glu Arg Met Asn Lys Gly Glu Arg Leu Asn Gln Asp Gln Leu
                80                  85                  90

gat gcc gta tct aag tac cag gaa gtc aca aat aat ttg gag ttt gca       459
Asp Ala Val Ser Lys Tyr Gln Glu Val Thr Asn Asn Leu Glu Phe Ala
            95                  100                 105

aag gaa tta cag agg agt ttc atg gca tta agt caa gat att cag aaa       507
Lys Glu Leu Gln Arg Ser Phe Met Ala Leu Ser Gln Asp Ile Gln Lys
        110                 115                 120

aca ata aag aag aca gca cgt cgg gaa cag ctt atg aga gaa gaa gca       555
Thr Ile Lys Lys Thr Ala Arg Arg Glu Gln Leu Met Arg Glu Glu Ala
    125                 130                 135

gaa cag aag cgc tta aaa act gta ctt gag tta cag tat gta ttg gat       603
Glu Gln Lys Arg Leu Lys Thr Val Leu Glu Leu Gln Tyr Val Leu Asp
140                 145                 150                 155

aag ctg gga gat gat gat gtg aga aca gat ctg aaa caa ggt ttg agt       651
Lys Leu Gly Asp Asp Asp Val Arg Thr Asp Leu Lys Gln Gly Leu Ser
                160                 165                 170

gga gtg cca ata ttg tct gag gag gag ttg tca ttg ctg gat gag ttc       699
Gly Val Pro Ile Leu Ser Glu Glu Glu Leu Ser Leu Leu Asp Glu Phe
            175                 180                 185

tac aag ctc gta gat cct gag cgt gac atg agt tta agg tta aat gag       747
Tyr Lys Leu Val Asp Pro Glu Arg Asp Met Ser Leu Arg Leu Asn Glu
```

```
        190                 195                 200

cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215

gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235

gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250

aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
            255                 260                 265

gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280

caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295

gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315

gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330

gcg tcc cct tca gtc cca gag ccc cac tct ttg act cca gtg gct cag     1179
Ala Ser Pro Ser Val Pro Glu Pro His Ser Leu Thr Pro Val Ala Gln
            335                 340                 345

tca gat cca ctt gtg aga agg cag cgt gta caa gat ctt atg gca caa     1227
Ser Asp Pro Leu Val Arg Arg Gln Arg Val Gln Asp Leu Met Ala Gln
        350                 355                 360

atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
    365                 370                 375

aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395

acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410

gaa tct aga ctt gcc caa tct aat caa gtt cct gta caa cca gaa gcc     1419
Glu Ser Arg Leu Ala Gln Ser Asn Gln Val Pro Val Gln Pro Glu Ala
            415                 420                 425

aca cag gtt cct ttg gtt tca tcc aca agt gag ggg tat aca gca tct     1467
Thr Gln Val Pro Leu Val Ser Ser Thr Ser Glu Gly Tyr Thr Ala Ser
        430                 435                 440

cag ccc ttg tac cag cca tct cat gct acg gag cag cgg ccg cag aaa     1515
Gln Pro Leu Tyr Gln Pro Ser His Ala Thr Glu Gln Arg Pro Gln Lys
    445                 450                 455

gag cca atg gat cag att cag gca aca ata tct ttg aat aca gac cag     1563
Glu Pro Met Asp Gln Ile Gln Ala Thr Ile Ser Leu Asn Thr Asp Gln
460                 465                 470                 475

act aca gca tcc tca tcc ctt cct gct gct tct cag cct caa gtg ttc     1611
Thr Thr Ala Ser Ser Ser Leu Pro Ala Ala Ser Gln Pro Gln Val Phe
                480                 485                 490

cag gct ggg aca agt aaa cct ttg cac agc agt gga atc aat gta aat     1659
Gln Ala Gly Thr Ser Lys Pro Leu His Ser Ser Gly Ile Asn Val Asn
            495                 500                 505

gca gct cca ttc cag tcc atg caa acg gtg ttc aat atg aat gct cca     1707
```

```
Ala Ala Pro Phe Gln Ser Met Gln Thr Val Phe Asn Met Asn Ala Pro
        510                 515                 520

gtc cct cct gct aat gaa cca gaa acg tta aaa caa cag agt cag tac      1755
Val Pro Pro Ala Asn Glu Pro Glu Thr Leu Lys Gln Gln Ser Gln Tyr
    525                 530                 535

cag gcc act tat aac cag agt ttt tcc agt cag cct cac caa gtg gaa      1803
Gln Ala Thr Tyr Asn Gln Ser Phe Ser Ser Gln Pro His Gln Val Glu
540                 545                 550                 555

caa aca gag ctt caa caa gac caa ctg caa acg gtg gtt ggc act tac      1851
Gln Thr Glu Leu Gln Gln Asp Gln Leu Gln Thr Val Val Gly Thr Tyr
                560                 565                 570

cat gga tcc cag gac cag cct cat caa gtg cct ggt aac cac cag caa      1899
His Gly Ser Gln Asp Gln Pro His Gln Val Pro Gly Asn His Gln Gln
            575                 580                 585

ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
        590                 595                 600

aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
    605                 610                 615

atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620                 625                 630                 635

ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
                640                 645                 650

tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655                 660                 665

tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
        670                 675                 680

gcc cca cga ggt aat ata ttg tgg tgg tga tcctagctcc tatgtggagc       2237
Ala Pro Arg Gly Asn Ile Leu Trp Trp
    685                 690

ttctgttctg gccttggaag aactgttcat agtccgcatg taggttacat gttaggaata    2297

catttatctt ttccagactt gttgctaaag attaaatgaa atgctctgtt tctaaaattt    2357

catcttgaat ccaaatttta atttttgaat gactttccct gctgttgtct tcaaaatcag    2417

aacattttct ctgcctcaga aaagcgtttt tccaactgga aatttatttt tcaggtctta    2477

aaacctgcta aatgttttta ggaagtacct actgaaactt tttgtaagac atttttggaa    2537

cgagcttgaa catttatata aatttattac cctctttgat ttttgaaaca tgcatattat    2597

atttaggctg agaagccctt caaatggcca gataagccac agttttagct agagaaccat    2657

ttagaattga cataactaat ctaaacttga acactttttag gaccaatgtt agtgttctaa   2717

ataccaacat atttctgatg tttaaacaga tctcccaaat tcttaggacc ttgatgtcat    2777

taaaatttag aatgacaagc ttaagaggct ttagtttcat ttgtttttca agtaatgaaa    2837

aataatttct tacatgggca gatagttaat ttgttgaaca attacaggta gcatttcatg    2897

taatctgatg ttctaaatgg ttctcttatt gaaggaggtt aaagaattag gtttcttaca    2957

gtttttggct ggccatgaca tgtataaaat gtatattaag gaggaattat aaagtacttt    3017

aatttgaatg ctagtggcaa ttgatcatta agaaagtact ttaaagcaaa aggttaatgg    3077

gtcatctggg aaaaatactg aagtatcaaa ggtatttgca tgtgaatgtg ggttatgttc    3137

ttctatccca ccttgtagca tattctatga aagttgagtt aaatgatagc taaaatatct    3197
```

```
gtttcaacag catgtaaaaa gttattttaa ctgttacaag tcattataca attttgaatg   3257

ttctgtagtt tctttttaac agtttaggta caaaggtctg ttttcattct ggtgcttttt   3317

attaattttg atagtatgat gtcacttcct attgaaatgt aagctagcgt gtaccttaga   3377

atgtgagctc catgagagca ggtaccttgt ttgtcttcac tgctgtatct attcccaacg   3437

cctcatgaca gtgcctggca catagtaggc actcaataaa tacttgttga atgaatgaaa   3497

aaaaaaaaaa a                                                        3508


<210> SEQ ID NO 28
<211> LENGTH: 692
<212> TYPE: PRT
<213> ORGANISM: Mus musculus

<400> SEQUENCE: 28

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320
```

```
Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
    690


<210> SEQ ID NO 29
<211> LENGTH: 2109
<212> TYPE: DNA
<213> ORGANISM: Gallus gallus
<220> FEATURE:
```

```
<221> NAME/KEY: CDS
<222> LOCATION: (1)..(2109)
<223> OTHER INFORMATION:

<400> SEQUENCE: 29

atg ccc tcg gct acc aac ggc acc atg gcg agc agc agc ggg aag gcg       48
Met Pro Ser Ala Thr Asn Gly Thr Met Ala Ser Ser Ser Gly Lys Ala
1               5                   10                  15

ggc ccg ggc ggc aac gag cag gcc ccg gcg gcg gca gcg gcg gcc ccg       96
Gly Pro Gly Gly Asn Glu Gln Ala Pro Ala Ala Ala Ala Ala Ala Pro
            20                  25                  30

cag gcg tcg ggc ggc agc atc acc tcg gtt cag acc gag gcc atg aag      144
Gln Ala Ser Gly Gly Ser Ile Thr Ser Val Gln Thr Glu Ala Met Lys
        35                  40                  45

cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50                  55                  60

aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65                  70                  75                  80

cta aat caa gat caa ctg gat gca gtg tca aaa tac cag gaa gtg aca      288
Leu Asn Gln Asp Gln Leu Asp Ala Val Ser Lys Tyr Gln Glu Val Thr
                85                  90                  95

aat aac ctg gaa ttc gct aaa gaa ctg cag agg agc ttt atg gca ctg      336
Asn Asn Leu Glu Phe Ala Lys Glu Leu Gln Arg Ser Phe Met Ala Leu
            100                 105                 110

agc caa gat atc cag aaa aca ata aaa aag acg gct cgc agg gag cag      384
Ser Gln Asp Ile Gln Lys Thr Ile Lys Lys Thr Ala Arg Arg Glu Gln
        115                 120                 125

ctg atg aga gaa gag gct gag cag aag cgt tta aag act gtg cta gag      432
Leu Met Arg Glu Glu Ala Glu Gln Lys Arg Leu Lys Thr Val Leu Glu
    130                 135                 140

ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145                 150                 155                 160

ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165                 170                 175

aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180                 185                 190

aac atg agg ttg aat gag cag tat gag caa gca tct gtt cac ctg tgg      624
Asn Met Arg Leu Asn Glu Gln Tyr Glu Gln Ala Ser Val His Leu Trp
        195                 200                 205

gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210                 215                 220

gcc ctg aag gag gtt gtt gaa cgt att ctt caa act agt tac ttt gat      720
Ala Leu Lys Glu Val Val Glu Arg Ile Leu Gln Thr Ser Tyr Phe Asp
225                 230                 235                 240

agc acc cat aac cat cag aac ggg tta tgt gag gaa gaa gag gca gca      768
Ser Thr His Asn His Gln Asn Gly Leu Cys Glu Glu Glu Glu Ala Ala
                245                 250                 255

ccc aca cct gca gta gaa gac act gta gca gaa gct gag cct gat cca      816
Pro Thr Pro Ala Val Glu Asp Thr Val Ala Glu Ala Glu Pro Asp Pro
            260                 265                 270

gca gaa gaa ttt act gaa cct act gaa gtt gaa tcg act gag tat gta      864
Ala Glu Glu Phe Thr Glu Pro Thr Glu Val Glu Ser Thr Glu Tyr Val
        275                 280                 285

aac aga caa ttc atg gca gag act cag ttc agc agt agt gag aag gaa      912
```

```
Asn Arg Gln Phe Met Ala Glu Thr Gln Phe Ser Ser Ser Glu Lys Glu
    290                 295                 300

cag gta gat gag tgg aca gtt gaa acg gtt gag gtt gta aat tca ctg      960
Gln Val Asp Glu Trp Thr Val Glu Thr Val Glu Val Val Asn Ser Leu
305                 310                 315                 320

cag caa caa aca caa gct aca tct cct cca gtt cct gaa cct cat aca     1008
Gln Gln Gln Thr Gln Ala Thr Ser Pro Pro Val Pro Glu Pro His Thr
                325                 330                 335

ctc act act gtg gct caa gca gat cct ctt gtt aga aga cag aga gta     1056
Leu Thr Thr Val Ala Gln Ala Asp Pro Leu Val Arg Arg Gln Arg Val
            340                 345                 350

cag gac ctt atg gcc cag atg cag ggt cca tat aac ttc atg cag gac     1104
Gln Asp Leu Met Ala Gln Met Gln Gly Pro Tyr Asn Phe Met Gln Asp
        355                 360                 365

tct atg ctg gag ttt gag aac cag aca ctt gat cct gcc att gta tct     1152
Ser Met Leu Glu Phe Glu Asn Gln Thr Leu Asp Pro Ala Ile Val Ser
    370                 375                 380

gca cag ccc atg aat cca gca cag aat ttg gac atg ccg caa atg gtc     1200
Ala Gln Pro Met Asn Pro Ala Gln Asn Leu Asp Met Pro Gln Met Val
385                 390                 395                 400

tgc cct cca gtt cat act gag tca aga ctt gcc cag cct aat caa gtt     1248
Cys Pro Pro Val His Thr Glu Ser Arg Leu Ala Gln Pro Asn Gln Val
                405                 410                 415

cct gtg caa cca gaa gct acg cag gtt ccc ttg gtt tca tct aca agt     1296
Pro Val Gln Pro Glu Ala Thr Gln Val Pro Leu Val Ser Ser Thr Ser
            420                 425                 430

gag gga tat aca gcc tcc cag ccc atg tat cag cct tct cat acc aca     1344
Glu Gly Tyr Thr Ala Ser Gln Pro Met Tyr Gln Pro Ser His Thr Thr
        435                 440                 445

gag caa cgg cca cag aag gaa tcc att gac cag att cag gct tca atg     1392
Glu Gln Arg Pro Gln Lys Glu Ser Ile Asp Gln Ile Gln Ala Ser Met
    450                 455                 460

tca ctg aat gca gac cag acc ccg tca tca tca tca ctt ccc act gca     1440
Ser Leu Asn Ala Asp Gln Thr Pro Ser Ser Ser Ser Leu Pro Thr Ala
465                 470                 475                 480

tcc cag ccg caa gtt ttc caa gct gga tct agc aaa cct ttg cat agc     1488
Ser Gln Pro Gln Val Phe Gln Ala Gly Ser Ser Lys Pro Leu His Ser
                485                 490                 495

agc gga atc aat gtt aat gca gct cca ttc caa tcc atg caa aca gta     1536
Ser Gly Ile Asn Val Asn Ala Ala Pro Phe Gln Ser Met Gln Thr Val
            500                 505                 510

ttc aac atg aat gca cct gtt cct cct gtt aat gag cca gaa gcc ctt     1584
Phe Asn Met Asn Ala Pro Val Pro Pro Val Asn Glu Pro Glu Ala Leu
        515                 520                 525

aag caa caa aat cag tac cag gcc agt tac aac cag agt ttc tcc aat     1632
Lys Gln Gln Asn Gln Tyr Gln Ala Ser Tyr Asn Gln Ser Phe Ser Asn
    530                 535                 540

cag cca cac caa gta gaa caa tca gat ctt cag caa gaa cag ctc cag     1680
Gln Pro His Gln Val Glu Gln Ser Asp Leu Gln Gln Glu Gln Leu Gln
545                 550                 555                 560

aca gtg gtt ggt act tac cat ggt tct ccg gac cag acc cat caa gtg     1728
Thr Val Val Gly Thr Tyr His Gly Ser Pro Asp Gln Thr His Gln Val
                565                 570                 575

gca gga aac cac cag caa cct ccc cag cag aat act gga ttt cca cgc     1776
Ala Gly Asn His Gln Gln Pro Pro Gln Gln Asn Thr Gly Phe Pro Arg
            580                 585                 590

aac agt cag cct tat tac aac agt cgg gga gtg tct cgt ggt gga tca     1824
Asn Ser Gln Pro Tyr Tyr Asn Ser Arg Gly Val Ser Arg Gly Gly Ser
        595                 600                 605
```

```
cgt ggg act cgt gga ttg atg aat ggt tac agg gga cct gca aat gga     1872
Arg Gly Thr Arg Gly Leu Met Asn Gly Tyr Arg Gly Pro Ala Asn Gly
    610                 615                 620

ttt aga gga gga tat gat ggc tac cgt cct tca ttt tcc aac act ccg     1920
Phe Arg Gly Gly Tyr Asp Gly Tyr Arg Pro Ser Phe Ser Asn Thr Pro
625                 630                 635                 640

aac agt ggt tac acg cag ccc caa ttt aat gct cct cga gat tat tca     1968
Asn Ser Gly Tyr Thr Gln Pro Gln Phe Asn Ala Pro Arg Asp Tyr Ser
                645                 650                 655

aac tac cag cgg gat gga tat cag cag aac ttc aaa cgt ggt tct gga     2016
Asn Tyr Gln Arg Asp Gly Tyr Gln Gln Asn Phe Lys Arg Gly Ser Gly
            660                 665                 670

caa agt ggg cct cgg gga gct cct cga ggt cgt gga ggg ccc cca aga     2064
Gln Ser Gly Pro Arg Gly Ala Pro Arg Gly Arg Gly Gly Pro Pro Arg
        675                 680                 685

cca aac aga ggg atg cct caa atg aac gct cag caa gtg aat taa         2109
Pro Asn Arg Gly Met Pro Gln Met Asn Ala Gln Gln Val Asn
    690                 695                 700


<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255
```

```
Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
    290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
        355                 360                 365

Ser Met Leu Glu Phe Glu Asn Gln Thr Leu Asp Pro Ala Ile Val Ser
    370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
        435                 440                 445

Glu Gln Arg Pro Gln Lys Glu Ser Ile Asp Gln Ile Gln Ala Ser Met
    450                 455                 460

Ser Leu Asn Ala Asp Gln Thr Pro Ser Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Pro Val Asn Glu Pro Glu Ala Leu
        515                 520                 525

Lys Gln Gln Asn Gln Tyr Gln Ala Ser Tyr Asn Gln Ser Phe Ser Asn
    530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
        595                 600                 605

Arg Gly Thr Arg Gly Leu Met Asn Gly Tyr Arg Gly Pro Ala Asn Gly
    610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670
```

```
Gln Ser Gly Pro Arg Gly Ala Pro Arg Gly Arg Gly Gly Pro Pro Arg
        675                 680                 685

Pro Asn Arg Gly Met Pro Gln Met Asn Ala Gln Gln Val Asn
    690                 695                 700


<210> SEQ ID NO 31
<211> LENGTH: 20
<212> TYPE: DNA
<213> ORGANISM: Artificial
<220> FEATURE:
<223> OTHER INFORMATION: T3 primer

<400> SEQUENCE: 31

aattaaccct cactaaaggg                                                    20


<210> SEQ ID NO 32
<211> LENGTH: 19
<212> TYPE: DNA
<213> ORGANISM: Artificial
<220> FEATURE:
<223> OTHER INFORMATION: T7 primer

<400> SEQUENCE: 32

taatacgact cactatagg                                                     19


<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33

aaggtttgaa tggagtgc                                                      18


<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34

tgctcctttt caccactg                                                      18


<210> SEQ ID NO 35
<211> LENGTH: 18
<212> TYPE: DNA
<213> ORGANISM: Artificial
<220> FEATURE:
<223> OTHER INFORMATION: GAPDH primer

<400> SEQUENCE: 35

gggctgcttt taactctg                                                      18


<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36

ccaggaaatg agcttgac                                                      18
```

<210> SEQ ID NO 37
<211> LENGTH: 27
<212> TYPE: DNA
<213> ORGANISM: Artificial
<220> FEATURE:
<223> OTHER INFORMATION: primer

<400> SEQUENCE: 37
catatggcat taagtcaaga tattcag 27

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
ggtacctttg cggcatccct ctg 23

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39
catatgccgt cggccaccag c 21

<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
ggtaccattc acttgctgag tg 22

<210> SEQ ID NO 41
<211> LENGTH: 23
<212> TYPE: DNA
<213> ORGANISM: Artificial
<220> FEATURE:
<223> OTHER INFORMATION: primer

<400> SEQUENCE: 41
gagctcatgc cctcggccac cag 23

<210> SEQ ID NO 42
<211> LENGTH: 23
<212> TYPE: DNA
<213> ORGANISM: Artificial
<220> FEATURE:
<223> OTHER INFORMATION: primer

<400> SEQUENCE: 42
ctcgagttaa ttcacttgct gag 23

<210> SEQ ID NO 43
<211> LENGTH: 14
<212> TYPE: PRT
<213> ORGANISM: Homo sapiens

<400> SEQUENCE: 43

```
Arg Asn Leu Glu Lys Lys Lys Gly Lys Leu Asp Asp Tyr Gln
1               5                   10


<210> SEQ ID NO 44
<211> LENGTH: 148
<212> TYPE: PRT
<213> ORGANISM: Mus musculus

<400> SEQUENCE: 44

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145


<210> SEQ ID NO 45
<211> LENGTH: 132
<212> TYPE: PRT
<213> ORGANISM: Mus musculus

<400> SEQUENCE: 45

Ala Val Leu Arg Cys Ser Arg Gly Leu Leu Val Ile Trp Ile Ser Asp
1               5                   10                  15

Ile Gln Leu Thr Gln Ser Pro Ser Ser Leu Ala Val Thr Ala Gly Glu
            20                  25                  30

Lys Val Thr Met Ser Cys Lys Ser Ser Gln Ser Leu Leu Trp Ser Val
        35                  40                  45

Asn Gln Lys Asn Tyr Leu Ser Trp Tyr Gln Gln Lys Gln Arg Gln Pro
    50                  55                  60

Pro Lys Leu Leu Ile Tyr Gly Ala Ser Ile Arg Glu Ser Trp Val Pro
65                  70                  75                  80

Asp Arg Phe Thr Gly Ser Gly Ser Gly Thr Asp Phe Thr Leu Thr Ile
                85                  90                  95

Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
    130


<210> SEQ ID NO 46
<211> LENGTH: 117
```

```
<212> TYPE: PRT
<213> ORGANISM: Mus musculus

<400> SEQUENCE: 46

Arg Thr Thr Ser His Met Asp Ser Asp Ile Gln Leu Thr Gln Ser Pro
1               5                   10                  15

Ala Ser Leu Ser Ala Ser Val Gly Glu Thr Val Thr Ile Thr Cys Arg
            20                  25                  30

Ala Ser Gly Asn Ile His Asn Tyr Leu Ala Trp Tyr Gln Gln Lys Gln
        35                  40                  45

Gly Lys Ser Pro Gln Leu Leu Val Tyr Asn Ala Lys Thr Leu Ala Asp
    50                  55                  60

Gly Val Pro Ser Arg Phe Ser Gly Ser Gly Ser Gly Thr Gln Tyr Ser
65                  70                  75                  80

Leu Lys Ile Asn Ser Leu Gln Pro Glu Asp Phe Gly Ser Tyr Tyr Cys
                85                  90                  95

Gln His Phe Trp Ser Thr Leu Thr Phe Gly Gly Gly Thr Lys Leu Glu
            100                 105                 110

Ile Lys Gln Ser Asp
        115


<210> SEQ ID NO 47
<211> LENGTH: 94
<212> TYPE: PRT
<213> ORGANISM: Mus musculus

<400> SEQUENCE: 47

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Ala Gly Thr Lys Leu Glu Ile Lys Gln
                85                  90


<210> SEQ ID NO 48
<211> LENGTH: 105
<212> TYPE: PRT
<213> ORGANISM: Mus musculus

<400> SEQUENCE: 48

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
```

```
                85                  90                  95

Val Gln Val Pro Arg Arg Arg Ser Asn
            100                 105


<210> SEQ ID NO 49
<211> LENGTH: 100
<212> TYPE: PRT
<213> ORGANISM: Mus musculus

<400> SEQUENCE: 49

Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100


<210> SEQ ID NO 50
<211> LENGTH: 90
<212> TYPE: PRT
<213> ORGANISM: Mus musculus

<400> SEQUENCE: 50

Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
    50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
                85                  90


<210> SEQ ID NO 51
<211> LENGTH: 116
<212> TYPE: PRT
<213> ORGANISM: Mus musculus

<400> SEQUENCE: 51

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
        35                  40                  45

Tyr Pro Gly Asp Gly Asp Thr Arg Tyr Thr Gln Lys Phe Lys Gly Lys
    50                  55                  60
```

```
Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115


<210> SEQ ID NO 52
<211> LENGTH: 100
<212> TYPE: PRT
<213> ORGANISM: Mus musculus

<400> SEQUENCE: 52

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45

Val Pro Ser Arg Phe Ser Gly Ser Gly Ser Gly Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
            100


<210> SEQ ID NO 53
<211> LENGTH: 108
<212> TYPE: PRT
<213> ORGANISM: Mus musculus

<400> SEQUENCE: 53

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30

Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Tyr Gly Ser Ser Leu Ala Tyr
                85                  90                  95

Trp Gly Gln Gly Thr Thr Val Thr Val Ser Ser Lys
            100                 105


<210> SEQ ID NO 54
<211> LENGTH: 104
<212> TYPE: PRT
<213> ORGANISM: Mus musculus

<400> SEQUENCE: 54
```

```
Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100


<210> SEQ ID NO 55
<211> LENGTH: 109
<212> TYPE: PRT
<213> ORGANISM: Mus musculus

<400> SEQUENCE: 55

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105


<210> SEQ ID NO 56
<211> LENGTH: 94
<212> TYPE: PRT
<213> ORGANISM: Mus musculus

<400> SEQUENCE: 56

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90


<210> SEQ ID NO 57
<211> LENGTH: 111
```

<212> TYPE: PRT
<213> ORGANISM: Mus musculus

<400> SEQUENCE: 57

```
Pro Ala Cys Leu Pro Gly Gly Ser Leu Arg Leu Ser Cys Ala Thr Ser
1               5                   10                  15

Gly Phe Thr Phe Thr Asp Tyr Tyr Met Ser Trp Val Arg Gln Pro Pro
            20                  25                  30

Gly Lys Ala Leu Glu Trp Leu Gly Phe Ile Arg Asn Lys Ala Asn Gly
        35                  40                  45

Tyr Thr Thr Glu Tyr Ser Ala Ser Val Lys Gly Arg Phe Thr Ile Ser
    50                  55                  60

Arg Asp Asn Ser Gln Ser Ile Leu Tyr Leu Gln Met Asn Thr Leu Arg
65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
            100                 105                 110
```

<210> SEQ ID NO 58
<211> LENGTH: 102
<212> TYPE: PRT
<213> ORGANISM: Mus musculus

<400> SEQUENCE: 58

```
Arg Leu Pro Phe Tyr Ser Leu Glu Gln Arg Ala Thr Ile Ser Tyr Arg
1               5                   10                  15

Ala Ser Lys Asn Val Ser Thr Ser Gly Tyr Ser Tyr Met His Trp Asn
            20                  25                  30

Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
            100
```

<210> SEQ ID NO 59
<211> LENGTH: 101
<212> TYPE: PRT
<213> ORGANISM: Mus musculus

<400> SEQUENCE: 59

```
Val Ser Cys Lys Ala Ser Gly Tyr Thr Phe Thr Ser Tyr Trp Met His
1               5                   10                  15

Trp Val Lys Gln Arg Pro Gly Gln Gly Leu Glu Trp Ile Gly Met Ile
            20                  25                  30

Asp Pro Ser Asn Ser Glu Thr Arg Leu Asn Gln Lys Phe Lys Asp Lys
        35                  40                  45

Ala Thr Leu Asn Val Asp Lys Ser Ser Asn Thr Ala Tyr Met Gln Leu
    50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
```

```
                85                  90                  95

Thr Val Ser Ser Lys
            100


<210> SEQ ID NO 60
<211> LENGTH: 99
<212> TYPE: PRT
<213> ORGANISM: Mus musculus

<400> SEQUENCE: 60

Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
            20                  25                  30

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Glu Asp Ala Ala Thr Tyr Tyr Cys
65                  70                  75                  80

Gln His Ile Arg Glu Leu Thr Arg Ser Glu Glu Val Pro Ser Trp Arg
                85                  90                  95

Ser Asn Lys


<210> SEQ ID NO 61
<211> LENGTH: 58
<212> TYPE: PRT
<213> ORGANISM: Homo sapiens

<400> SEQUENCE: 61

Val Phe Gln Ser Asn Tyr Phe Asp Ser Thr His Asn His Gln Asn Gly
1               5                   10                  15

Leu Cys Glu Glu Glu Glu Ala Ala Ser Ala Pro Ala Val Glu Asp Gln
            20                  25                  30

Val Pro Glu Ala Glu Pro Glu Pro Ala Glu Glu Tyr Thr Glu Gln Ser
        35                  40                  45

Glu Val Glu Ser Thr Glu Tyr Val Asn Arg
    50                  55


<210> SEQ ID NO 62
<211> LENGTH: 15
<212> TYPE: PRT
<213> ORGANISM: Homo sapiens

<400> SEQUENCE: 62

Tyr Thr Glu Gln Ser Glu Val Glu Ser Thr Glu Tyr Val Asn Arg
1               5                   10                  15


<210> SEQ ID NO 63
<211> LENGTH: 11
<212> TYPE: PRT
<213> ORGANISM: Homo sapiens

<400> SEQUENCE: 63

Ser Glu Val Glu Ser Thr Glu Tyr Val Asn Arg
1               5                   10
```